US011464801B2

(12) United States Patent
Orentas et al.

(10) Patent No.: US 11,464,801 B2
(45) Date of Patent: Oct. 11, 2022

(54) COMPOSITIONS AND METHODS FOR TREATING CANCER WITH ANTI-CD33 IMMUNOTHERAPY

(71) Applicants: Lentigen Technology, Inc., Gaithersburg, MD (US); The U.S.A., as represented by the Secretary, Department of Health and Human Services, Bethesda, MD (US)

(72) Inventors: Rimas Orentas, Washington, DC (US); Dina Schneider, Potomac, MD (US); Boro Dropulic, Ellicott City, MD (US); Dimiter S. Dimitrov, Frederick, MD (US); Zhongyu Zhu, Frederick, MD (US)

(73) Assignees: LENTIGEN TECHNOLOGY, INC., Gaithersburg, MD (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 456 days.

(21) Appl. No.: 16/588,357

(22) Filed: Sep. 30, 2019

(65) Prior Publication Data
US 2020/0101109 A1 Apr. 2, 2020

Related U.S. Application Data

(62) Division of application No. 15/934,770, filed on Mar. 23, 2018, now Pat. No. 10,426,797.

(60) Provisional application No. 62/620,139, filed on Jan. 22, 2018, provisional application No. 62/476,438, filed on Mar. 24, 2017.

(51) Int. Cl.
| | |
|---|---|
| *A61K 35/17* | (2015.01) |
| *C07K 16/28* | (2006.01) |
| *C07K 14/725* | (2006.01) |
| *C07K 14/705* | (2006.01) |
| *A61P 35/02* | (2006.01) |
| *A61K 39/395* | (2006.01) |
| *A61K 48/00* | (2006.01) |
| *A61K 39/00* | (2006.01) |

(52) U.S. Cl.
CPC ........ *A61K 35/17* (2013.01); *A61K 39/39558* (2013.01); *A61K 48/0016* (2013.01); *A61P 35/02* (2018.01); *C07K 14/7051* (2013.01); *C07K 14/70517* (2013.01); *C07K 16/2803* (2013.01); *A61K 2039/505* (2013.01); *A61K 2039/5152* (2013.01); *A61K 2039/5156* (2013.01); *A61K 2039/5158* (2013.01); *C07K 2317/24* (2013.01); *C07K 2317/53* (2013.01); *C07K 2317/62* (2013.01); *C07K 2317/622* (2013.01); *C07K 2317/73* (2013.01); *C07K 2319/03* (2013.01)

(58) Field of Classification Search
None
See application file for complete search history.

(56) References Cited

U.S. PATENT DOCUMENTS

| | | |
|---|---|---|
| 10,426,797 B2 | 10/2019 | Orentas et al. |
| 2014/0186365 A1 | 7/2014 | Robinson |
| 2018/0280438 A1 | 10/2018 | Orentas et al. |

FOREIGN PATENT DOCUMENTS

| | | |
|---|---|---|
| CN | 104877032 | 9/2015 |
| CN | 105820255 | 8/2016 |
| CN | 109843922 | 6/2019 |
| EP | 2332994 | 6/2011 |
| WO | WO 2008143702 | 11/2008 |
| WO | WO 2012079000 | 6/2012 |
| WO | WO 2014052064 | 4/2014 |
| WO | WO 2015150526 | 10/2015 |
| WO | WO 2016014576 | 1/2016 |
| WO | WO 2016/174408 | 11/2016 |
| WO | WO 2016/174461 | 11/2016 |
| WO | WO 2016/201394 | 12/2016 |
| WO | WO 2017075399 | 5/2017 |
| WO | WO 2018045325 | 3/2018 |

OTHER PUBLICATIONS

PCT International Preliminary Report on Patentability in International Patent Application. No. PCT/US2018/024183, dated Oct. 3, 2019, 9 pages.

Bowie, et al., "Deciphering the Message in Protein Sequences: Tolerances to Amino Acid Substitutions," Science, 1990, 247:1306-1310.

Ceppi, et al., "Lymphocyte apheresis for chimeric antigen receptor T-cell manufacturing in children and young adults with leukemia and neuroblastoma," Transfusion, 2018, 58:1414-1420.

Eck, et al., Goodman and Gilman's, McGraw-Hill, Health Profession Division, 1996, pp. 77-101.

Fromm, et al., "Flow cytometric analysis of CD123 is useful for immunophenotyping classical Hodgkin lymphoma," Cytometry Part B, 2011, 808:91-99.

Gill, et al., "Preclinical targeting of human acute myeloid leukemia and myeloablation using chimeric antigen receptor-modified T cells," Blood, 2014, 123(15):2343-2354.

International Search Report and Written Opinion issued in PCT/US2018/024183, dated Jun. 7, 2018, 14 pages.

(Continued)

*Primary Examiner* — Maria G Leavitt
(74) *Attorney, Agent, or Firm* — Serge Sira, Esq.; Gregory J. Hwa, Esq.; Fish & Richardson P.C.

(57) ABSTRACT

Chimeric antigen receptors containing CD33 antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

15 Claims, 30 Drawing Sheets
Specification includes a Sequence Listing.

(56) References Cited

OTHER PUBLICATIONS

Kean, et al., "Defining success with cellular therapeutics: the current landscape for clinical end point and toxicity analysis," Blood, 2018, 131(24):23630-2639.

Kim, et al., Genetic Inactivation of CD33 in Hematopoietic Stem Cells to Enable CAR T Cell Immunotherapy for Acute Myeloid Leukemia, Cell, 2018, 173:1439-1453.

Mardiros, et al., "T cells expressing CD123-specific chimeric antigen receptors exhibit specific cytolytic effector functions and antitumor effects against human acute myeloid leukemia," Blood, 2013, 122(18):3138-3148.

Ngo, et al., "Computational complexity, protein structure prediction, and the levinthal paradox," in The Protein Folding Problem and Tertiary Structure Prediction, Merz et al., eds., Birkhauser Boston: Boston, MA, 1994, pp. 433-440 and 492-495.

Pizzitola, et al., "Chimeric antigen receptors against CD33/CD123 antigens efficiently target primary acute myeloid leukemia cells in vivo," Leukemia, 2014 28:1596-1605.

Tettamanti, et al., "Targeting of acute myeloid leukaemia by cytokine-induced killer cells redirected with a novel CD123-specific chimeric antigen receptor," British Journal of Haematology, 2013, 161:389-401.

Voskoglou-Nomikos, et al., "Clinical Predictive Value of the in Vitro Cell Line, Human Xenograft, and Mouse Allograft Preclinical Cancer Models," Clinical Cancer Research, 2003, 9:4227-4239.

Wang, et al., "Treatment of CD33-directed Chimeric Antigen Receptor-modified T Cells in One Patient With Relapsed and Refractory Acute Myeloid Leukemia," Molecular Therapy, 2015, 23(1):184-191.

Yan, et al., "Two-Amino Acid Molecular Switch in an Epithelial Morphogen That Regulates Binding to Two Distinct Receptors," Science, 2000, 290:523-527.

Kenderian et al., "CD33-specific chimeric antigen receptor T cells exhibit potent preclinical activity against human acute myeloid leukemia," Leukemia, Aug. 2015, 29(8):1637, 40 pages.

| | | | | | | | |
|---|---|---|---|---|---|---|---|
| A | Leader Peptide | Anti-CD33 binder | CD8 hinge | CD8 TM | 4-1BB | CD3z | |
| B | Leader Peptide | Anti-CD33 binder | CD8 hinge | CD8 TM | | CD3z | |
| C | Leader Peptide | Anti-CD33 binder | TNFRSF19 hinge | TNFRSF19 TM | 4-1BB | CD3z | |
| D | Leader Peptide | Anti-CD33 binder | TNFRSF19 hinge | TNFRSF19 TM | | CD3z | |
| E | Leader Peptide | Anti-CD33 binder | CH2CH3 IgG4 hinge | CD8 TM | | CD3z | |
| F | Leader Peptide | Anti-CD33 binder | CD8 hinge | CD8 TM | 4-1BB | CD3z | tEGFR |
| G | Leader Peptide | Anti-CD33 binder | CD8 hinge | CD8 TM | | CD3z | tEGFR |

FIGURE 1

LTG 1905 EF1a VH-2 CD33 -CD8 TM-41BB-CD3 zeta nucleotide sequence

ATGCTGCTGCTGGTGACCAGCCTGCTGCTGTGCGAACTGCCGCATCCGGCGTT
TCTGCTGATTCCGGAGGTGCAGCTGGTGGAGTCTGGGGGAGGCTTGGTACAGCCTGG
AGGGTCCCTGAGACTCTCCTGTGCAGCCTCTGGATTCACCTTCAGTAGCTATGGCATG
AGCTGGGTCCGCCAGGCTCCAAGGAAGGGCCTGGAGTGGATTGGGGAAATCAATCAT
AGTGGAAGCACCAACTACAACCCGTCCCTCAAGAGTCGAGTCACCATCTCCAGAGAC
AATTCCAAGAACACGCTGTATCTGCAAATGAACAGCCTGAGAGCCGAGGACACAGCC
ACGTATTACTGTGCGAGACCCCTCAACTACTACTACTACATGGACGTCTGGGGCA
AAGGGACCACGGTCACCGTCTCCTCAGCGGCCGCAACTACCACCCCTGCCCCTCGGC
CGCCGACTCCGGCCCCAACCATCGCAAGCCAACCCCTCTCCTTGCGCCCCGAAGCTTG
CCGCCCGGCCGCGGGTGGAGCCGTGCATACCCGGGGGCTGGACTTTGCCTGCGATAT
CTACATTTGGGCCCCGCTGGCCGGCACTTGCGGCGTGCTCCTGCTGTCGCTGGTCATC
ACCCTTTACTGCAAGAGGGGCCGGAAGAAGCTGCTTTACATCTTCAAGCAGCCGTTC
ATGCGGCCCGTGCAGACGACTCAGGAAGAGGACGGATGCTCGTGCAGATTCCCTGAG
GAGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAAC
CACGGCGGAAAAACCCTCAGGAAGGACTGTACAACGAACTCCAGAAAGACAAGATG
GCGGAAGCCTACTCAGAAATCGGGATGAAGGGAGAGCGGAGGAGGGGAAAGGGTCA
CGACGGGCTGTACCAGGGACTGAGCACCGCCACTAAGGATACCTACGATGCCTTGCA
TATGCAAGCACTCCCACCCCGG

LTG 1905 EF1a VH-2 CD33 -CD8 TM-41BB-CD3 zeta amino acid sequence

MLLLVTSLLLCELPHPAFLLIPEVQLVESGGGLVQPGGSLRLSCAASGFTFSSYGMS
WVRQAPRKGLEWIGEINHSGSTNYNPSLKSRVTISRDNSKNTLYLQMNSLRAEDTATYY
CARPLNYYYYYMDVWGKGTTVTVSSAAATTTPAPRPPTPAPTIASQPLSLRPEACRPAAG
GAVHTRGLDFACDIYIWAPLAGTCGVLLLSLVITLYCKRGRKKLLYIFKQPFMRPVQTTQ
EEDGCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLYQGLSTAT
KDTYDALHMQALPPR

FIGURE 2A

LTG 1906 EF1a- VH-4 CD33 -CD8 TM-41BB-CD3 zeta

ATGCTGCTGCTGGTGACCAGCCTGCTGCTGTGCGAACTGCCGCATCCGGCGTT
TCTGCTGATTCCGGAGGTGCAGCTGGTGGAGTCTGGGGGAGGCTTGGTACAGCCTGG
AGGGTCCCTGAGACTCTCCTGTGCAGCCTCTGGATTCACCTTCAGTAGCTATGGCATG
AGCTGGGTCCGCCAGGCTCCAAGACAAGGGCTTGAGTGGGTGGCCAACATAAAGCA
AGATGGAAGTGAGAAATACTATGCGGACTCAGTGAAGGGCCGATTCACCATCTCCAG
AGACAATTCCAAGAACACGCTGTATCTGCAAATGAACAGCCTGAGAGCCGAGGACAC
AGCCACGTATTACTGTGCGAAAGAAAATGTGGACTGGGGCCAGGGCACCCTGGTCAC
CGTCTCCTCAGCGGCCGCAACTACCACCCCTGCCCCTCGGCCGCCGACTCCGGCCCCA
ACCATCGCAAGCCAACCCCTCTCCTTGCGCCCGAAGCTTGCCGCCCGGCCGCGGGT
GGAGCCGTGCATACCCGGGGGCTGGACTTTGCCTGCGATATCTACATTTGGGCCCCGC
TGGCCGGCACTTGCGGCGTGCTCCTGCTGTCGCTGGTCATCACCCTTTACTGCAAGAG
GGGCCGGAAGAAGCTGCTTTACATCTTCAAGCAGCCGTTCATGCGGCCCGTGCAGAC
GACTCAGGAAGAGGACGGATGCTCGTGCAGATTCCCTGAGGAGGAAGAGGGGGGAT
GCGAACTGCGCGTCAAGTTCTCACGGTCCGCCGACGCCCCGCATATCAACAGGGCC
AGAATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAACCC
TCAGGAAGGACTGTACAACGAACTCCAGAAAGACAAGATGGCGGAAGCCTACTCAG
AAATCGGGATGAAGGGAGAGCGGAGGAGGGGAAAGGGTCACGACGGGCTGTACCAG
GGACTGAGCACCGCCACTAAGGATACCTACGATGCCTTGCATATGCAAGCACTCCCA
CCCCGG

LTG 1906 EF1a- VH-4 CD33 -CD8 TM-41BB-CD3 zeta amino acid sequence
MLLLVTSLLLCELPHPAFLLIPEVQLVESGGGLVQPGGSLRLSCAASGFTFSSYGMS
WVRQAPRQGLEWVANIKQDGSEKYYADSVKGRFTISRDNSKNTLYLQMNSLRAEDTAT
YYCAKENVDWGQGTLVTVSSAAATTTPAPRPPTPAPTIASQPLSLRPEACRPAAGGAVHT
RGLDFACDIYIWAPLAGTCGVLLLSLVITLYCKRGRKKLLYIFKQPFMRPVQTTQEEDGCS
CRFPEEEEGGCELRVKFSRSADAPAYQQGQNQLYNELNLGRREEYDVLDKRRGRDPEM
GGKPRRKNPQEGLYNELQKDKMAEAYSEIGMKGERRRGKGHDGLYQGLSTATKDTYD
ALHMQALPPR

FIGURE 2B

LTG1936 EF1a ScFv9 CD33 CD8 TM-41BB-CD3 zeta nucleotide sequence

ATGCTGCTGCTGGTGACCAGCCTGCTGCTGTGCGAACTGCCGCATCCGGCGTT
TCTGCTGATTCCGCAGGTGCAGCTGGTGCAATCTGGGGCAGAGGTGAAAAAGCCCGG
GGAGTCTCTGAGGATCTCCTGTAAGGGTTCTGGATTCAGTTTTCCCACCTACTGGATC
GGCTGGGTGCGCCAGATGCCCGGGAAAGGCCTGGAGTGGATGGGGATCATCTATCCT
GGTGACTCTGATACCAGATACAGCCCGTCCTTCCAAGGCCAGGTCACCATCTCAGCC
GACAAGTCCATCAGCACCGCCTACCTGCAGTGGAGCAGCCTGAAGGCCTCGGACACC
GCCATGTATTACTGTGCGAGACTAGTTGGAGATGGCTACAATACGGGGCTTTTGAT
ATCTGGGGCCAAGGGACAATGGTCACCGTCTCTTCAGGAGGTGGCGGGTCTGGTGGT
GGCGGTAGCGGTGGTGGCGGATCCGATATTGTGATGACCCACACTCCACTCTCTCTGT
CCGTCACCCCTGGACAGCCGGCCTCCATCTCCTGCAAGTCTAGTCAGAGCCTCCTGCA
TAGTAATGGAAAGACCTATTTGTATTGGTACCTGCAGAAGCCAGGCCAGCCTCCACA
GCTCCTGATCTATGGAGCTTCCAACCGGTTCTCTGGAGTGCCAGACAGGTTCAGTGGC
AGCGGGTCAGGGACAGATTTCACACTGAAAATCAGCCGGGTGGAGGCTGAGGATGTT
GGGGTTTATTACTGCATGCAAAGTATACAGCTTCCTATCACCTTCGGCCAAGGGACAC
GACTGGAGATTAAAGCGGCCGCAACTACCACCCCTGCCCCTCGGCCGCCGACTCCGG
CCCCAACCATCGCAAGCCAACCCCTCTCCTTGCGCCCCGAAGCTTGCCGCCCGGCCGC
GGGTGGAGCCGTGCATACCCGGGGGCTGGACTTTGCCTGCGATATCTACATTTGGGC
CCCGCTGGCCGGCACTTGCGGCGTGCTCCTGCTGTCGCTGGTCATCACCCTTTACTGC
AAGAGGGGCCGGAAGAAGCTGCTTTACATCTTCAAGCAGCCGTTCATGCGGCCCGTG
CAGACGACTCAGGAAGAGGACGGATGCTCGTGCAGATTCCCTGAGGAGGAAGAGGG
GGGATGCGAACTGCGCGTCAAGTTCTCACGGTCCGCCGACGCCCCCGCATATCAACA
GGGCCAGAATCAGCTCTACAACGAGCTGAACCTGGGAAGGAGAGAGGAGTACGACG
TGCTGGACAAGCGACGCGGACGCGACCCGGAGATGGGGGGGAAACCACGGCGGAAA
AACCCTCAGGAAGGACTGTACAACGAACTCCAGAAAGACAAGATGGCGGAAGCCTA
CTCAGAAATCGGGATGAAGGGAGAGCGGAGGAGGGGAAAGGGTCACGACGGGCTGT
ACCAGGGACTGAGCACCGCCACTAAGGATACCTACGATGCCTTGCATATGCAAGCAC
TCCCACCCCGG

FIGURE 2C

LTG1936 (EF1a ScFv9 CD33 CD8 TM-41BB-CD3 zeta amino acid sequence

MLLLVTSLLLCELPHPAFLLIPQVQLVQSGAEVKKPGESLRISCKGSGFSFPTYWIG
WVRQMPGKGLEWMGIIYPGDSDTRYSPSFQGQVTISADKSISTAYLQWSSLKASDTAMY
YCARLVGDGYNTGAFDIWGQGTMVTVSSGGGGSGGGGSGGGGSDIVMTHTPLSLSVTP
GQPASISCKSSQSLLHSNGKTYLYWYLQKPGQPPQLLIYGASNRFSGVPDRFSGSGSGTDF
TLKISRVEAEDVGVYYCMQSIQLPITFGQGTRLEIKAAATTTPAPRPPTPAPTIASQPLSLRP
EACRPAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDGL
YQGLSTATKDTYDALHMQALPPR

FIGURE 2C Contd.

LTG1937 EF1a ScFv10 CD33 CD8 TM-41BB-CD3 zeta nucleotide sequence

ATGCTGCTGCTGGTGACCAGCCTGCTGCTGTGCGAACTGCCGCATCCGGCGTT
TCTGCTGATTCCGCAGGTACAGCTGCAGCAGTCAGGTCCAGGACTGGTGAAGCCCTC
GCAGACCCTCTCACTCACCTGTGCCATCTCCGGGGACAGTGTCTCTAGCAACACTGCT
GCTTGGAACTGGATCAGGCAGTCCCCATCGAGAGGCCTTGAGTGGCTGGGAAGGACA
TACTACAGGTCCAAGTGGTATAATGATTATGCAGTCCCTGTGAAAAGTCGAATAACC
ATCAACCCAGACACATCCAAGAACCAGTTCTCCCTGCAGCTGAACTCTGTGACTCCCG
AGGACACGGCTGTGTATTACTGTGCAAGAGAAACGTATTACTATGGTTCGGGGAGTT
ATTGGGATGCTTTTGATATCTGGGGCCAAGGGACCACGGTCACCGTCTCCTCAGGAG
GTGGCGGGTCTGGTAGTGGCGGTAGCGGTGGTGGCGGATCCCAGTCTGTCGTGACGC
AGCCGCCCTCAGTGTCTGCGGCCCCAGGACAGAAGGTCACCATCTCCTGCTCTGGAA
GCAGCTCCAACATTGGGAATAATTATGTATCCTGGTACCAGCAGCTCCCAGGCACGG
CCCCCAAACTCTTCATCTATAAAAATAATCAGCGGCCCTCAGAGGTCCCTGACCGATT
CTCTGGCTCCAAGTCTGGCACCTCAGCCTCCCTGGCCATCAGTGGGCTCCAGTCTGAC
GATGAGGCTGACTACTACTGTGCAGCATGGGATGACAGGCTGAATGGATATGTCTTC
GGAACTGGGACCAAGGTCACCGTCCTAGCGGCCGCAACTACCACCCCTGCCCCTCGG
CCGCCGACTCCGGCCCCAACCATCGCAAGCCAACCCCTCTCCTTGCGCCCCGAAGCTT
GCCGCCCGGCCGCGGGTGGAGCCGTGCATACCCGGGGGCTGGACTTTGCCTGCGATA
TCTACATTTGGGCCCCGCTGGCCGGCACTTGCGGCGTGCTCCTGCTGTCGCTGGTCAT
CACCCTTTACTGCAAGAGGGGCCGGAAGAAGCTGCTTTACATCTTCAAGCAGCCGTT
CATGCGGCCCGTGCAGACGACTCAGGAAGAGGACGGATGCTCGTGCAGATTCCCTGA
GGAGGAAGAGGGGGGATGCGAACTGCGCGTCAAGTTCTCACGGTCCGCCGACGCCCC
CGCATATCAACAGGGCCAGAATCAGCTCTACAACGAGCTGAACCTGGGAAGGAGAG
AGGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGAT
GGCGGAAGCCTACTCAGAAATCGGGATGAAGGGAGAGCGGAGGAGGGGAAAGGGTC
ACGACGGGCTGTACCAGGGACTGAGCACCGCCACTAAGGATACCTACGATGCCTTGC
ATATGCAAGCACTCCCACCCCGG

FIGURE 2D

LTG1937 EF1a ScFv10 CD33 CD8 TM-41BB-CD3 zeta amino acid sequence

MLLLVTSLLLCELPHPAFLLIPQVQLQQSGPGLVKPSQTLSLTCAISGDSVSSNTAA
WNWIRQSPSRGLEWLGRTYYRSKWYNDYAVPVKSRITINPDTSKNQFSLQLNSVTPEDT
AVYYCARETYYYGSGSYWDAFDIWGQGTTVTVSSGGGGSGSGGSGGGGSQSVVTQPPS
VSAAPGQKVTISCSGSSSNIGNNYVSWYQQLPGTAPKLFIYKNNQRPSEVPDRFSGSKSGT
SASLAISGLQSDDEADYYCAAWDDRLNGYVFGTGTKVTVLAAATTTPAPRPPTPAPTIAS
QPLSLRPEACRPAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYQQGQNQLYNELNL
GRREEYDVLDKRRGRDPEMGGKPRRKNPQEGLYNELQKDKMAEAYSEIGMKGERRRG
KGHDGLYQGLSTATKDTYDALHMQALPPR

FIGURE 2D Contd.

LTG1938 EF1a ScFv12 CD33 CD8 TM-41BB-CD3 zeta nucleotide sequence

ATGCTGCTGCTGGTGACCAGCCTGCTGCTGTGCGAACTGCCGCATCCGGCGTT
TCTGCTGATTCCGCAGGTACAGCTGCAGCAGTCAGGTCCAGGACTGGTGAAGCCCTC
GCAGACCCTCTCACTCACCTGTGCCATCTCCGGGGACAGTGTCTCTAGCAACAGTGCT
GCTTGGAACTGGATCAGGCAGTCCCCATCGAGAGGCCTTGAGTGGCTGGGAGGGACA
TACTACAGGTCCAAGTGGTATAATGATTATGCAGTATCTGTGAAAAGTCGAATAATT
ATCAACGCAGACACATCGAAGAACCAGTTCTCCCTGCAGCTGAACTCTGTGACTCCC
GAGGACACGGCTGTGTATTACTGTGCGAGGGGATATTACTATGATAGTACCGACTGG
TTCGACCCCTGGGGCCAGGGAACCCTGGTCACCGTCTCCTCAGGAGGTGGCGGGTCT
GGTGGTGGCGGTAGCGGTGGTGGCGGATCCTCTTCTGAGCTGACTCAGGACCCAACT
GTGTCTGTGGCCTTGGGACAGACAGTCAGGATCACATGCCAAGGAGACAGCCTCAGA
AGCTATTATGCAAGCTGGTACCAGCAGAAGCCAGGACAGGCCCCTGTACTTGTCATC
TATGGTAAAAACAACCGGCCCTCAGGGATCCCAGACCGATTCTCTGGCTCCAGCTCA
GGAAACACAGCTTCCTTGACCATCACTGGGGCTCAGGCGGAAGATGAGGCTGACTAT
TACTGTTCCTCCCGGGACGGCAGTGGTCATCCATATCTCTTCGGACCTGGGACCAAGG
TCACCGTTCTTGCGGCCGCAACTACCACCCCTGCCCCTCGGCCGCCGACTCCGGCCCC
AACCATCGCAAGCCAACCCCTCTCCTTGCGCCCCGAAGCTTGCCGCCCGGCCGCGGG
TGGAGCCGTGCATACCCGGGGGCTGGACTTTGCCTGCGATATCTACATTTGGGCCCCG
CTGGCCGGCACTTGCGGCGTGCTCCTGCTGTCGCTGGTCATCACCCTTTACTGCAAGA
GGGGCCGGAAGAAGCTGCTTTACATCTTCAAGCAGCCGTTCATGCGGCCCGTGCAGA
CGACTCAGGAAGAGGACGGATGCTCGTGCAGATTCCTGAGGAGGAAGAGGGGGGA
TGCGAACTGCGCGTCAAGTTCTCACGGTCCGCCGACGCCCCGCATATCAACAGGGC
CAGAATCAGCTCTACAACGAGCTGAACCTGGGAAGGAGAGAGGAGTACGACGTGCT
GGACAAGCGACGCGGACGCGACCCGGAGATGGGGGGGAAACCACGGCGGAAAAAC
CCTCAGGAAGGACTGTACAACGAACTCCAGAAAGACAAGATGGCGGAAGCCTACTC
AGAAATCGGGATGAAGGGAGAGCGGAGGAGGGAAAGGGTCACGACGGGCTGTACC
AGGGACTGAGCACCGCCACTAAGGATACCTACGATGCCTTGCATATGCAAGCACTCC
CACCCCGG

FIGURE 2E

LTG1938 EF1a ScFv12 CD33 CD8 TM-41BB-CD3 zeta amino acid sequence

MLLLVTSLLLCELPHPAFLLIPQVQLQQSGPGLVKPSQTLSLTCAISGDSVSSNSAA
WNWIRQSPSRGLEWLGGTYYRSKWYNDYAVSVKSRIIINADTSKNQFSLQLNSVTPEDT
AVYYCARGYYYDSTDWFDPWGQGTLVTVSSGGGGSGGGGSGGGGSSSELTQDPTVSVA
LGQTVRITCQGDSLRSYYASWYQQKPGQAPVLVIYGKNNRPSGIPDRFSGSSSGNTASLTI
TGAQAEDEADYYCSSRDGSGHPYLFGPGTKVTVLAAATTTPAPRPPTPAPTIASQPLSLRP
EACRPAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDGL
YQGLSTATKDTYDALHMQALPPR

FIGURE 2E Contd.

LTG1939 EF1a ScFv15 CD33 CD8 TM-41BB-CD3 zeta nucleotide sequence

ATGCTGCTGCTGGTGACCAGCCTGCTGCTGTGCGAACTGCCGCATCCGGCGTT
TCTGCTGATTCCGGAGGTCCAGCTGGTGCAGTCTGGAGCAGAGGTGAAAAAGCCCGG
GGAGTCTCTGAAGATCTCCTGTAAGGGTTCTGGATACAGCTTTACCAGCTACTGGATC
GGCTGGGTGCGCCAGATGCCCGGGAAAGGCCTGGAGTGGATGGGGATCATCTATCCT
GGTGACTCTGATACCAGATACAGCCCGTCCTTCCAAGGCCAGGTCACCATCTCAGCC
GACAAGTCCATCAGCACCGCCTACCTGCAGTGGAGCAGCCTGAAGGCCTCGGACACC
GCCATGTATTACTGTGCGAGACTGACTACGGCTGGGGGTATGGACGTCTGGGGCCAA
GGGACCACGGTCACCGTCTCCTCAGGAGGTGGCGGGTCTGGTGGTGGCGGTAGCGGT
GGTGGCGGATCCGAAATTGTGCTGACTCAGTCTCCACTCTCCCTGCCCGTCACCCTTG
GACAGCCGGCCTCCATCTCCTGCAGGTCTAGTCAAAGCCTCGTACACAGTGATGGAA
ACACCTACTTGAGTTGGCTTCACCAGAGGCCAGGCCAGCCTCCAAGACTCCTAATGT
ATAAGATTTCTAACCGGTTCTCTGGGGTCACAGACAGATTCAGTGGCAGCGGGTCAG
GGACAGATTTCACACTGAAAATCAGCCGGGTGGAGGCTGAGGATGTTGGGGTTTATT
ACTGCATGCAAGGTATACACCTACCGCTCACTTTCGGCGGAGGGACCAAGCTGGAGA
TCAAAGCGGCCGCAACTACCACCCCTGCCCCTCGGCCGCCGACTCCGGCCCCAACCA
TCGCAAGCCAACCCCTCTCCTTGCGCCCCGAAGCTTGCCGCCCGGCCGCGGGTGGAG
CCGTGCATACCCGGGGGCTGGACTTTGCCTGCGATATCTACATTTGGGCCCCGCTGGC
CGGCACTTGCGGCGTGCTCCTGCTGTCGCTGGTCATCACCCTTTACTGCAAGAGGGGC
CGGAAGAAGCTGCTTTACATCTTCAAGCAGCCGTTCATGCGGCCCGTGCAGACGACT
CAGGAAGAGGACGGATGCTCGTGCAGATTCCTGAGGAGGAAGAGGGGGGATGCGA
ACTGCGCGTCAAGTTCTCACGGTCCGCCGACGCCCCGCATATCAACAGGGCCAGAA
TCAGCTCTACAACGAGCTGAACCTGGGAAGGAGAGAGGAGTACGACGTGCTGGACA
AGCGACGCGGACGCGACCCGGAGATGGGGGGGAAACCACGGCGGAAAAACCCTCAG
GAAGGACTGTACAACGAACTCCAGAAAGACAAGATGGCGGAAGCCTACTCAGAAAT
CGGGATGAAGGGAGAGCGGAGGAGGGGAAAGGGTCACGACGGGCTGTACCAGGGA
CTGAGCACCGCCACTAAGGATACCTACGATGCCTTGCATATGCAAGCACTCCCACCC
CGG

FIGURE 2F

LTG1939 EF1a ScFv15 CD33 CD8 TM-41BB-CD3 zeta amino acid sequence

MLLLVTSLLLCELPHPAFLLIPEVQLVQSGAEVKKPGESLKISCKGSGYSFTSYWIG
WVRQMPGKGLEWMGIIYPGDSDTRYSPSFQGQVTISADKSISTAYLQWSSLKASDTAMY
YCARLTTAGGMDVWGQGTTVTVSSGGGGSGGGGSGGGGSEIVLTQSPLSLPVTLGQPAS
ISCRSSQSLVHSDGNTYLSWLHQRPGQPPRLLMYKISNRFSGVTDRFSGSGSGTDFTLKIS
RVEAEDVGVYYCMQGIHLPLTFGGGTKLEIKAAATTTPAPRPPTPAPTIASQPLSLRPEAC
RPAAGGAVHTRGLDFACDIYIWAPLAGTCGVLLLSLVITLYCKRGRKKLLYIFKQPFMRP
VQTTQEEDGCSCRFPEEEEGGCELRVKFSRSADAPAYQQGQNQLYNELNLGRREEYDVL
DKRRGRDPEMGGKPRRKNPQEGLYNELQKDKMAEAYSEIGMKGERRRGKGHDGLYQG
LSTATKDTYDALHMQALPPR

FIGURE 2F Contd.

LTG1936 – 65.2% CAR⁺
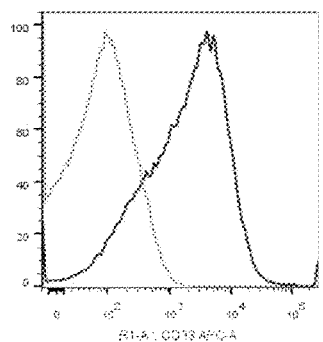
LTG1937 – 65.2% CAR⁺
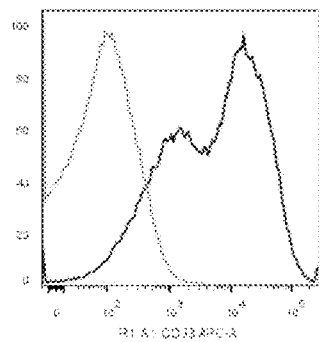
LTG1938 – 60.3% CAR⁺
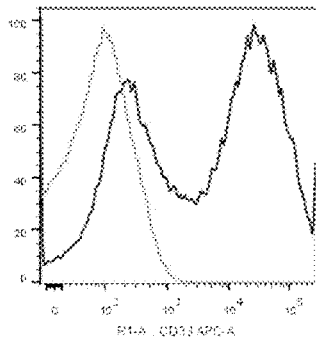
LTG1939 – 52.9% CAR⁺
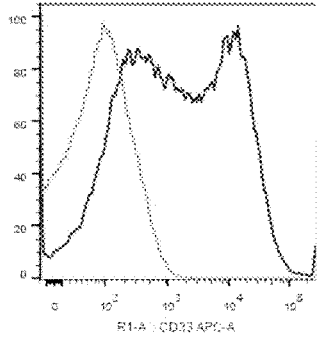
FIGURE 6

A
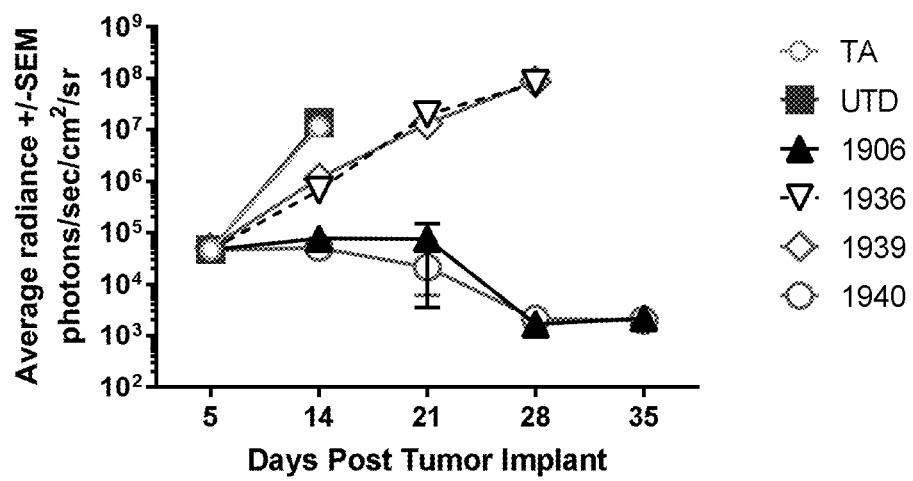
B
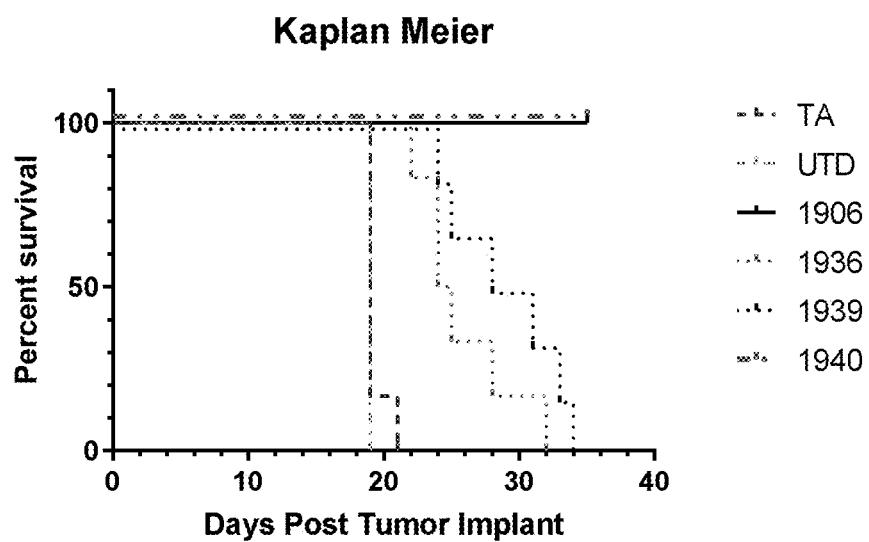
FIGURE 10

A
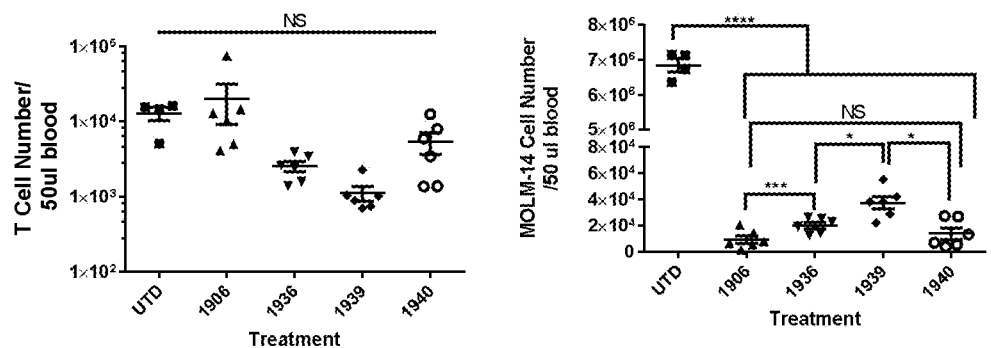
B
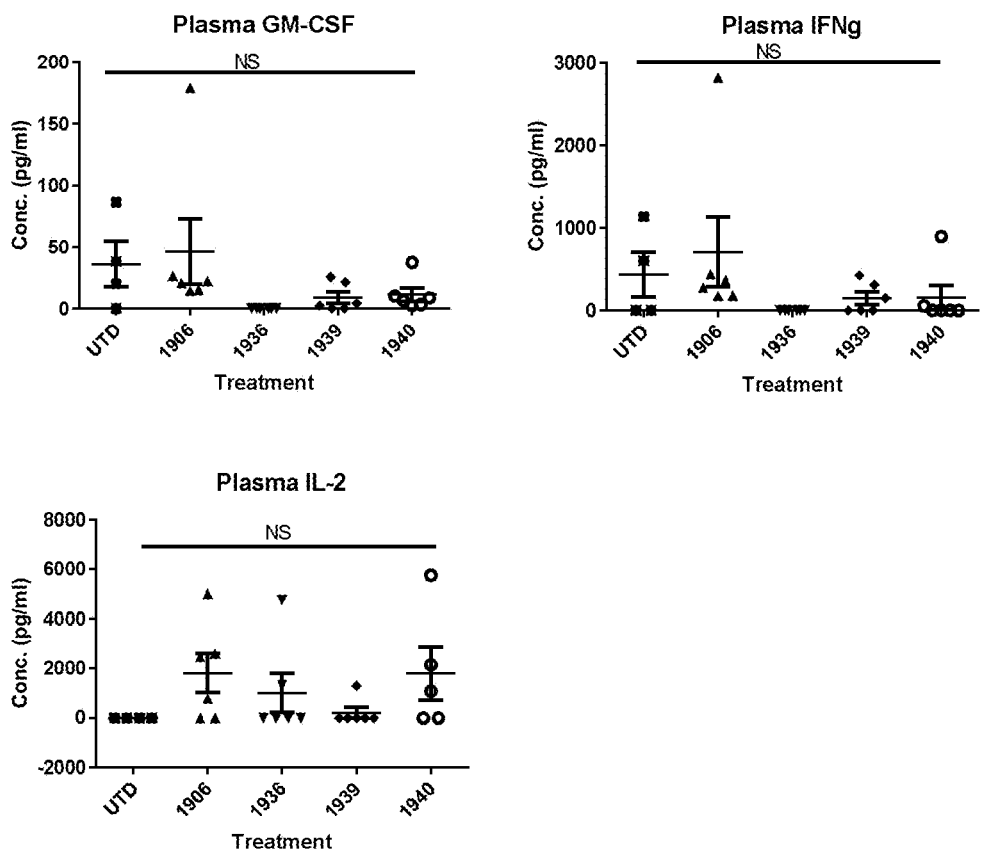
FIGURE 11

LTG1927 EF1a CD33_4 CD8 TM CD28 CD3 zeta nucleotides sequence

ATGCTGCTGCTGGTGACCAGCCTGCTGCTGTGCGAACTGCCGCATCCGGC
GTTTCTGCTGATTCCGGAGGTGCAGCTGGTGGAGTCTGGGGGAGGCTTGG
TACAGCCTGGAGGGTCCCTGAGACTCTCCTGTGCAGCCTCTGGATTCACCT
TCAGTAGCTATGGCATGAGCTGGGTCCGCCAGGCTCCAAGACAAGGGCTT
GAGTGGGTGGCCAACATAAAGCAAGATGGAAGTGAGAAATACTATGCGG
ACTCAGTGAAGGGCCGATTCACCATCTCCAGAGACAATTCCAAGAACACG
CTGTATCTGCAAATGAACAGCCTGAGAGCCGAGGACACAGCCACGTATTA
CTGTGCGAAAGAAAATGTGGACTGGGGCCAGGGCACCCTGGTCACCGTCT
CCTCAGCGGCCGCGACTACCACTCCTGCACCACGGCCACCTACCCCAGCC
CCCACCATTGCAAGCCAGCCACTTTCACTGCGCCCCGAAGCGTGTAGACC
AGCTGCTGGAGGAGCCGTGCATACCCGAGGGCTGGACTTCGCCTGTGACA
TCTACATCTGGGCCCCATTGGCTGGAACTTGCGGCGTGCTGCTCTTGTCTC
TGGTCATTACCCTGTACTGCCGGTCGAAGAGGTCCAGACTCTTGCACTCCG
ACTACATGAACATGACTCCTAGAAGGCCCGGACCCACTAGAAAGCACTAC
CAGCCGTACGCCCCTCCTCGGGATTTCGCCGCATACCGGTCCAGAGTGAA
GTTCAGCCGCTCAGCCGATGCACCGGCCTACCAGCAGGGACAGAACCAGC
TCTACAACGAGCTCAACCTGGGTCGGCGGGAAGAATATGACGTGCTGGAC
AAACGGCGCGGCAGAGATCCGGAGATGGGGGGAAAGCCGAGGAGGAAG
AACCCTCAAGAGGGCCTGTACAACGAACTGCAGAAGGACAAGATGGCGG
AAGCCTACTCCGAGATCGGCATGAAGGGAGAACGCCGGAGAGGGAAGGG
TCATGACGGACTGTACCAGGGCCTGTCAACTGCCACTAAGGACACTTACG
ATGCGCTCCATATGCAAGCTTTGCCCCGCGG

LTG1927 EF1a CD33_4 CD8 TM CD28 CD3 zeta amino acids sequence
MLLLVTSLLLCELPHPAFLLIPEVQLVESGGGLVQPGGSLRLSCAASGFTFSSY
GMSWVRQAPRQGLEWVANIKQDGSEKYYADSVKGRFTISRDNSKNTLYLQ
MNSLRAEDTATYYCAKENVDWGQGTLVTVSSAAATTTPAPRPPTPAPTIASQ
PLSLRPEACRPAAGGAVHTRGLDFACDIYIWAPLAGTCGVLLLSLVITLYCRS
KRSRLLHSDYMNMTPRRPGPTRKHYQPYAPPRDFAAYRSRVKFSRSADAPA
YQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR

FIGURE 12A

LTG_D0033 EF1a CD33_4 VH TNFRSF19 H_TM_CD28z nucleotide sequence

ATGCTGCTGCTGGTGACCAGCCTGCTGCTGTGCGAACTGCCGCATCCGGCGTTTCTGCTG
ATTCCGGAGGTGCAGCTGGTGGAGTCTGGGGGAGGCTTGGTACAGCCTGGAGGGTCCCTG
AGACTCTCCTGTGCAGCCTCTGGATTCACCTTCAGTAGCTATGGCATGAGCTGGGTCCGC
CAGGCTCCAAGACAAGGGCTTGAGTGGGTGGCCAACATAAAGCAAGATGGAAGTGAGAAA
TACTATGCGGACTCAGTGAAGGGCCGATTCACCATCTCCAGAGACAATTCCAAGAACACG
CTGTATCTGCAAATGAACAGCCTGAGAGCCGAGGACACAGCCACGTATTACTGTGCGAAA
GAAAATGTGGACTGGGGCCAGGGCACCCTGGTCACCGTCTCCTCAGCGGCCGCAGTCGGA
TTCCAAGACATGGAATGCGTGCCCTGCGGCGACCCGCCACCTCCTTACGAGCCGCACTGC
GCATCGAAGGTCAACCTCGTGAAGATCGCGAGCACCGCGTCCTCACCCCGGGATACTGCT
CTGGCCGCCGTGATTTGTTCCGCCTTGGCCACCGTGCTTCTGGCCCTGCTGATCCTCTGT
GTGATCCGGTCGAAGAGGTCCAGACTCTTGCACTCCGACTACATGAACATGACTCCTAGA
AGGCCCGGACCCACTAGAAAGCACTACCAGCCGTACGCCCCTCCTCGGGATTTCGCCGCA
TACCGGTCCAGAGTGAAGTTCAGCCGCTCAGCCGATGCACCGGCCTACCAGCAGGGACAG
AACCAGCTCTACAACGAGCTCAACCTGGGTCGGCGGGAAGAATATGACGTGCTGGACAAA
CGGCGCGGCAGAGATCCGGAGATGGGGGGAAAGCCGAGGAGGAAGAACCCTCAAGAGGGC
CTGTACAACGAACTGCAGAAGGACAAGATGGCGGAAGCCTACTCCGAGATCGGCATGAAG
GGAGAACGCCGGAGAGGGAAGGGTCATGACGGACTGTACCAGGGCCTGTCAACTGCCACT
AAGGACACTTACGATGCGCTCCATATGCAAGCTTTGCCCCCGCGG

LTG_D0033 EF1a CD33_4 VH TNFRSF19 H_TM_CD28z amino acid sequence

MLLLVTSLLLCELPHPAFLLIPEVQLVESGGGLVQPGGSLRLSCAASGFTFSSYGMSWVR
QAPRQGLEWVANIKQDGSEKYYADSVKGRFTISRDNSKNTLYLQMNSLRAEDTATYYCAK
ENVDWGQGTLVTVSSAAAVGFQDMECVPCGDPPPPYEPHCASKVNLVKIASTASSPRDTA
LAAVICSALATVLLALLILCVIRSKRSRLLHSDYMNMTPRRPGPTRKHYQPYAPPRDFAA
YRSRVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR

FIGURE 12B

LTG_D0034 (Efla_CD33_4 VH TNFRSF19 H_TM_4-1BBz) nucleotide sequence
ATGCTGCTGCTGGTGACCAGCCTGCTGCTGTGCGAACTGCCGCATCCGGCGTTTCTGCTG
ATTCCGGAGGTGCAGCTGGTGGAGTCTGGGGGAGGCTTGGTACAGCCTGGAGGGTCCCTG
AGACTCTCCTGTGCAGCCTCTGGATTCACCTTCAGTAGCTATGGCATGAGCTGGGTCCGC
CAGGCTCCAAGACAAGGGCTTGAGTGGGTGGCCAACATAAAGCAAGATGGAAGTGAGAAA
TACTATGCGGACTCAGTGAAGGGCCGATTCACCATCTCCAGAGACAATTCCAAGAACACG
CTGTATCTGCAAATGAACAGCCTGAGAGCCGAGGACACAGCCACGTATTACTGTGCGAAA
GAAAATGTGGACTGGGGCCAGGGCACCCTGGTCACCGTCTCCTCAGCGGCCGCAGTCGGA
TTCCAAGACATGGAATGCGTGCCCTGCGGCGACCCGCCACCTCCTTACGAGCCGCACTGC
GCATCGAAGGTCAACCTCGTGAAGATCGCGAGCACCGCGTCCTCACCCCGGGATACTGCT
CTGGCCGCCGTGATTTGTTCCGCCTTGGCCACCGTGCTTCTGGCCCTGCTGATCCTCTGT
GTGATCAAGAGGGGCCGGAAGAAGCTGCTTTACATCTTCAAGCAGCCGTTCATGCGGCCC
GTGCAGACGACTCAGGAAGAGGACGGATGCTCGTGCAGATTCCCTGAGGAGGAAGAGGGG
GGATGCGAACTGAGAGTGAAGTTCAGCCGCTCAGCCGATGCACCGGCCTACCAGCAGGGA
CAGAACCAGCTCTACAACGAGCTCAACCTGGGTCGGCGGGAAGAATATGACGTGCTGGAC
AAACGGCGCGGCAGAGATCCGGAGATGGGGGGAAAGCCGAGGAGGAAGAACCCTCAAGAG
GGCCTGTACAACGAACTGCAGAAGGACAAGATGGCGGAAGCCTACTCCGAGATCGGCATG
AAGGGAGAACGCCGGAGAGGGAAGGGTCATGACGGACTGTACCAGGGCCTGTCAACTGCC
ACTAAGGACACTTACGATGCGCTCCATATGCAAGCTTTGCCCCGCGG LTG_D0034 (Efla_CD33_4 VH TNFRSF19 H_TM_4-1BBz) amino acid seq.
MLLLVTSLLLCELPHPAFLLIPEVQLVESGGGLVQPGGSLRLSCAASGFTFSSYGMSWVR
QAPRQGLEWVANIKQDGSEKYYADSVKGRFTISRDNSKNTLYLQMNSLRAEDTATYYCAK
ENVDWGQGTLVTVSSAAAVGFQDMECVPCGDPPPPYEPHCASKVNLVKIASTASSPRDTA
LAAVICSALATVLLALLILCVIKRGRKKLLYIFKQPFMRPVQTTQEEDGCSCRFPEEEEG
GCELRVKFSRSADAPAYQQGQNQLYNELNLGRREEYDVLDKRRGRDPEMGGKPRRKNPQE
GLYNELQKDKMAEAYSEIGMKGERRRGKGHDGLYQGLSTATKDTYDALHMQALPPR

FIGURE 12C

LTG_ D0015 CD33_4VH CD8 BBz T2A tEGFR nucleotide sequence

ATGCTGCTGCTGGTGACCAGCCTGCTGCTGTGCGAACTGCCGCATCCGGC
GTTTCTGCTGATTCCGGAGGTGCAGCTGGTGGAGTCTGGGGGAGGCTTGG
TACAGCCTGGAGGGTCCCTGAGACTCTCCTGTGCAGCCTCTGGATTCACCT
TCAGTAGCTATGGCATGAGCTGGGTCCGCCAGGCTCCAAGACAAGGGCTT
GAGTGGGTGGCCAACATAAAGCAAGATGGAAGTGAGAAATACTATGCGG
ACTCAGTGAAGGGCCGATTCACCATCTCCAGAGACAATTCCAAGAACACG
CTGTATCTGCAAATGAACAGCCTGAGAGCCGAGGACACAGCCACGTATTA
CTGTGCGAAAGAAATGTGGACTGGGGCCAGGGCACCCTGGTCACCGTCT
CCTCAGCGGCCGCAACTACCACCCCTGCCCCTCGGCCGCCGACTCCGGCC
CCAACCATCGCAAGCCAACCCCTCTCCTTGCGCCCCGAAGCTTGCCGCCC
GGCCGCGGGTGGAGCCGTGCATACCCGGGGGCTGGACTTTGCCTGCGATA
TCTACATTTGGGCCCCGCTGGCCGGCACTTGCGGCGTGCTCCTGCTGTCGC
TGGTCATCACCCTTTACTGCAAGAGGGGCCGGAAGAAGCTGCTTTACATC
TTCAAGCAGCCGTTCATGCGGCCCGTGCAGACGACTCAGGAAGAGGACGG
ATGCTCGTGCAGATTCCCTGAGGAGGAAGAGGGGGGATGCGAACTGCGC
GTCAAGTTCTCACGGTCCGCCGACGCCCCGCATATCAACAGGGCCAGAA
TCAGCTCTACAACGAGCTGAACCTGGGAAGGAGAGAGGAGTACGACGTG
CTGGACAAGCGACGCGGACGCGACCCGGAGATGGGGGGGAAACCACGGC
GGAAAAACCCTCAGGAAGGACTGTACAACGAACTCCAGAAAGACAAGAT
GGCGGAAGCCTACTCAGAAATCGGGATGAAGGGAGAGCGGAGGAGGGGA
AAGGGTCACGACGGGCTGTACCAGGGACTGAGCACCGCCACTAAGGATA
CCTACGATGCCTTGCATATGCAAGCACTCCCACCCCGGTCTAGAGCTAAA
CGCTCTGGGTCTGGTGAAGGACGAGGTAGCCTTCTTACGTGCGGAGACGT
GGAGGAAAACCCAGGACCCCGAGCCAAACGAATGCTGCTGCTTGTTACAA
GCCTTTTGCTCTGCGAACTCCCCCATCCAGCTTTTCTCCTGATTCCAAGGA
AGGTTTGCAATGGAATCGGTATAGGGGAGTTTAAGGATTCACTTAGCATA
AACGCTACTAATATTAAACACTTCAAAAACTGTACGAGTATAAGTGGAGA
TCTTCACATTTTGCCGGTTGCATTCCGAGGCGATTCATTCACCCACACGCC
ACCGCTTGACCCACAAGAATTGGATATTCTTAAAACCGTTAAAGAAATAA
CGGGGTTTTTGCTCATTCAAGCGTGGCCAGAAAATCGCACTGACCTCCAT

FIGURE 12D

```
GCTTTCGAGAACCTGGAGATTATAAGAGGACGAACTAAGCAGCATGGTCA
ATTCTCCCTTGCTGTGGTCAGCCTGAACATCACCAGTCTTGGTTTGCGGTC
CCTCAAGGAAATTTCAGATGGAGATGTCATCATAAGCGGCAACAAGAATT
TGTGCTATGCAAATACCATAAACTGGAAAAAACTGTTTGGCACTTCCGGC
CAGAAAACCAAGATTATTTCAAATCGGGGTGAGAACAGCTGCAAAGCCA
CCGGCCAGGTTTGTCATGCCTTGTGCTCTCCGGAAGGCTGTTGGGGGCCA
GAACCCAGGGACTGCGTCAGTTGCAGAAACGTCTCAAGAGGCCGCGAAT
GCGTTGACAAGTGTAACCTCCTTGAGGGTGAGCCACGAGAGTTTGTTGAG
AACAGCGAGTGTATACAATGTCACCCTGAATGTTTGCCCCAGGCTATGAA
TATAACCTGCACAGGCCGCGGGCCTGATAACTGCATCCAGTGTGCTCATT
ACATAGATGGACCTCACTGTGTGAAAACCTGCCCGGCCGGAGTTATGGGA
GAAAACAACACTCTGGTGTGGAAATACGCTGATGCAGGCCACGTGTGCCA
CCTTTGTCACCCGAATTGTACATATGGGTGTACCGGTCCTGGACTTGAAGG
TTGCCCTACCAATGGCCCTAAAATACCCAGTATCGCAACTGGCATGGTAG
GCGCTCTTCTCTTGCTCTTGGTAGTTGCTCTCGGCATAGGTCTTTTATG
```

FIGURE 12D, continued

LTG_D0015 CD33_4VH CD8 BBz T2A tEGFR amino acid sequence

MLLLVTSLLLCELPHPAFLLIPEVQLVESGGGLVQPGGSLRLSCAASGFTFSSY
GMSWVRQAPRQGLEWVANIKQDGSEKYYADSVKGRFTISRDNSKNTLYLQ
MNSLRAEDTATYYCAKENVDWGQGTLVTVSSAAATTTPAPRPPTPAPTIASQ
PLSLRPEACRPAAGGAVHTRGLDFACDIYIWAPLAGTCGVLLLSLVITLYCKR
GRKKLLYIFKQPFMRPVQTTQEEDGCSCRFPEEEEGGCELRVKFSRSADAPAY
QQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPRS
RAKRSGSGEGRGSLLTCGDVEENPGPRAKRMLLLVTSLLLCELPHPAFLLIPR
KVCNGIGIGEFKDSLSINATNIKHFKNCTSISGDLHILPVAFRGDSFTHTPPLDP
QELDILKTVKEITGFLLIQAWPENRTDLHAFENLEIIRGRTKQHGQFSLAVVSL
NITSLGLRSLKEISDGDVIISGNKNLCYANTINWKKLFGTSGQKTKIISNRGENS
CKATGQVCHALCSPEGCWGPEPRDCVSCRNVSRGRECVDKCNLLEGEPREF
VENSECIQCHPECLPQAMNITCTGRGPDNCIQCAHYIDGPHCVKTCPAGVMG
ENNTLVWKYADAGHVCHLCHPNCTYGCTGPGLEGCPTNGPKIPSIATGMVG
ALLLLLVVALGIGLFM

FIGURE 12D, continued

LTG_D0016 CD33_4VH CD8 28z T2A tEGFR nucleotide sequence

ATGCTGCTGCTGGTGACCAGCCTGCTGCTGTGCGAACTGCCGCATCCGGC
GTTTCTGCTGATTCCGGAGGTGCAGCTGGTGGAGTCTGGGGGAGGCTTGG
TACAGCCTGGAGGGTCCCTGAGACTCTCCTGTGCAGCCTCTGGATTCACCT
TCAGTAGCTATGGCATGAGCTGGGTCCGCCAGGCTCCAAGACAAGGGCTT
GAGTGGGTGGCCAACATAAAGCAAGATGGAAGTGAGAAATACTATGCGG
ACTCAGTGAAGGGCCGATTCACCATCTCCAGAGACAATTCCAAGAACACG
CTGTATCTGCAAATGAACAGCCTGAGAGCCGAGGACACAGCCACGTATTA
CTGTGCGAAAGAAAATGTGGACTGGGGCCAGGGCACCCTGGTCACCGTCT
CCTCAGCGGCCGCGACTACCACTCCTGCACCACGGCCACCTACCCCAGCC
CCCACCATTGCAAGCCAGCCACTTTCACTGCGCCCCGAAGCGTGTAGACC
AGCTGCTGGAGGAGCCGTGCATACCCGAGGGCTGGACTTCGCCTGTGACA
TCTACATCTGGGCCCCATTGGCTGGAACTTGCGGCGTGCTGCTCTTGTCTC
TGGTCATTACCCTGTACTGCCGGTCGAAGAGGTCCAGACTCTTGCACTCCG
ACTACATGAACATGACTCCTAGAAGGCCCGGACCCACTAGAAAGCACTAC
CAGCCGTACGCCCCTCCTCGGGATTTCGCCGCATACCGGTCCAGAGTGAA
GTTCAGCCGCTCAGCCGATGCACCGGCCTACCAGCAGGGACAGAACCAGC
TCTACAACGAGCTCAACCTGGGTCGGCGGGAAGAATATGACGTGCTGGAC
AAACGGCGCGGCAGAGATCCGGAGATGGGGGGAAAGCCGAGGAGGAAG
AACCCTCAAGAGGGCCTGTACAACGAACTGCAGAAGGACAAGATGGCGG
AAGCCTACTCCGAGATCGGCATGAAGGGAGAACGCCGGAGAGGGAAGGG
TCATGACGGACTGTACCAGGGCCTGTCAACTGCCACTAAGGACACTTACG
ATGCGCTCCATATGCAAGCTTTGCCCCGCGGAGAGCTAAACGCTCTGGG
TCTGGTGAAGGACGAGGTAGCCTTCTTACGTGCGGAGACGTGGAGGAAAA
CCCAGGACCCCGAGCCAAACGAATGCTGCTGCTTGTTACAAGCCTTTTGCT
CTGCGAACTCCCCCATCCAGCTTTTCTCCTGATTCCAAGGAAGGTTTGCAA
TGGAATCGGTATAGGGGAGTTTAAGGATTCACTTAGCATAAACGCTACTA
ATATTAAACACTTCAAAAACTGTACGAGTATAAGTGGAGATCTTCACATTT
TGCCGGTTGCATTCCGAGGCGATTCATTCACCCACACGCCACCGCTTGACC
CACAAGAATTGGATATTCTTAAAACCGTTAAAGAAATAACGGGGTTTTG
CTCATTCAAGCGTGGCCAGAAAATCGCACTGACCTCCATGCTTTCGAGAA

FIGURE 12E

CCTGGAGATTATAAGAGGACGAACTAAGCAGCATGGTCAATTCTCCCTTG
CTGTGGTCAGCCTGAACATCACCAGTCTTGGTTTGCGGTCCCTCAAGGAA
ATTTCAGATGGAGATGTCATCATAAGCGGCAACAAGAATTTGTGCTATGC
AAATACCATAAACTGGAAAAAACTGTTTGGCACTTCCGGCCAGAAAACCA
AGATTATTTCAAATCGGGGTGAGAACAGCTGCAAAGCCACCGGCCAGGTT
TGTCATGCCTTGTGCTCTCCGGAAGGCTGTTGGGGGCCAGAACCCAGGGA
CTGCGTCAGTTGCAGAAACGTCTCAAGAGGCCGCGAATGCGTTGACAAGT
GTAACCTCCTTGAGGGTGAGCCACGAGAGTTTGTTGAGAACAGCGAGTGT
ATACAATGTCACCCTGAATGTTTGCCCCAGGCTATGAATATAACCTGCAC
AGGCCGCGGGCCTGATAACTGCATCCAGTGTGCTCATTACATAGATGGAC
CTCACTGTGTGAAAACCTGCCCGGCCGGAGTTATGGGAGAAAACAACACT
CTGGTGTGGAAATACGCTGATGCAGGCCACGTGTGCCACCTTTGTCACCC
GAATTGTACATATGGGTGTACCGGTCCTGGACTTGAAGGTTGCCCTACCA
ATGGCCCTAAAATACCCAGTATCGCAACTGGCATGGTAGGCGCTCTTCTCT
TGCTCTTGGTAGTTGCTCTCGGCATAGGTCTTTTATG

LTG_D0016 CD33_4VH CD8 28z T2A tEGFR amino acid sequence
MLLLVTSLLLCELPHPAFLLIPEVQLVESGGGLVQPGGSLRLSCAASGFTFSSY
GMSWVRQAPRQGLEWVANIKQDGSEKYYADSVKGRFTISRDNSKNTLYLQ
MNSLRAEDTATYYCAKENVDWGQGTLVTVSSAAATTTPAPRPPTPAPTIASQ
PLSLRPEACRPAAGGAVHTRGLDFACDIYIWAPLAGTCGVLLLSLVITLYCRS
KRSRLLHSDYMNMTPRRPGPTRKHYQPYAPPRDFAAYRSRVKFSRSADAPA
YQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR
RAKRSGSGEGRGSLLTCGDVEENPGPRAKRMLLLVTSLLLCELPHPAFLLIPR
KVCNGIGIGEFKDSLSINATNIKHFKNCTSISGDLHILPVAFRGDSFTHTPPLDP
QELDILKTVKEITGFLLIQAWPENRTDLHAFENLEIIRGRTKQHGQFSLAVVSL
NITSLGLRSLKEISDGDVIISGNKNLCYANTINWKKLFGTSGQKTKIISNRGENS
CKATGQVCHALCSPEGCWGPEPRDCVSCRNVSRGRECVDKCNLLEGEPREF
VENSECIQCHPECLPQAMNITCTGRGPDNCIQCAHYIDGPHCVKTCPAGVMG
ENNTLVWKYADAGHVCHLCHPNCTYGCTGPGLEGCPTNGPKIPSIATGMVG
ALLLLLVVALGIGLFM

FIGURE 12E, continued

LTG_D0035 (Ef1a_CD33_4 VH H CH2 CH3 IgG4_CD8TM_CD28z) nucleotide sequence

ATGCTGCTGCTGGTGACCAGCCTGCTGCTGTGCGAACTGCCGCATCCGGCGTTTC
TGCTGATTCCGGAGGTGCAGCTGGTGGAGTCTGGGGGAGGCTTGGTACAGCCTG
GAGGGTCCCTGAGACTCTCCTGTGCAGCCTCTGGATTCACCTTCAGTAGCTATGG
CATGAGCTGGGTCCGCCAGGCTCCAAGACAAGGGCTTGAGTGGGTGGCCAACAT
AAAGCAAGATGGAAGTGAGAAATACTATGCGGACTCAGTGAAGGGCCGATTCAC
CATCTCCAGAGACAATTCCAAGAACACGCTGTATCTGCAAATGAACAGCCTGAG
AGCCGAGGACACAGCCACGTATTACTGTGCGAAGAAATGTGGACTGGGGCCA
GGGCACCCTGGTCACCGTCTCCTCAGCGGCCGCAGAGAGCAAATACGGGCCGCC
ATGTCCCCGTGTCCGGCACCACCAGTTGCTGGCCCTAGTGTCTTCTTGTTCCCTC
CCAAGCCCAAAGACACCTTGATGATTTCCAGAACTCCTGAGGTTACCTGCGTTGT
CGTAGATGTTTCTCAGGAGGACCCAGAGGTCCAATTTAACTGGTACGTTGATGGG
GTGGAAGTTCACAATGCGAAGACAAAGCCGCGGGAAGAACAATTTCAGTCCACT
TACCGGGTTGTCAGCGTTCTGACGGTATTGCATCAAGACTGGCTTAATGGAAGG
AATATAAGTGTAAGGTGTCCAACAAAGGTTTGCCGAGCAGTATTGAGAAGACCA
TATCAAAGGCGAAGGGGCAGCCGCGCGAGCCACAAGTTTACACTTTGCCGCCAT
CTCAAGAGGAAATGACTAAAAACCAGGTATCCTTGACATGCCTCGTAAAAGGAT
TTTATCCATCTGATATTGCTGTGGAATGGGAGTCTAACGGGCAGCCGGAAAATAA
TTACAAAACTACACCACCTGTGCTCGATTCAGATGGAAGTTTCTTCCTTTACAGT
AGACTTACGGTGGACAAATCTAGGTGGCAGGAAGGGAATGTGTTTAGTTGTAGT
GTAATGCACGAGGCACTTCATAACCACTATACACAGAAGTCACTGAGTTTGAGTC
TTGGCAAAATCTACATCTGGGCGCCCTTGGCCGGGACTTGTGGGGTCCTTCTCCT
GTCACTGGTTATCACCCTTTACTGCCGGTCGAAGAGGTCCAGACTCTTGCACTCC
GACTACATGAACATGACTCCTAGAAGGCCCGGACCCACTAGAAAGCACTACCAG
CCGTACGCCCCTCCTCGGGATTTCGCCGCATACCGGTCCAGAGTGAAGTTCAGCC
GCTCAGCCGATGCACCGGCCTACCAGCAGGGACAGAACCAGCTCTACAACGAGC
TCAACCTGGGTCGGCGGGAAGAATATGACGTGCTGGACAAACGGCGCGGCAGAG
ATCCGGAGATGGGGGGAAAGCCGAGGAGGAAGAACCCTCAAGAGGGCCTGTAC
AACGAACTGCAGAAGGACAAGATGGCGGAAGCCTACTCCGAGATCGGCATGAA
GGGAGAACGCCGGAGAGGGAAGGGTCATGACGGACTGTACCAGGGCCTGTCAA
CTGCCACTAAGGACACTTACGATGCGCTCCATATGCAAGCTTTGCCCCCGCGG

FIGURE 12F

LTG_D0035 (Efla_CD33_4 VH H CH2 CH3 IgG4_CD8TM_CD28z) amino acid sequence

MLLLVTSLLLCELPHPAFLLIPEVQLVESGGGLVQPGGSLRLSCAASGFTFSSY
GMSWVRQAPRQGLEWVANIKQDGSEKYYADSVKGRFTISRDNSKNTLYLQ
MNSLRAEDTATYYCAKENVDWGQGTLVTVSSAAAESKYGPPCPPCPAPPVA
GPSVFLFPPKPKDTLMISRTPEVTCVVVDVSQEDPEVQFNWYVDGVEVHNAK
TKPREEQFQSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLS
LGKIYIWAPLAGTCGVLLLSLVITLYCRSKRSRLLHSDYMNMTPRRPGPTRKH
YQPYAPPRDFAAYRSRVKFSRSADAPAYQQGQNQLYNELNLGRREEYDVLD
KRRGRDPEMGGKPRRKNPQEGLYNELQKDKMAEAYSEIGMKGERRRGKGH
DGLYQGLSTATKDTYDALHMQALPPR

FIGURE 12F, continued

SEQUENCE LISTING

<160> NUMBER OF SEQ ID NOS: 88

<210> SEQ ID NO 1
<211> LENGTH: 357
<212> TYPE: DNA
<213> ORGANISM: Homo sapiens

<400> SEQUENCE: 1

```
gaggtgcagc tggtggagtc tgggggaggc ttggtacagc ctggagggtc cctgagactc      60
tcctgtgcag cctctggatt caccttcagt agctatggca tgagctgggt ccgccaggct     120
ccaaggaagg gcctggagtg gattgggaa atcaatcata gtggaagcac caactacaac      180
ccgtccctca agagtcgagt caccatctcc agagacaatt ccaagaacac gctgtatctg     240
caaatgaaca gcctgagagc cgaggacaca gccacgtatt actgtgcgag acccctcaac     300
tactactact actacatgga cgtctggggc aaagggacca cggtcaccgt ctcctca        357
```

<210> SEQ ID NO 2
<211> LENGTH: 119
<212> TYPE: PRT
<213> ORGANISM: Homo sapiens

<400> SEQUENCE: 2

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Arg Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Ser Leu Arg Ala Glu Asp Thr Ala Thr Tyr Tyr Cys Ala
                85                  90                  95

Arg Pro Leu Asn Tyr Tyr Tyr Tyr Tyr Met Asp Val Trp Gly Lys Gly
            100                 105                 110

Thr Thr Val Thr Val Ser Ser
        115
```

<210> SEQ ID NO 3
<211> LENGTH: 339
<212> TYPE: DNA
<213> ORGANISM: Homo sapiens

<400> SEQUENCE: 3

```
gaggtgcagc tggtggagtc tgggggaggc ttggtacagc ctggagggtc cctgagactc      60
tcctgtgcag cctctggatt caccttcagt agctatggca tgagctgggt ccgccaggct     120
ccaagacaag ggcttgagtg ggtggccaac ataaagcaag atggaagtga aaatactat      180
gcggactcag tgaagggccg attcaccatc tccagagaca attccaagaa cacgctgtat     240
ctgcaaatga acagcctgag agccgaggac acagccacgt attactgtgc gaaagaaaat     300
gtggactggg gccagggcac cctggtcacc gtctcctca                            339
```

<210> SEQ ID NO 4
<211> LENGTH: 113
<212> TYPE: PRT
<213> ORGANISM: Homo sapiens

<400> SEQUENCE: 4

```
Glu Val Gln Leu Val Glu Ser Gly Gly Gly Leu Val Gln Pro Gly Gly
 1               5                  10                  15
```

Ser Leu Arg Leu Ser Cys Ala Ala Ser Gly Phe Thr Phe Ser Ser Tyr
            20                  25                  30

Gly Met Ser Trp Val Arg Gln Ala Pro Arg Gln Gly Leu Glu Trp Val
        35                  40                  45

Ala Asn Ile Lys Gln Asp Gly Ser Glu Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Glu Asn Val Asp Trp Gly Gln Gly Thr Leu Val Thr Val Ser
            100                 105                 110

Ser

<210> SEQ ID NO 5
<211> LENGTH: 747
<212> TYPE: DNA
<213> ORGANISM: Homo sapiens

<400> SEQUENCE: 5
caggtgcagc tggtgcaatc tggggcagag gtgaaaaagc ccggggagtc tctgaggatc      60
tcctgtaagg gttctggatt cagttttccc acctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcagc accgcctac     240 ctgcagtgga gcagcctgaa ggcctcggac accgccatgt attactgtgc gagactagtt     300
ggagatggct acaatacggg ggcttttgat atctggggcc aagggacaat ggtcaccgtc     360
tcttcaggag gtggcgggtc tggtggtggc ggtagcggtg gtggcggatc cgatattgtg     420
atgacccaca ctccactctc tctgtccgtc acccctggac agccggcctc catctcctgc     480
aagtctagtc agagcctcct gcatagtaat ggaaagacct atttgtattg gtacctgcag     540
aagccaggcc agcctccaca gctcctgatc tatggagctt ccaaccggtt ctctggagtg     600
ccagacaggt tcagtggcag cgggtcaggg acagatttca cactgaaaat cagccgggtg     660
gaggctgagg atgttggggt ttattactgc atgcaaagta cagcttccta tcaccttc     720 ggccaaggga cacgactgga gattaaa                                         747

<210> SEQ ID NO 6
<211> LENGTH: 249
<212> TYPE: PRT
<213> ORGANISM: Homo sapiens

<400> SEQUENCE: 6

Gln Val Gln Leu Val Gln Ser Gly Ala Glu Val Lys Lys Pro Gly Glu
1               5                   10                  15

Ser Leu Arg Ile Ser Cys Lys Gly Ser Gly Phe Ser Phe Pro Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                    85                  90                  95

Ala Arg Leu Val Gly Asp Gly Tyr Asn Thr Gly Ala Phe Asp Ile Trp
                100                 105                 110

Gly Gln Gly Thr Met Val Thr Val Ser Gly Gly Gly Gly Ser Gly
            115                 120                 125

Gly Gly Gly Ser Gly Gly Gly Ser Asp Ile Val Met Thr His Thr
        130                 135                 140

Pro Leu Ser Leu Ser Val Thr Pro Gly Gln Pro Ala Ser Ile Ser Cys
145                 150                 155                 160

Lys Ser Ser Gln Ser Leu Leu His Ser Asn Gly Lys Thr Tyr Leu Tyr
                165                 170                 175

Trp Tyr Leu Gln Lys Pro Gly Gln Pro Pro Gln Leu Leu Ile Tyr Gly
                180                 185                 190

Ala Ser Asn Arg Phe Ser Gly Val Pro Asp Arg Phe Ser Gly Ser Gly
                195                 200                 205

Ser Gly Thr Asp Phe Thr Leu Lys Ile Ser Arg Val Glu Ala Glu Asp
            210                 215                 220

Val Gly Val Tyr Tyr Cys Met Gln Ser Ile Gln Leu Pro Ile Thr Phe
225                 230                 235                 240

Gly Gln Gly Thr Arg Leu Glu Ile Lys
                245

<210> SEQ ID NO 7
<211> LENGTH: 759
<212> TYPE: DNA
<213> ORGANISM: Homo sapiens

<400> SEQUENCE: 7
caggtacagc tgcagcagtc aggtccagga ctggtgaagc cctcgcagac cctctcactc        60
acctgtgcca tctccgggga cagtgtctct agcaacactg ctgcttggaa ctggatcagg       120
cagtccccat cgagaggcct tgagtggctg gaaggacat actacaggtc caagtggtat       180
aatgattatg cagtccctgt gaaaagtcga ataaccatca cccagacac atccaagaac       240
cagttctccc tgcagctgaa ctctgtgact cccgaggaca cggctgtgta ttactgtgca       300
agagaaacgt attactatgg ttcggggagt tattgggatg cttttgatat ctggggccaa       360
gggaccacgg tcaccgtctc ctcaggaggt ggcgggtctg gtagtggcgg tagcggtggt       420
ggcggatccc agtctgtcgt gacgcagccg ccctcagtgt ctgcggcccc aggacagaag       480
gtcaccatct cctgctctgg aagcagctcc aacattggga ataattatgt atcctggtac       540
cagcagctcc caggcacggc ccccaaactc ttcatctata aaataatca gcggccctca       600
gaggtccctg accgattctc tggctccaag tctggcacct cagcctccct ggccatcagt       660
gggctccagt ctgacgatga ggctgactac tactgtgcag catgggatga caggctgaat       720
ggatatgtct tcggaactgg gaccaaggtc accgtccta                              759

<210> SEQ ID NO 8
<211> LENGTH: 253
<212> TYPE: PRT
<213> ORGANISM: Homo sapiens

<400> SEQUENCE: 8

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Thr Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Pro Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Thr Tyr Tyr Gly Ser Gly Ser Tyr Trp
            100                 105                 110

Asp Ala Phe Asp Ile Trp Gly Gln Gly Thr Thr Val Thr Val Ser Ser
        115                 120                 125

Gly Gly Gly Gly Ser Gly Gly Gly Ser Gly Gly Gly Gly Ser Gln
            130                 135                 140

Ser Val Val Thr Gln Pro Pro Ser Val Ser Ala Ala Pro Gly Gln Lys
145                 150                 155                 160

Val Thr Ile Ser Cys Ser Gly Ser Ser Ser Asn Ile Gly Asn Asn Tyr
                165                 170                 175

Val Ser Trp Tyr Gln Gln Leu Pro Gly Thr Ala Pro Lys Leu Phe Ile
            180                 185                 190

Tyr Lys Asn Asn Gln Arg Pro Ser Glu Val Pro Asp Arg Phe Ser Gly
        195                 200                 205

Ser Lys Ser Gly Thr Ser Ala Ser Leu Ala Ile Ser Gly Leu Gln Ser
210                 215                 220

Asp Asp Glu Ala Asp Tyr Tyr Cys Ala Ala Trp Asp Asp Arg Leu Asn
225                 230                 235                 240

Gly Tyr Val Phe Gly Thr Gly Thr Lys Val Thr Val Leu
            245                 250

<210> SEQ ID NO 9
<211> LENGTH: 741
<212> TYPE: DNA
<213> ORGANISM: Homo sapiens

<400> SEQUENCE: 9
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggagggacat actacaggtc caagtggtat   180
aatgattatg cagtatctgt gaaaagtcga ataattatca acgcagacac atcgaagaac   240
cagttctccc tgcagctgaa ctctgtgact cccgaggaca cggctgtgta ttactgtgcg   300 agggatatt actatgatag taccgactgg ttcgacccct ggggccaggg aaccctggtc   360
accgtctcct caggaggtgg cgggtctggt ggtggcggta gcgtggtgg cggatcctct   420 tctgagctga ctcaggaccc aactgtgtct gtggccttgg acagacagt caggatcaca   480 tgccaaggag acagcctcag aagctattat gcaagctggt accagcagaa gccaggacag   540
gcccctgtac ttgtcatcta tggtaaaaac aaccggccct cagggatccc agaccgattc   600
tctggctcca gctcaggaaa cacagcttcc ttgaccatca ctgggctca ggcggaagat   660 gaggctgact attactgttc ctcccgggac ggcagtggtc atccatatct cttcggacct   720
gggaccaagg tcaccgttct t                                              741

<210> SEQ ID NO 10
<211> LENGTH: 247
<212> TYPE: PRT
<213> ORGANISM: Homo sapiens

<400> SEQUENCE: 10

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Gly Thr Tyr Tyr Arg Ser Lys Trp Tyr Asn Asp Tyr Ala
    50                  55                  60

Val Ser Val Lys Ser Arg Ile Ile Ile Asn Ala Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Tyr Tyr Tyr Asp Ser Thr Asp Trp Phe Asp
            100                 105                 110

Pro Trp Gly Gln Gly Thr Leu Val Thr Val Ser Ser Gly Gly Gly Gly
        115                 120                 125

Ser Gly Gly Gly Gly Ser Gly Gly Gly Gly Ser Ser Glu Leu Thr
    130                 135                 140

Gln Asp Pro Thr Val Ser Val Ala Leu Gly Gln Thr Val Arg Ile Thr
145                 150                 155                 160

Cys Gln Gly Asp Ser Leu Arg Ser Tyr Tyr Ala Ser Trp Tyr Gln Gln
                165                 170                 175

Lys Pro Gly Gln Ala Pro Val Leu Val Ile Tyr Gly Lys Asn Asn Arg
            180                 185                 190

Pro Ser Gly Ile Pro Asp Arg Phe Ser Gly Ser Ser Ser Gly Asn Thr
        195                 200                 205

Ala Ser Leu Thr Ile Thr Gly Ala Gln Ala Glu Asp Glu Ala Asp Tyr
    210                 215                 220

Tyr Cys Ser Ser Arg Asp Gly Ser Gly His Pro Tyr Leu Phe Gly Pro
225                 230                 235                 240

Gly Thr Lys Val Thr Val Leu
                245
```

<210> SEQ ID NO 11
<211> LENGTH: 735
<212> TYPE: DNA
<213> ORGANISM: Homo sapiens

<400> SEQUENCE: 11

```
gaggtccagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac     240 ctgcagtgga gcagcctgaa ggcctcggac accgccatgt attactgtgc gagactgact     300
acggctgggg gtatggacgt ctggggccaa gggaccacgg tcaccgtctc ctcaggaggt     360
ggcgggtctg gtggtggcgg tagcggtggt ggcggatccg aaattgtgct gactcagtct     420
ccactctccc tgcccgtcac ccttggacag ccggcctcca tctcctgcag gtctagtcaa     480
```

-continued

```
agcctcgtac acagtgatgg aaacacctac ttgagttggc ttcaccagag gccaggccag    540
cctccaagac tcctaatgta taagatttct aaccggttct ctggggtcac agacagattc    600
agtggcagcg ggtcagggac agatttcaca ctgaaaatca gccgggtgga ggctgaggat    660
gttggggttt attactgcat gcaaggtata cacctaccgc tcactttcgg cggagggacc    720
aagctggaga tcaaa                                                     735
```

<210> SEQ ID NO 12
<211> LENGTH: 245
<212> TYPE: PRT
<213> ORGANISM: Homo sapiens

<400> SEQUENCE: 12

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Thr Thr Ala Gly Gly Met Asp Val Trp Gly Gln Gly Thr
            100                 105                 110

Thr Val Thr Val Ser Ser Gly Gly Gly Ser Gly Gly Gly Ser
        115                 120                 125

Gly Gly Gly Gly Ser Glu Ile Val Leu Thr Gln Ser Pro Leu Ser Leu
    130                 135                 140

Pro Val Thr Leu Gly Gln Pro Ala Ser Ile Ser Cys Arg Ser Ser Gln
145                 150                 155                 160

Ser Leu Val His Ser Asp Gly Asn Thr Tyr Leu Ser Trp Leu His Gln
                165                 170                 175

Arg Pro Gly Gln Pro Pro Arg Leu Leu Met Tyr Lys Ile Ser Asn Arg
            180                 185                 190

Phe Ser Gly Val Thr Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Met Gln Gly Ile His Leu Pro Leu Thr Phe Gly Gly Gly Thr
225                 230                 235                 240

Lys Leu Glu Ile Lys
            245

<210> SEQ ID NO 13
<211> LENGTH: 66
<212> TYPE: DNA
<213> ORGANISM: Artificial
<220> FEATURE:
<223> OTHER INFORMATION: Leader/signal peptide sequence

<400> SEQUENCE: 13

```
atgctgctgc tggtgaccag cctgctgctg tgcgaactgc cgcatccggc gtttctgctg    60
attccg                                                                66
```

<210> SEQ ID NO 14
<211> LENGTH: 22
<212> TYPE: PRT
<213> ORGANISM: Artificial
<220> FEATURE:
<223> OTHER INFORMATION: Leader/signal peptide sequence

<400> SEQUENCE: 14

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 15
<211> LENGTH: 1101
<212> TYPE: DNA
<213> ORGANISM: Artificial
<220> FEATURE:
<223> OTHER INFORMATION: LTG 1905_(EF1a- VH-2 CD33-CD8 TM-41BB-CD3 zeta)

<400> SEQUENCE: 15

```
atgctgctgc tggtgaccag cctgctgctg tgcgaactgc cgcatccggc gtttctgctg      60
attccgagg tgcagctggt ggagtctggg ggaggcttgg tacagcctgg agggtccctg     120
agactctcct gtgcagcctc tggattcacc ttcagtagct atggcatgag ctgggtccgc     180
caggctccaa ggaagggcct ggagtggatt ggggaaatca atcatagtgg aagcaccaac     240
tacaacccgt ccctcaagag tcgagtcacc atctccagag acaattccaa gaacacgctg     300
tatctgcaaa tgaacagcct gagagccgag gacacagcca cgtattactg tgcgagaccc     360
ctcaactact actactacta catggacgtc tggggcaaag ggaccacggt caccgtctcc     420
tcagcggccg caactaccac ccctgcccct cggccgccga ctccggcccc aaccatcgca     480
agccaacccc tctccttgcg ccccgaagct tgccgcccgg ccgcgggtgg agccgtgcat     540
acccgggggc tggactttgc ctgcgatatc tacatttggg ccccgctggc cggcacttgc     600
ggcgtgctcc tgctgtcgct ggtcatcacc ctttactgca gaggggccg aagaagctg      660
ctttacatct tcaagcagcc gttcatgcgg cccgtgcaga cgactcagga agaggacgga     720
tgctcgtgca gattccctga ggaggaagag ggggatgcg aactgcgcgt caagttctca     780
cggtccgccg acgccccgc atatcaacag gccagaatc agctctacaa cgagctgaac     840
ctgggaagga gagaggtta cgacgtgctg gacaagcgac gcggacgcga cccggagatg     900
gggggaaac cacggcggaa aaaccctcag gaaggactgt acaacgaact ccagaaagac     960
aagatggcgg aagcctactc agaaatcggg atgaagggag agcggaggag ggaaagggt   1020
cacgacgggc tgtaccaggg actgagcacc gccactaagg atacctacga tgccttgcat   1080
atgcaagcac tcccaccccg g                                             1101
```

<210> SEQ ID NO 16
<211> LENGTH: 367
<212> TYPE: PRT
<213> ORGANISM: Artificial
<220> FEATURE:
<223> OTHER INFORMATION: LTG 1905_(EF1a- VH-2 CD33 -CD8 TM-41BB-CD3
    zeta)

<400> SEQUENCE: 16

```
Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly
                20                  25                  30

Leu Val Gln Pro Gly Gly Ser Leu Arg Leu Ser Cys Ala Ala Ser
            35                  40                  45

Gly Phe Thr Phe Ser Ser Tyr Gly Met Ser Trp Val Arg Gln Ala Pro Arg
        50                  55                  60

Lys Gly Leu Glu Trp Ile Gly Glu Ile Asn His Ser Gly Ser Thr Asn
65                  70                  75                  80

Tyr Asn Pro Ser Leu Lys Ser Arg Val Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Thr Tyr Tyr Cys Ala Arg Pro Leu Asn Tyr Tyr Tyr Tyr Met
            115                 120                 125

Asp Val Trp Gly Lys Gly Thr Thr Val Thr Val Ser Ser Ala Ala Ala
130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
                195                 200                 205

Ile Thr Leu Tyr Cys Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
                245                 250                 255

Val Lys Phe Ser Arg Ser Ala Asp Ala Pro Ala Tyr Gln Gln Gly Gln
                260                 265                 270

Asn Gln Leu Tyr Asn Glu Leu Asn Leu Gly Arg Arg Glu Glu Tyr Asp
                275                 280                 285

Val Leu Asp Lys Arg Arg Gly Arg Asp Pro Glu Met Gly Gly Lys Pro
290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
                340                 345                 350

Lys Asp Thr Tyr Asp Ala Leu His Met Gln Ala Leu Pro Pro Arg
                355                 360                 365
```

<210> SEQ ID NO 17
<211> LENGTH: 1083
<212> TYPE: DNA
<213> ORGANISM: Artificial

```
<220> FEATURE:
<223> OTHER INFORMATION: LTG 1906 (EF1a- VH-4 CD33 -CD8 TM-41BB-CD3
      zeta) nucleic acid sequence

<400> SEQUENCE: 17
atgctgctgc tggtgaccag cctgctgctg tgcgaactgc cgcatccggc gtttctgctg      60
attccggagg tgcagctggt ggagtctggg ggaggcttgg tacagcctgg agggtccctg     120
agactctcct gtgcagcctc tggattcacc ttcagtagct atggcatgag ctgggtccgc     180
caggctccaa gacaagggct tgagtgggtg gccaacataa agcaagatgg aagtgagaaa     240
tactatgcgg actcagtgaa gggccgattc accatctcca gagacaattc caagaacacg     300
ctgtatctgc aaatgaacag cctgagagcc gaggacacag ccacgtatta ctgtgcgaaa     360
gaaaatgtgg actggggcca gggcaccctg gtcaccgtct cctcagcggc cgcaactacc     420
accccctgccc ctcggccgcc gactccggcc ccaaccatcg caagccaacc cctctccttg     480
cgccccgaag cttgccgccc ggccgcgggt ggagccgtgc ataccggggg ctggactttt     540
gcctgcgata tctacatttg gccccgctg ccggcactt gcggcgtgct cctgctgtcg     600
ctggtcatca ccctttactg caagaggggc cggaagaagc tgctttacat cttcaagcag     660
ccgttcatgc ggcccgtgca gacgactcag gaagaggacg gatgctcgtg cagattccct     720
gaggaggaag aggggggatg cgaactgcgc gtcaagttct cacggtccgc gacgccccc      780
gcatatcaac agggccagaa tcagctctac aacgagctga acctgggaag agagaggag      840
tacgacgtgc tggacaagcg acgcggacgc gacccggaga tgggggggaa accacggcgg     900
aaaaaccctc aggaaggact gtacaacgaa ctccagaaag acaagatggc ggaagcctac     960
tcagaaatcg ggatgaaggg agagcggagg aggggaaagg gtcacgacgg gctgtaccag    1020
ggactgagca ccgccactaa ggatacctac gatgccttgc atatgcaagc actcccaccc    1080
cgg                                                                  1083

<210> SEQ ID NO 18
<211> LENGTH: 361
<212> TYPE: PRT
<213> ORGANISM: Artificial
<220> FEATURE:
<223> OTHER INFORMATION: LTG 1906 (EF1a- VH-4 CD33 -CD8 TM-41BB-CD3
      zeta) nucleic acid sequence

<400> SEQUENCE: 18

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125
```

```
Thr Leu Val Thr Val Ser Ser Ala Ala Ala Thr Thr Pro Ala Pro
        130                 135                 140
Arg Pro Pro Thr Pro Ala Pro Thr Ile Ala Ser Gln Pro Leu Ser Leu
145                 150                 155                 160
Arg Pro Glu Ala Cys Arg Pro Ala Ala Gly Gly Ala Val His Thr Arg
                165                 170                 175
Gly Leu Asp Phe Ala Cys Asp Ile Tyr Ile Trp Ala Pro Leu Ala Gly
            180                 185                 190
Thr Cys Gly Val Leu Leu Leu Ser Leu Val Ile Thr Leu Tyr Cys Lys
        195                 200                 205
Arg Gly Arg Lys Lys Leu Leu Tyr Ile Phe Lys Gln Pro Phe Met Arg
210                 215                 220
Pro Val Gln Thr Thr Gln Glu Glu Asp Gly Cys Ser Cys Arg Phe Pro
225                 230                 235                 240
Glu Glu Glu Glu Gly Gly Cys Glu Leu Arg Val Lys Phe Ser Arg Ser
                245                 250                 255
Ala Asp Ala Pro Ala Tyr Gln Gln Gly Gln Asn Gln Leu Tyr Asn Glu
            260                 265                 270
Leu Asn Leu Gly Arg Arg Glu Glu Tyr Asp Val Leu Asp Lys Arg Arg
        275                 280                 285
Gly Arg Asp Pro Glu Met Gly Gly Lys Pro Arg Arg Lys Asn Pro Gln
290                 295                 300
Glu Gly Leu Tyr Asn Glu Leu Gln Lys Asp Lys Met Ala Glu Ala Tyr
305                 310                 315                 320
Ser Glu Ile Gly Met Lys Gly Glu Arg Arg Arg Gly Lys Gly His Asp
                325                 330                 335
Gly Leu Tyr Gln Gly Leu Ser Thr Ala Thr Lys Asp Thr Tyr Asp Ala
            340                 345                 350
Leu His Met Gln Ala Leu Pro Pro Arg
        355                 360

<210> SEQ ID NO 19
<211> LENGTH: 1491
<212> TYPE: DNA
<213> ORGANISM: Artificial
<220> FEATURE:
<223> OTHER INFORMATION: LTG1936_(EF1a_ScFv9 CD33 CD8 TM-41BB-CD3 zeta
      CAR)

<400> SEQUENCE: 19
atgctgctgc tggtgaccag cctgctgctg tgcgaactgc cgcatccggc gtttctgctg      60
attccgcagg tgcagctggt gcaatctggg gcagaggtga aaaagcccgg ggagtctctg     120
aggatctcct gtaagggttc tggattcagt tttcccacct actggatcgg ctgggtgcgc     180
cagatgcccg ggaaaggcct ggagtggatg gggatcatct atcctggtga ctctgatacc     240
agatacagcc cgtccttcca aggccaggtc accatctcag ccgacaagtc catcagcacc     300
gcctacctgc agtggagcag cctgaaggcc tcggacaccg ccatgtatta ctgtgcgaga     360
ctagttggag atggctacaa tacgggggct tttgatatct ggggccaagg acaatggtc     420 accgtctctt caggaggtgg cgggtctggt ggtggcggta cggtggtgg cggatccgat     480 attgtgatga cccacactcc actctctctg tccgtcaccc ctggacagcc ggcctccatc     540
tcctgcaagt ctagtcagag cctcctgcat agtaatggaa agacctattt gtattggtac     600
ctgcagaagc caggccagcc tccacagctc ctgatctatg agcttccaa ccggttctct     660 ggagtgccag acaggttcag tggcagcggg tcagggacag atttcacact gaaaatcagc     720
```

```
cgggtggagg ctgaggatgt tggggtttat tactgcatgc aaagtataca gcttcctatc    780
accttcggcc aagggacacg actggagatt aaagcggccg caactaccac ccctgcccct    840
cggccgccga ctccggcccc aaccatcgca agccaacccc tctccttgcg ccccgaagct    900
tgccgcccgg ccgcggtgg agccgtgcat acccgggggc tggactttgc ctgcgatatc    960
tacatttggg ccccgctggc cggcacttgc ggcgtgctcc tgctgtcgct ggtcatcacc    1020
ctttactgca gaggggccg gaagaagctg ctttacatct tcaagcagcc gttcatgcgg    1080
cccgtgcaga cgactcagga gaggacgga tgctcgtgca gattccctga ggaggaagag    1140
ggggatgcg aactgcgcgt caagttctca cggtccgccg acgcccccgc atatcaacag    1200
ggccagaatc agctctacaa cgagctgaac ctgggaagga gagaggagta cgacgtgctg    1260
gacaagcgac gcggacgcga cccggagatg ggggggaaac cacggcggaa aaaccctcag    1320
gaaggactgt acaacgaact ccagaaagac aagatggcgg aagcctactc agaaatcggg    1380
atgaagggag agcggaggag gggaaagggt cacgacgggc tgtaccaggg actgagcacc    1440
gccactaagg atacctacga tgccttgcat atgcaagcac tcccaccccg g             1491

<210> SEQ ID NO 20
<211> LENGTH: 497
<212> TYPE: PRT
<213> ORGANISM: Artificial
<220> FEATURE:
<223> OTHER INFORMATION: LTG1936_(EF1a_ScFv9 CD33 CD8 TM-41BB-CD3 zeta
      CAR)

<400> SEQUENCE: 20

Met Leu Leu Leu Val Thr Ser Leu Leu Cys Glu Leu Pro His Pro
1               5                   10                  15

Ala Phe Leu Leu Ile Pro Gln Val Gln Leu Val Gln Ser Gly Ala Glu
                20                  25                  30

Val Lys Lys Pro Gly Glu Ser Leu Arg Ile Ser Cys Lys Gly Ser Gly
            35                  40                  45

Phe Ser Phe Pro Thr Tyr Trp Ile Gly Trp Val Arg Gln Met Pro Gly
        50                  55                  60

Lys Gly Leu Glu Trp Met Gly Ile Ile Tyr Pro Gly Asp Ser Asp Thr
65                  70                  75                  80

Arg Tyr Ser Pro Ser Phe Gln Gly Gln Val Thr Ile Ser Ala Asp Lys
                85                  90                  95

Ser Ile Ser Thr Ala Tyr Leu Gln Trp Ser Ser Leu Lys Ala Ser Asp
            100                 105                 110

Thr Ala Met Tyr Tyr Cys Ala Arg Leu Val Gly Asp Gly Tyr Asn Thr
        115                 120                 125

Gly Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Val Met Thr His Thr Pro Leu Ser Leu Ser Val Thr Pro Gly Gln
                165                 170                 175

Pro Ala Ser Ile Ser Cys Lys Ser Ser Gln Ser Leu Leu His Ser Asn
            180                 185                 190

Gly Lys Thr Tyr Leu Tyr Trp Tyr Leu Gln Lys Pro Gly Gln Pro Pro
        195                 200                 205

Gln Leu Leu Ile Tyr Gly Ala Ser Asn Arg Phe Ser Gly Val Pro Asp
    210                 215                 220
```

```
Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Ser Ile
            245                 250                 255

Gln Leu Pro Ile Thr Phe Gly Gln Gly Thr Arg Leu Glu Ile Lys Ala
        260                 265                 270

Ala Ala Thr Thr Thr Pro Ala Pro Arg Pro Pro Thr Pro Ala Pro Thr
    275                 280                 285

Ile Ala Ser Gln Pro Leu Ser Leu Arg Pro Glu Ala Cys Arg Pro Ala
290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 21
<211> LENGTH: 1503
<212> TYPE: DNA
<213> ORGANISM: Artificial
<220> FEATURE:
<223> OTHER INFORMATION: LTG1937_(EF1a_ScFv10 CD33 CD8 TM-41BB-CD3 zeta CAR)

<400> SEQUENCE: 21

```
atgctgctgc tggtgaccag cctgctgctg tgcgaactgc cgcatccggc gtttctgctg      60
attccgcagg tacagctgca gcagtcaggt ccaggactgg tgaagccctc gcagaccctc     120
tcactcacct gtgccatctc cggggacagt gtctctagca acactgctgc ttggaactgg     180
atcaggcagt cccccatcgag aggccttgag tggctgggaa ggacatacta caggtccaag    240
tggtataatg attatgcagt ccctgtgaaa agtcgaataa ccatcaaccc agacacatcc     300
aagaaccagt tctccctgca gctgaactct gtgactcccg aggacacggc tgtgtattac     360
tgtgcaagag aaacgtatta ctatggttcg gggagttatt gggatgcttt tgatatctgg    420
```

```
ggccaaggga ccacggtcac cgtctcctca ggaggtggcg ggtctggtag tggcggtagc    480
ggtggtggcg gatcccagtc tgtcgtgacg cagccgccct cagtgtctgc ggccccagga    540
cagaaggtca ccatctcctg ctctggaagc agctccaaca ttgggaataa ttatgtatcc    600
tggtaccagc agctcccagg cacggccccc aaactcttca tctataaaaa taatcagcgg    660
ccctcagagg tccctgaccg attctctggc tccaagtctg gcacctcagc ctccctggcc    720
atcagtgggc tccagtctga cgatgaggct gactactact gtgcagcatg ggatgacagg    780
ctgaatggat atgtcttcgg aactgggacc aaggtcaccg tcctagcggc cgcaactacc    840 accccctgccc ctcggccgcc gactccggcc ccaaccatcg caagccaacc cctctccttg    900
cgccccgaag cttgccgccc ggccgcgggt ggagccgtgc atacccgggg gctggacttt    960
gcctgcgata tctacatttg gccccgctg ccggcactt cggcgtgct cctgctgtcg     1020 ctggtcatca cccttactg caagagggc cggaagaagc tgctttacat cttcaagcag    1080
ccgttcatgc ggcccgtgca cgacgactcag gaagaggacg gatgctcgtg cagattccct    1140
gaggaggaag agggggatg cgaactgcgc gtcaagttct cacggtccgc cgacgccccc    1200
gcatatcaac agggccagaa tcagctctac aacgagctga acctgggaag gagagaggag    1260
tacgacgtgc tggacaagcg acgcggacg gacccggaga tgggggggaa ccacggcgg    1320 aaaaaccctc aggaaggact gtacaacgaa ctccagaaag acaagatggc ggaagcctac    1380
tcagaaatcg ggatgaaggg agagcggagg aggggaaagg gtcacgacgg gctgtaccag    1440
ggactgagca ccgccactaa ggatacctac gatgccttgc atatgcaagc actcccaccc    1500
cgg                                                                1503
```

<210> SEQ ID NO 22
<211> LENGTH: 501
<212> TYPE: PRT
<213> ORGANISM: Artificial
<220> FEATURE:
<223> OTHER INFORMATION: LTG1937_(EF1a_ScFv10 CD33 CD8 TM-41BB-CD3 zeta CAR)

<400> SEQUENCE: 22

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Thr Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Pro Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Thr Tyr Tyr Tyr
        115                 120                 125

Gly Ser Gly Ser Tyr Trp Asp Ala Phe Asp Ile Trp Gly Gln Gly Thr
    130                 135                 140

Thr Val Thr Val Ser Ser Gly Gly Gly Ser Gly Ser Gly Gly Ser
145                 150                 155                 160
```

Gly Gly Gly Gly Ser Gln Ser Val Val Thr Gln Pro Ser Val Ser
            165                 170                 175

Ala Ala Pro Gly Gln Lys Val Thr Ile Ser Cys Ser Gly Ser Ser
            180                 185                 190

Asn Ile Gly Asn Asn Tyr Val Ser Trp Tyr Gln Gln Leu Pro Gly Thr
            195                 200                 205

Ala Pro Lys Leu Phe Ile Tyr Lys Asn Asn Gln Arg Pro Ser Glu Val
            210                 215                 220

Pro Asp Arg Phe Ser Gly Ser Lys Ser Gly Thr Ser Ala Ser Leu Ala
225                 230                 235                 240

Ile Ser Gly Leu Gln Ser Asp Asp Glu Ala Asp Tyr Tyr Cys Ala Ala
            245                 250                 255

Trp Asp Asp Arg Leu Asn Gly Tyr Val Phe Gly Thr Gly Thr Lys Val
            260                 265                 270

Thr Val Leu Ala Ala Ala Thr Thr Thr Pro Ala Pro Arg Pro Pro Thr
            275                 280                 285

Pro Ala Pro Thr Ile Ala Ser Gln Pro Leu Ser Leu Arg Pro Glu Ala
            290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
            325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
            355                 360                 365

Thr Gln Glu Glu Asp Gly Cys Ser Cys Arg Phe Pro Glu Glu Glu Glu
            370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
            405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
            435                 440                 445

Asn Glu Leu Gln Lys Asp Lys Met Ala Glu Ala Tyr Ser Glu Ile Gly
            450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
            485                 490                 495

Ala Leu Pro Pro Arg
            500

<210> SEQ ID NO 23
<211> LENGTH: 1485
<212> TYPE: DNA
<213> ORGANISM: Artificial
<220> FEATURE:
<223> OTHER INFORMATION: LTG1938_(EF1a_ScFv12 CD33 CD8 TM-41BB-CD3 zeta)

<400> SEQUENCE: 23
atgctgctgc tggtgaccag cctgctgctg tgcgaactgc cgcatccggc gtttctgctg      60
attccgcagg tacagctgca gcagtcaggt ccaggactgg tgaagccctc gcagaccctc     120

```
tcactcacct gtgccatctc cggggacagt gtctctagca acagtgctgc ttggaactgg    180
atcaggcagt ccccatcgag aggccttgag tggctgggag ggacatacta caggtccaag    240
tggtataatg attatgcagt atctgtgaaa agtcgaataa ttatcaacgc agacacatcg    300
aagaaccagt tctccctgca gctgaactct gtgactcccg aggacacggc tgtgtattac    360
tgtgcgaggg gatattacta tgatagtacc gactggttcg acccctgggg ccagggaacc    420
ctggtcaccg tctcctcagg aggtggcggg tctggtggtg gcggtagcgg tggtggcgga    480
tcctcttctg agctgactca ggacccaact gtgtctgtgg ccttgggaca gacagtcagg    540
atcacatgcc aaggagacag cctcagaagc tattatgcaa gctggtacca gcagaagcca    600
ggacaggccc ctgtacttgt catctatggt aaaaacaacc ggccctcagg gatcccagac    660
cgattctctg gctccagctc aggaaacaca gcttccttga ccatcactgg ggctcaggcg    720
gaagatgagg ctgactatta ctgttcctcc cgggacggca gtggtcatcc atatctcttc    780
ggacctggga ccaaggtcac cgttcttgcg gccgcaacta ccaccccctgc ccctcggccg    840 ccgactccgg ccccaaccat cgcaagccaa cccctctcct gcgccccga agcttgccgc    900 ccggccgcgg gtggagccgt gcatacccgg gggctggact ttgcctgcga tatctacatt    960
tgggccccgc tggccggcac ttgcggcgtg ctcctgctgt cgctggtcat caccctttac   1020
tgcaagaggg gccggaagaa gctgctttac atcttcaagc agccgttcat gcggcccgtg   1080
cagacgactc aggaagagga cggatgctcg tgcagattcc ctgaggagga agagggggga   1140
tgcgaactgc gcgtcaagtt ctcacggtcc gccgacgccc ccgcatatca cagggccag   1200 aatcagctct acaacgagct gaacctggga aggagagagg agtacgacgt gctggacaag   1260
cgacgcggac gcgacccgga gatggggggg aaaccacggc ggaaaaaccc tcaggaagga   1320
ctgtacaacg aactccagaa agacaagatg gcggaagcct actcagaaat cgggatgaag   1380
ggagagcgga ggaggggaaa gggtcacgac gggctgtacc agggactgag caccgccact   1440
aaggatacct acgatgcctt gcatatgcaa gcactccac cccgg                    1485
```

<210> SEQ ID NO 24
<211> LENGTH: 495
<212> TYPE: PRT
<213> ORGANISM: Artificial
<220> FEATURE:
<223> OTHER INFORMATION: LTG1938_(EF1a_ScFv12 CD33 CD8 TM-41BB-CD3 zeta)

<400> SEQUENCE: 24

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
                20                  25                  30

Leu Val Lys Pro Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Gly Thr Tyr Tyr Arg Ser Lys
65                  70                  75                  80

Trp Tyr Asn Asp Tyr Ala Val Ser Val Lys Ser Arg Ile Ile Ile Asn
                85                  90                  95

Ala Asp Thr Ser Lys Asn Gln Phe Ser Leu Gln Leu Asn Ser Val Thr
            100                 105                 110
```

Pro Glu Asp Thr Ala Val Tyr Tyr Cys Ala Arg Gly Tyr Tyr Asp
            115                 120                 125

Ser Thr Asp Trp Phe Asp Pro Trp Gly Gln Gly Thr Leu Val Thr Val
130                 135                 140

Ser Ser Gly Gly Gly Gly Ser Gly Gly Gly Ser Gly Gly Gly Gly
145                 150                 155                 160

Ser Ser Ser Glu Leu Thr Gln Asp Pro Thr Val Ser Val Ala Leu Gly
                165                 170                 175

Gln Thr Val Arg Ile Thr Cys Gln Gly Asp Ser Leu Arg Ser Tyr Tyr
            180                 185                 190

Ala Ser Trp Tyr Gln Gln Lys Pro Gly Gln Ala Pro Val Leu Val Ile
        195                 200                 205

Tyr Gly Lys Asn Asn Arg Pro Ser Gly Ile Pro Asp Arg Phe Ser Gly
    210                 215                 220

Ser Ser Ser Gly Asn Thr Ala Ser Leu Thr Ile Thr Gly Ala Gln Ala
225                 230                 235                 240

Glu Asp Glu Ala Asp Tyr Tyr Cys Ser Ser Arg Asp Gly Ser Gly His
                245                 250                 255

Pro Tyr Leu Phe Gly Pro Gly Thr Lys Val Thr Val Leu Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 25
<211> LENGTH: 1479
<212> TYPE: DNA
<213> ORGANISM: Artificial
<220> FEATURE:

<223> OTHER INFORMATION: LTG1939_(EF1a_ScFv15 CD33 CD8 TM-41BB-CD3 zeta)

<400> SEQUENCE: 25

```
atgctgctgc tggtgaccag cctgctgctg tgcgaactgc cgcatccggc gtttctgctg      60
attccggagg tccagctggt gcagtctgga gcagaggtga aaaagcccgg ggagtctctg     120
aagatctcct gtaagggttc tggatacagc tttaccagct actggatcgg ctgggtgcgc     180
cagatgcccg ggaaaggcct ggagtggatg gggatcatct atcctggtga ctctgatacc     240
agatacagcc cgtccttcca aggccaggtc accatctcag ccgacaagtc catcagcacc     300
gcctacctgc agtggagcag cctgaaggcc tcggacaccg ccatgtatta ctgtgcgaga     360
ctgactacgg ctgggggtat ggacgtctgg ggccaaggga ccacggtcac cgtctcctca     420
ggaggtggcg gtctggtgg tggcggtagc ggtggtggcg gatccgaaat tgtgctgact     480
cagtctccac tctccctgcc cgtcacccgt ggacagccgg cctccatctc ctgcaggtct     540
agtcaaagcc tcgtacacag tgatggaaac acctacttga gttggcttca ccagaggcca     600
ggccagcctc caagactcct aatgtataag atttctaacc ggttctctgg ggtcacagac     660
agattcagtg gcagcgggtc agggacagat ttcacactga aaatcagccg ggtggaggct     720
gaggatgttg ggttttatta ctgcatgcaa ggtatacacc taccgctcac tttcggcgga     780
gggaccaagc tggagatcaa agcggccgca actaccaccc ctgcccctcg gccgccgact     840
ccggccccaa ccatcgcaag ccaaccctc tccttgcgcc cgaagcttg ccgcccggcc      900
gcgggtggag ccgtgcatac ccggggggctg gactttgcct gcgatatcta catttgggcc     960
ccgctggccg gcacttgcgg cgtgctcctg ctgtcgctgg tcatcaccct ttactgcaag    1020
aggggccgga gaagctgct ttacatcttc aagcagccgt tcatgcggcc cgtgcagacg    1080
actcaggaag aggacggatg ctcgtgcaga ttccctgagg aggaagaggg gggatgcgaa    1140
ctgcgcgtca gttctcacg gtccgccgac gcccccgcat atcaacaggg ccagaatcag    1200
ctctacaacg agctgaacct gggaaggaga gaggagtacg acgtgctgga caagcgacgc    1260
ggacgcgacc cggagatggg ggggaaacca cggcggaaaa accctcagga aggactgtac    1320
aacgaactcc agaaagacaa gatggcggaa gcctactcag aaatcgggat gaagggagag    1380
cggaggaggg gaaagggtca cgacgggctg taccaggac tgagcaccgc cactaaggat    1440
acctacgatg ccttgcatat gcaagcactc ccaccccgg                           1479
```

<210> SEQ ID NO 26
<211> LENGTH: 493
<212> TYPE: PRT
<213> ORGANISM: Artificial
<220> FEATURE:
<223> OTHER INFORMATION: LTG1939_(EF1a_ScFv15 CD33 CD8 TM-41BB-CD3 zeta)

<400> SEQUENCE: 26

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Glu Ser Leu Lys Ile Ser Cys Lys Gly Ser Gly
        35                  40                  45

Tyr Ser Phe Thr Ser Tyr Trp Ile Gly Trp Val Arg Gln Met Pro Gly
    50                  55                  60

Lys Gly Leu Glu Trp Met Gly Ile Ile Tyr Pro Gly Asp Ser Asp Thr
65                  70                  75                  80
```

```
Arg Tyr Ser Pro Ser Phe Gln Gly Gln Val Thr Ile Ser Ala Asp Lys
                85                  90                  95

Ser Ile Ser Thr Ala Tyr Leu Gln Trp Ser Ser Leu Lys Ala Ser Asp
            100                 105                 110

Thr Ala Met Tyr Tyr Cys Ala Arg Leu Thr Thr Ala Gly Gly Met Asp
            115                 120                 125

Val Trp Gly Gln Gly Thr Thr Val Thr Val Ser Ser Gly Gly Gly Gly
        130                 135                 140

Ser Gly Gly Gly Gly Ser Gly Gly Gly Gly Ser Glu Ile Val Leu Thr
145                 150                 155                 160

Gln Ser Pro Leu Ser Leu Pro Val Thr Leu Gly Gln Pro Ala Ser Ile
                165                 170                 175

Ser Cys Arg Ser Ser Gln Ser Leu Val His Ser Asp Gly Asn Thr Tyr
            180                 185                 190

Leu Ser Trp Leu His Gln Arg Pro Gly Gln Pro Pro Arg Leu Leu Met
        195                 200                 205

Tyr Lys Ile Ser Asn Arg Phe Ser Gly Val Thr Asp Arg Phe Ser Gly
    210                 215                 220

Ser Gly Ser Gly Thr Asp Phe Thr Leu Lys Ile Ser Arg Val Glu Ala
225                 230                 235                 240

Glu Asp Val Gly Val Tyr Tyr Cys Met Gln Gly Ile His Leu Pro Leu
                245                 250                 255

Thr Phe Gly Gly Gly Thr Lys Leu Glu Ile Lys Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

```
<210> SEQ ID NO 27
<211> LENGTH: 72
<212> TYPE: DNA
<213> ORGANISM: Homo sapiens

<400> SEQUENCE: 27
atctacatct gggcgcccct tggccgggact tgtggggtcc ttctcctgtc actggttatc    60
accctttact gc                                                         72

<210> SEQ ID NO 28
<211> LENGTH: 22
<212> TYPE: PRT
<213> ORGANISM: Homo sapiens

<400> SEQUENCE: 28

Ile Trp Ala Pro Leu Ala Gly Thr Cys Gly Val Leu Leu Ser Leu
1               5                   10                  15

Val Ile Thr Leu Tyr Cys
            20

<210> SEQ ID NO 29
<211> LENGTH: 135
<212> TYPE: DNA
<213> ORGANISM: Homo sapiens

<400> SEQUENCE: 29
accacgacgc cagcgccgcg accaccaaca ccggcgccca ccatcgcgtc gcagcccctg    60
tccctgcgcc agaggcgtg ccggccagcg gcgggggggcg cagtgcacac gagggggctg   120
gacttcgcct gtgat                                                    135

<210> SEQ ID NO 30
<211> LENGTH: 47
<212> TYPE: PRT
<213> ORGANISM: Homo sapiens

<400> SEQUENCE: 30

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 31
<211> LENGTH: 42
<212> TYPE: PRT
<213> ORGANISM: Homo sapiens

<400> SEQUENCE: 31

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 32
<211> LENGTH: 106
<212> TYPE: PRT
<213> ORGANISM: Homo sapiens
```

<400> SEQUENCE: 32

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 33
<211> LENGTH: 126
<212> TYPE: DNA
<213> ORGANISM: Homo sapiens

<400> SEQUENCE: 33
aaacggggca gaaagaaact cctgtatata ttcaaacaac catttatgag accagtacaa        60
actactcaag aggaagatgg ctgtagctgc cgatttccag aagaagaaga aggaggatgt       120
gaactg                                                                 126

<210> SEQ ID NO 34
<211> LENGTH: 42
<212> TYPE: PRT
<213> ORGANISM: Homo sapiens

<400> SEQUENCE: 34

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 35
<211> LENGTH: 336
<212> TYPE: DNA
<213> ORGANISM: Artificial
<220> FEATURE:
<223> OTHER INFORMATION: signaling domain of CD3-zeta

<400> SEQUENCE: 35
agagtgaagt tcagcaggag cgcagacgcc cccgcgtaca gcagggcca gaaccagctc         60 tataacgagc tcaatctagg acgaagagag gagtacgatg tttggacaa gagacgtggc       120 cgggaccctg agatgggggg aaagccgaga aggaagaacc ctcaggaagg cctgtacaat       180
gaactgcaga agataagat ggcggaggcc tacagtgaga ttgggatgaa aggcgagcgc       240
cggaggggca aggggcacga tggcctttac cagggtctca gtacagccac caaggacacc       300
tacgacgccc ttcacatgca ggccctgccc cctcgc                                336

<210> SEQ ID NO 36
<211> LENGTH: 112

<212> TYPE: PRT
<213> ORGANISM: Artificial
<220> FEATURE:
<223> OTHER INFORMATION: signaling domain of CD3-zeta

<400> SEQUENCE: 36

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 37
<211> LENGTH: 726
<212> TYPE: DNA
<213> ORGANISM: Mus musculus

<400> SEQUENCE: 37
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat acactcagg agtcccatca      180
aggttcagtg gcagtgggtc tggaacagat tattctctca ccattagcaa cctggagcaa     240
gaagatattg ccacttactt ttgccaacag ggtaatacgc ttccgtacac gttcggaggg     300
gggaccaagc tggagatcac aggtggcggt ggctcgggcg gtggtgggtc gggtggcggc     360
ggatctgagg tgaaactgca ggagtcagga cctggcctgg tggcgccctc acagagcctg     420
tccgtcacat gcactgtctc aggggtctca ttacccgact atggtgtaag ctggattcgc     480
cagcctccac gaaagggtct ggagtggctg gagtaatat ggggtagtga aaccacatac      540
tataattcag ctctcaaatc cagactgacc atcatcaagg acaactccaa gagccaagtt     600
ttcttaaaaa tgaacagtct gcaaactgat gacacagcca tttactactg tgccaaacat     660
tattactacg gtggtagcta tgctatggac tactggggcc aaggaacctc agtcaccgtc     720
tcctca                                                                726

<210> SEQ ID NO 38
<211> LENGTH: 242
<212> TYPE: PRT
<213> ORGANISM: Mus musculus

<400> SEQUENCE: 38

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

```
Tyr His Thr Ser Arg Leu His Ser Gly Val Pro Ser Arg Phe Ser Gly
         50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
        130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 39
<211> LENGTH: 66
<212> TYPE: DNA
<213> ORGANISM: Artificial
<220> FEATURE:
<223> OTHER INFORMATION: GMCSF leader peptide

<400> SEQUENCE: 39
atgctgctgc tggtgaccag cctgctgctg tgcgaactgc cgcatccggc gtttctgctg     60
attccg                                                               66

<210> SEQ ID NO 40
<211> LENGTH: 22
<212> TYPE: PRT
<213> ORGANISM: Artificial
<220> FEATURE:
<223> OTHER INFORMATION: GMCSF leader peptide

<400> SEQUENCE: 40

Met Leu Leu Leu Val Thr Ser Leu Leu Leu Cys Glu Leu Pro His Pro
 1               5                  10                  15

Ala Phe Leu Leu Ile Pro
                20

<210> SEQ ID NO 41
<211> LENGTH: 85
<212> TYPE: DNA
<213> ORGANISM: Artificial
<220> FEATURE:
<223> OTHER INFORMATION: TNFRSF19 leader peptide
```

<400> SEQUENCE: 41
ggctctgaaa gtgctgttgg aacaagaaaa gaccttcttc accttgctcg tgttgctggg    60
gtacctgtcc tgcaaagtca cctgt    85

<210> SEQ ID NO 42
<211> LENGTH: 29
<212> TYPE: PRT
<213> ORGANISM: Artificial
<220> FEATURE:
<223> OTHER INFORMATION: TNFRSF19 leader peptide

<400> SEQUENCE: 42

Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys
            20                  25

<210> SEQ ID NO 43
<211> LENGTH: 63
<212> TYPE: DNA
<213> ORGANISM: Artificial
<220> FEATURE:
<223> OTHER INFORMATION: CD8 alpha leader peptide

<400> SEQUENCE: 43
atggcgctgc cggtgaccgc gctgctgctg ccgctggcgc tgctgctgca tgcggcgcgc    60
ccg    63

<210> SEQ ID NO 44
<211> LENGTH: 21
<212> TYPE: PRT
<213> ORGANISM: Artificial
<220> FEATURE:
<223> OTHER INFORMATION: CD8 alpha leader peptide

<400> SEQUENCE: 44

Met Ala Leu Pro Val Thr Ala Leu Leu Leu Pro Leu Ala Leu Leu Leu
1               5                   10                  15

His Ala Ala Arg Pro
            20

<210> SEQ ID NO 45
<211> LENGTH: 123
<212> TYPE: DNA
<213> ORGANISM: Artificial
<220> FEATURE:
<223> OTHER INFORMATION: CD28 co-stimulatory domain

<400> SEQUENCE: 45
cggtcgaaga ggtccagact cttgcactcc gactacatga acatgactcc tagaaggccc    60
ggacccacta gaaagcacta ccagccgtac gcccctcctc gggatttcgc cgcataccgg   120
tcc    123

<210> SEQ ID NO 46
<211> LENGTH: 41
<212> TYPE: PRT
<213> ORGANISM: Artificial
<220> FEATURE:
<223> OTHER INFORMATION: CD28 co-stimulatory domain

<400> SEQUENCE: 46

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 47
<211> LENGTH: 336
<212> TYPE: DNA
<213> ORGANISM: Artificial
<220> FEATURE:
<223> OTHER INFORMATION: CD3 zeta activation domain

<400> SEQUENCE: 47

```
agagtgaagt tcagccgctc agccgatgca ccggcctacc agcagggaca gaaccagctc    60
tacaacgagc tcaacctggg tcggcgggaa gaatatgacg tgctggacaa acggcgcggc   120
agagatccgg agatggggggg aaagccgagg aggaagaacc ctcaagaggg cctgtacaac   180
gaactgcaga aggacaagat ggcggaagcc tactccgaga tcggcatgaa gggagaacgc   240
cggagaggga aggtcatga cggactgtac cagggcctgt caactgccac taaggacact   300
tacgatgcgc tccatatgca agctttgccc ccgcgg                             336
```

<210> SEQ ID NO 48
<211> LENGTH: 112
<212> TYPE: PRT
<213> ORGANISM: Artificial
<220> FEATURE:
<223> OTHER INFORMATION: CD3 zeta activation domain

<400> SEQUENCE: 48

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 49
<211> LENGTH: 201
<212> TYPE: DNA
<213> ORGANISM: Artificial
<220> FEATURE:
<223> OTHER INFORMATION: TNFRSF19 hinge and transmembrane domain

<400> SEQUENCE: 49

```
gcggccgcgg tcggattcca agacatggaa tgcgtgccct gcggcgaccc gccacctcct    60
tacgagccgc actgcgcatc gaaggtcaac ctcgtgaaga tcgcgagcac cgcgtcctca   120
```

```
ccccgggata ctgctctggc cgccgtgatt tgttccgcct tggccaccgt gcttctggcc      180
ctgctgatcc tctgtgtgat c                                                201
```

<210> SEQ ID NO 50
<211> LENGTH: 22
<212> TYPE: PRT
<213> ORGANISM: Artificial
<220> FEATURE:
<223> OTHER INFORMATION: TNFRSF19 hinge and transmembrane domain

<400> SEQUENCE: 50

```
Leu Ala Ala Val Ile Cys Ser Ala Leu Ala Thr Val Leu Leu Ala Leu
1               5                   10                  15

Leu Ile Leu Cys Val Ile
            20
```

<210> SEQ ID NO 51
<211> LENGTH: 63
<212> TYPE: DNA
<213> ORGANISM: Artificial
<220> FEATURE:
<223> OTHER INFORMATION: TNFRSF19 transmembrane domain

<400> SEQUENCE: 51

```
gccgccgtga tttgttccgc cttggccacc gtgcttctgg ccctgctgat cctctgtgtg      60
atc                                                                   63
```

<210> SEQ ID NO 52
<211> LENGTH: 21
<212> TYPE: PRT
<213> ORGANISM: Artificial
<220> FEATURE:
<223> OTHER INFORMATION: TNFRSF19 transmembrane domain

<400> SEQUENCE: 52

```
Ala Ala Val Ile Cys Ser Ala Leu Ala Thr Val Leu Leu Ala Leu Leu
1               5                   10                  15

Ile Leu Cys Val Ile
            20
```

<210> SEQ ID NO 53
<211> LENGTH: 138
<212> TYPE: DNA
<213> ORGANISM: Artificial
<220> FEATURE:
<223> OTHER INFORMATION: TNFRSF19 hinge domain

<400> SEQUENCE: 53

```
gcggccgcgg tcggattcca agacatggaa tgcgtgccct gcggcgaccc gccacctcct      60
tacgagccgc actgcgcatc gaaggtcaac ctcgtgaaga tcgcgagcac cgcgtcctca     120
ccccgggata ctgctctg                                                   138
```

<210> SEQ ID NO 54
<211> LENGTH: 46
<212> TYPE: PRT
<213> ORGANISM: Artificial
<220> FEATURE:
<223> OTHER INFORMATION: TNFRSF19 hinge domain

<400> SEQUENCE: 54

```
Ala Ala Ala Val Gly Phe Gln Asp Met Glu Cys Val Pro Cys Gly Asp
1               5                   10                  15
```

```
Pro Pro Pro Pro Tyr Glu Pro His Cys Ala Ser Lys Val Asn Leu Val
            20                  25                  30

Lys Ile Ala Ser Thr Ala Ser Ser Pro Arg Asp Thr Ala Leu
            35                  40                  45

<210> SEQ ID NO 55
<211> LENGTH: 80
<212> TYPE: DNA
<213> ORGANISM: Artificial
<220> FEATURE:
<223> OTHER INFORMATION: truncated TNFRSF19 hinge domain

<400> SEQUENCE: 55
tacgagcctc actgcgccag caaagtcaac ttggtgaaga tcgcgagcac tgcctcgtcc    60
cctcgggaca ctgctctggc                                                80

<210> SEQ ID NO 56
<211> LENGTH: 26
<212> TYPE: PRT
<213> ORGANISM: Artificial
<220> FEATURE:
<223> OTHER INFORMATION: truncated TNFRSF19 hinge domain

<400> SEQUENCE: 56

Tyr Glu Pro His Cys Ala Ser Lys Val Asn Leu Val Lys Ile Ala Ser
1               5                   10                  15

Thr Ala Ser Ser Pro Arg Asp Thr Ala Leu
            20                  25

<210> SEQ ID NO 57
<211> LENGTH: 222
<212> TYPE: DNA
<213> ORGANISM: Artificial
<220> FEATURE:
<223> OTHER INFORMATION: CD8a hinge domain fused to TNFRSF19
      transmembrane domain

<400> SEQUENCE: 57
gcggccgcgc cgcccctcg gcccccgact cctgccccga cgatcgcttc ccaacctctc    60
tcgctgcgcc cggaagcatg ccggcccgcc gccggtggcg ctgtccacac tcgcggactg   120
gactttgata ccgcactggc ggccgtgatc tgtagcgccc tggccaccgt gctgctggcg   180
ctgctcatcc tttgcgtgat ctactgcaag cggcagccta gg                      222

<210> SEQ ID NO 58
<211> LENGTH: 74
<212> TYPE: PRT
<213> ORGANISM: Artificial
<220> FEATURE:
<223> OTHER INFORMATION: CD8a hinge domain fused to TNFRSF19
      transmembrane domain

<400> SEQUENCE: 58

Ala Ala Ala Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Asp Thr Ala Leu Ala Ala
            35                  40                  45

Val Ile Cys Ser Ala Leu Ala Thr Val Leu Leu Ala Leu Leu Ile Leu
        50                  55                  60
```

Cys Val Ile Tyr Cys Lys Arg Gln Pro Arg
65                  70

<210> SEQ ID NO 59
<211> LENGTH: 123
<212> TYPE: DNA
<213> ORGANISM: Artificial
<220> FEATURE:
<223> OTHER INFORMATION: CD28 co-stimulatory domain

<400> SEQUENCE: 59
cggtcgaaga ggtccagact cttgcactcc gactacatga acatgactcc tagaaggccc     60
ggacccacta gaaagcacta ccagccgtac gcccctcctc gggatttcgc cgcataccgg    120
tcc                                                                  123

<210> SEQ ID NO 60
<211> LENGTH: 41
<212> TYPE: PRT
<213> ORGANISM: Artificial
<220> FEATURE:
<223> OTHER INFORMATION: CD28 co-stimulatory domain

<400> SEQUENCE: 60

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 61
<211> LENGTH: 336
<212> TYPE: DNA
<213> ORGANISM: Artificial
<220> FEATURE:
<223> OTHER INFORMATION: CD3 zeta version 2

<400> SEQUENCE: 61
cgcgtgaaat ttagccgcag cgcggatgcg ccggcgtatc agcagggcca gaaccagctg     60
tataacgaac tgaacctggg ccgccgcgaa gaatatgatg tgctggataa acgccgcggc    120
cgcgatccgg aaatgggcgg caaaccgcgc cgcaaaaacc cgcaggaagg cctgtataac    180
gaactgcaga agataaaat ggcggaagcg tatagcgaaa ttggcatgaa aggcgaacgc    240
cgccgcggca aaggccatga tggcctgtat cagggcctga gcaccgcgac caaagatacc    300
tatgatgcgc tgcatatgca ggcgctgccg ccgcgc                              336

<210> SEQ ID NO 62
<211> LENGTH: 112
<212> TYPE: PRT
<213> ORGANISM: Artificial
<220> FEATURE:
<223> OTHER INFORMATION: CD3 zeta version 2

<400> SEQUENCE: 62

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

```
Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 63
<211> LENGTH: 93
<212> TYPE: DNA
<213> ORGANISM: Artificial
<220> FEATURE:
<223> OTHER INFORMATION: Furin P2A Furin

<400> SEQUENCE: 63

```
cgcgcgaaac gcagcggcag cggcgcgacc aactttagcc tgctgaaaca ggcgggcgat      60
gtggaagaaa acccgggccc gcgagcaaag agg                                   93
```

<210> SEQ ID NO 64
<211> LENGTH: 31
<212> TYPE: PRT
<213> ORGANISM: Artificial
<220> FEATURE:
<223> OTHER INFORMATION: Furin P2A Furin

<400> SEQUENCE: 64

```
Arg Ala Lys Arg Ser Gly Ser Gly Ala Thr Asn Phe Ser Leu Leu Lys
  1               5                  10                  15

Gln Ala Gly Asp Val Glu Glu Asn Pro Gly Pro Arg Ala Lys Arg
                 20                  25                  30
```

<210> SEQ ID NO 65
<211> LENGTH: 78
<212> TYPE: DNA
<213> ORGANISM: Artificial
<220> FEATURE:
<223> OTHER INFORMATION: Furin T2A

<400> SEQUENCE: 65

```
agagctaaac gctctgggtc tggtgaagga cgaggtagcc ttcttacgtg cggagacgtg      60
gaggaaaacc caggaccc                                                    78
```

<210> SEQ ID NO 66
<211> LENGTH: 26
<212> TYPE: PRT
<213> ORGANISM: Artificial
<220> FEATURE:
<223> OTHER INFORMATION: Furin T2A

<400> SEQUENCE: 66

```
Arg Ala Lys Arg Ser Gly Ser Gly Glu Gly Arg Gly Ser Leu Leu Thr
  1               5                  10                  15

Cys Gly Asp Val Glu Glu Asn Pro Gly Pro
                 20                  25
```

<210> SEQ ID NO 67
<211> LENGTH: 1005
<212> TYPE: DNA
<213> ORGANISM: Artificial
<220> FEATURE:

<223> OTHER INFORMATION: truncated EGFR (tEGFR) tag

<400> SEQUENCE: 67

```
aggaaggttt gcaatggaat cggtataggg gagtttaagg attcacttag cataaacgct    60
actaatatta aacacttcaa aaactgtacg agtataagtg gagatcttca cattttgccg   120
gttgcattcc gaggcgattc attcacccac acgccaccgc ttgacccaca agaattggat   180
attcttaaaa ccgttaaaga aataacgggg ttttgctca ttcaagcgtg gccagaaaat   240
cgcactgacc tccatgcttt cgagaacctg agattataa gaggacgaac taagcagcat   300
ggtcaattct cccttgctgt ggtcagcctg aacatcacca gtcttggttt gcggtccctc   360
aaggaaattt cagatggaga tgtcatcata agcggcaaca agaatttgtg ctatgcaaat   420
accataaact ggaaaaaact gtttggcact tccggccaga aaccaagat tatttcaaat   480
cggggtgaga acagctgcaa agccaccggc caggtttgtc atgccttgtg ctctccggaa   540
ggctgttggg ggccagaacc cagggactgc gtcagttgca gaaacgtctc aagaggccgc   600
gaatgcgttg acaagtgtaa cctccttgag ggtgagccac gagagtttgt tgagaacagc   660
gagtgtatac aatgtcaccc tgaatgtttg ccccaggcta tgaatataac ctgcacaggc   720
cgcgggcctg ataactgcat ccagtgtgct cattacatag atggacctca ctgtgtgaaa   780
acctgcccgg ccggagttat gggagaaaac aacactctgg tgtggaaata cgctgatgca   840
ggccacgtgt gccacctttg tcacccgaat tgtacatatg ggtgtaccgg tcctggactt   900
gaaggttgcc ctaccaatgg ccctaaaata cccagtatcg caactggcat ggtaggcgct   960
cttctcttgc tcttggtagt tgctctcggc ataggtcttt ttatg               1005
```

<210> SEQ ID NO 68
<211> LENGTH: 335
<212> TYPE: PRT
<213> ORGANISM: Artificial
<220> FEATURE:
<223> OTHER INFORMATION: truncated EGFR (tEGFR) tag

<400> SEQUENCE: 68

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160
```

```
Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 69
<211> LENGTH: 1080
<212> TYPE: DNA
<213> ORGANISM: Artificial
<220> FEATURE:
<223> OTHER INFORMATION: LTG1927 (EF1a-CD33_4-CD8 TM-CD28-CD3
      zeta-cfrag)

<400> SEQUENCE: 69
atgctgctgc tggtgaccag cctgctgctg tgcgaactgc cgcatccggc gtttctgctg      60
attccggagg tgcagctggt ggagtctggg ggaggcttgg tacagcctgg agggtccctg     120
agactctcct gtgcagcctc tggattcacc ttcagtagct atggcatgag ctgggtccgc     180
caggctccaa acaagggct tgagtgggtg gccaacataa agcaagatgg aagtgagaaa     240
tactatgcgg actcagtgaa gggccgattc accatctcca gagacaattc caagaacacg     300
ctgtatctgc aaatgaacag cctgagagcc gaggacacag ccacgtatta ctgtgcgaaa     360
gaaaatgtgg actgggcca gggcaccctg gtcaccgtct cctcagcggc cgcgactacc     420
actcctgcac cacggccacc taccccagcc ccaccattg caagccagcc actttcactg     480
cgccccgaag cgtgtagacc agctgctgga ggagccgtgc atacccgagg ctggacttc     540 gcctgtgaca tctacatctg gcccccattg gctggaactt cggcgtgct gctcttgtct     600 ctggtcatta ccctgtactg ccggtcgaag aggtccagac tcttgcactc cgactacatg     660
aacatgactc ctagaaggcc cggacccact agaaagcact accagccgta cgcccctcct     720
cgggatttcg ccgcataccg gtccagagtg aagttcagcc gctcagccga tgcaccggcc     780
taccagcagg gacagaacca gctctacaac gagctcaacc tgggtcggcg ggaagaatat     840
gacgtgctgg acaaacggcg cggcagagat ccggagatgg ggggaaagcc gaggaggaag     900
```

```
aaccctcaag agggcctgta caacgaactg cagaaggaca agatggcgga agcctactcc    960
gagatcggca tgaagggaga acgccggaga gggaagggtc atgacggact gtaccagggc   1020
ctgtcaactg ccactaagga cacttacgat gcgctccata tgcaagcttt gccccgcgg    1080
```

<210> SEQ ID NO 70
<211> LENGTH: 360
<212> TYPE: PRT
<213> ORGANISM: Artificial
<220> FEATURE:
<223> OTHER INFORMATION: LTG1927 (EF1a-CD33_4-CD8 TM-CD28-CD3 zeta-cfrag)

<400> SEQUENCE: 70

```
Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly
                20                  25                  30

Leu Val Gln Pro Gly Gly Ser Leu Arg Leu Ser Cys Ala Ala Ser Gly
            35                  40                  45

Phe Thr Phe Ser Ser Tyr Gly Met Ser Trp Val Arg Gln Ala Pro Arg
        50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Ala Thr Thr Thr Pro Ala Pro
130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Arg
        195                 200                 205

Ser Lys Arg Ser Arg Leu Leu His Ser Asp Tyr Met Asn Met Thr Pro
210                 215                 220

Arg Arg Pro Gly Pro Thr Arg Lys His Tyr Gln Pro Tyr Ala Pro Pro
225                 230                 235                 240

Arg Asp Phe Ala Ala Tyr Arg Ser Arg Val Lys Phe Ser Arg Ser Ala
                245                 250                 255

Asp Ala Pro Ala Tyr Gln Gln Gly Gln Asn Gln Leu Tyr Asn Glu Leu
            260                 265                 270

Asn Leu Gly Arg Arg Glu Glu Tyr Asp Val Leu Asp Lys Arg Arg Gly
        275                 280                 285

Arg Asp Pro Glu Met Gly Gly Lys Pro Arg Arg Lys Asn Pro Gln Glu
290                 295                 300

Gly Leu Tyr Asn Glu Leu Gln Lys Asp Lys Met Ala Glu Ala Tyr Ser
305                 310                 315                 320
```

Glu Ile Gly Met Lys Gly Glu Arg Arg Gly Lys Gly His Asp Gly
            325                 330                 335

Leu Tyr Gln Gly Leu Ser Thr Ala Thr Lys Asp Thr Tyr Asp Ala Leu
        340                 345                 350

His Met Gln Ala Leu Pro Pro Arg
        355                 360

<210> SEQ ID NO 71
<211> LENGTH: 1065
<212> TYPE: DNA
<213> ORGANISM: Artificial
<220> FEATURE:
<223> OTHER INFORMATION: LTG_D0033 (Ef1a_CD33_4 VH TNFRSF19 H_TM_CD28z

<400> SEQUENCE: 71

```
atgctgctgc tggtgaccag cctgctgctg tgcgaactgc cgcatccggc gtttctgctg      60
attccggagg tgcagctggt ggagtctggg ggaggcttgg tacagcctgg agggtccctg     120
agactctcct gtgcagcctc tggattcacc ttcagtagct atggcatgag ctgggtccgc     180
caggctccaa gacaagggct tgagtgggtg gccaacataa gcaagatgg aagtgagaaa     240
tactatgcgg actcagtgaa gggccgattc accatctcca gagacaattc caagaacacg     300
ctgtatctgc aaatgaacag cctgagagcc gaggacacag ccacgtatta ctgtgcgaaa     360
gaaaatgtgg actggggcca gggcaccctg gtcaccgtct cctcagcggc cgcagtcgga     420
ttccaagaca tggaatgcgt gccctgcggc gacccgccac ctccttacga gccgcactgc     480
gcatcgaagg tcaacctcgt gaagatcgcg agcaccgcgt cctcaccccg ggatactgct     540
ctggccgccg tgatttgttc cgccttggcc accgtgcttc tggccctgct gatcctctgt     600
gtgatccggt cgaagaggtc cagactcttg cactccgact acatgaacat gactcctaga     660
aggcccggac ccactagaaa gcactaccag ccgtacgccc ctcctcggga tttcgccgca     720
taccggtcca gagtgaagtt cagccgctca gccgatgcac cggcctacca gcagggacag     780
aaccagctct acaacgagct caacctgggt cggcgggaag aatatgacgt gctggacaaa     840
cggcgcggca gagatccgga gatgggggga agccgagga ggaagaaccc tcaagagggc     900
ctgtacaacg aactgcagaa ggacaagatg gcggaagcct actccgagat cggcatgaag     960
ggagaacgcc ggagagggaa gggtcatgac ggactgtacc agggcctgtc aactgccact    1020
aaggacactt acgatgcgct ccatatgcaa gctttgcccc cgcgg                    1065
```

<210> SEQ ID NO 72
<211> LENGTH: 355
<212> TYPE: PRT
<213> ORGANISM: Artificial
<220> FEATURE:
<223> OTHER INFORMATION: LTG_D0033 (Ef1a_CD33_4 VH TNFRSF19 H_TM_CD28z)

<400> SEQUENCE: 72

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

| | | | | | | | | | | | | | | | |
|---|---|---|---|---|---|---|---|---|---|---|---|---|---|---|---|
Gln Gly Leu Glu Trp Val Ala Asn Ile Lys Gln Asp Gly Ser Glu Lys
65 70 75 80

Tyr Tyr Ala Asp Ser Val Lys Gly Arg Phe Thr Ile Ser Arg Asp Asn
85 90 95

Ser Lys Asn Thr Leu Tyr Leu Gln Met Asn Ser Leu Arg Ala Glu Asp
100 105 110

Thr Ala Thr Tyr Tyr Cys Ala Lys Glu Asn Val Asp Trp Gly Gln Gly
115 120 125

Thr Leu Val Thr Val Ser Ser Ala Ala Val Gly Phe Gln Asp Met
130 135 140

Glu Cys Val Pro Cys Gly Asp Pro Pro Pro Tyr Glu Pro His Cys
145 150 155 160

Ala Ser Lys Val Asn Leu Val Lys Ile Ala Ser Thr Ala Ser Ser Pro
165 170 175

Arg Asp Thr Ala Leu Ala Ala Val Ile Cys Ser Ala Leu Ala Thr Val
180 185 190

Leu Leu Ala Leu Leu Ile Leu Cys Val Ile Arg Ser Lys Arg Ser Arg
195 200 205

Leu Leu His Ser Asp Tyr Met Asn Met Thr Pro Arg Arg Pro Gly Pro
210 215 220

Thr Arg Lys His Tyr Gln Pro Tyr Ala Pro Pro Arg Asp Phe Ala Ala
225 230 235 240

Tyr Arg Ser Arg Val Lys Phe Ser Arg Ser Ala Asp Ala Pro Ala Tyr
245 250 255

Gln Gln Gly Gln Asn Gln Leu Tyr Asn Glu Leu Asn Leu Gly Arg Arg
260 265 270

Glu Glu Tyr Asp Val Leu Asp Lys Arg Gly Arg Asp Pro Glu Met
275 280 285

Gly Gly Lys Pro Arg Arg Lys Asn Pro Gln Glu Gly Leu Tyr Asn Glu
290 295 300

Leu Gln Lys Asp Lys Met Ala Glu Ala Tyr Ser Glu Ile Gly Met Lys
305 310 315 320

Gly Glu Arg Arg Arg Gly Lys Gly His Asp Gly Leu Tyr Gln Gly Leu
325 330 335

Ser Thr Ala Thr Lys Asp Thr Tyr Asp Ala Leu His Met Gln Ala Leu
340 345 350

Pro Pro Arg
355

<210> SEQ ID NO 73
<211> LENGTH: 1068
<212> TYPE: DNA
<213> ORGANISM: Artificial
<220> FEATURE:
<223> OTHER INFORMATION: LTG_ D0034 (Ef1a_CD33_4 VH TNFRSF19 H_TM_4-1BBz

<400> SEQUENCE: 73
atgctgctgc tggtgaccag cctgctgctg tgcgaactgc cgcatccggc gtttctgctg      60 attccgagg tgcagctggt ggagtctggg ggaggcttgg tacagcctgg agggtccctg      120
agactctcct gtgcagcctc tggattcacc ttcagtagct atggcatgag ctgggtccgc      180
caggctccaa gacaagggct tgagtgggtg gccaacataa agcaagatgg aagtgagaaa      240
tactatgcgg actcagtgaa gggccgattc accatctcca gagacaattc caagaacacg      300
ctgtatctgc aaatgaacag cctgagagcc gaggacacag ccacgtatta ctgtgcgaaa      360

```
gaaaatgtgg actggggcca gggcaccctg gtcaccgtct cctcagcggc cgcagtcgga    420
ttccaagaca tggaatgcgt gccctgcggc gacccgccac ctccttacga gccgcactgc    480
gcatcgaagg tcaacctcgt gaagatcgcg agcaccgcgt cctcaccccg ggatactgct    540
ctggccgccg tgatttgttc cgccttggcc accgtgcttc tggccctgct gatcctctgt    600
gtgatcaaga ggggccggaa gaagctgctt tacatcttca agcagccgtt catgcggccc    660
gtgcagacga ctcaggaaga ggacggatgc tcgtgcagat ccctgaggga ggaagagggg    720
ggatgcgaac tgagagtgaa gttcagccgc tcagccgatg caccggccta ccagcaggga    780
cagaaccagc tctacaacga gctcaacctg ggtcgcggg aagaatatga cgtgctggac    840
aaacggcgcg gcagagatcc ggagatgggg ggaaagccga ggaggaagaa ccctcaagag    900
ggcctgtaca cgaactgca aaggacaag atggcggaag cctactccga gatcggcatg    960
aagggagaac gccggagagg aagggtcat gacggactgt accagggcct gtcaactgcc    1020
actaaggaca cttacgatgc gctccatatg caagctttgc ccccgcgg               1068
```

<210> SEQ ID NO 74
<211> LENGTH: 356
<212> TYPE: PRT
<213> ORGANISM: Artificial
<220> FEATURE:
<223> OTHER INFORMATION: LTG_ D0034 (Ef1a_CD33_4 VH TNFRSF19
      H_TM_4-1BBz)

<400> SEQUENCE: 74

```
Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly
                20                  25                  30

Leu Val Gln Pro Gly Gly Ser Leu Arg Leu Ser Cys Ala Ala Ser Gly
            35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Ala Val Gly Phe Gln Asp Met
    130                 135                 140

Glu Cys Val Pro Cys Gly Asp Pro Pro Pro Tyr Glu Pro His Cys
145                 150                 155                 160

Ala Ser Lys Val Asn Leu Val Lys Ile Ala Ser Thr Ala Ser Ser Pro
                165                 170                 175

Arg Asp Thr Ala Leu Ala Ala Val Ile Cys Ser Ala Leu Ala Thr Val
            180                 185                 190

Leu Leu Ala Leu Leu Ile Leu Cys Val Ile Lys Arg Gly Arg Lys Lys
        195                 200                 205

Leu Leu Tyr Ile Phe Lys Gln Pro Phe Met Arg Pro Val Gln Thr Thr
    210                 215                 220
```

```
Gln Glu Glu Asp Gly Cys Ser Cys Arg Phe Pro Glu Glu Glu Gly
225                 230                 235                 240

Gly Cys Glu Leu Arg Val Lys Phe Ser Arg Ser Ala Asp Ala Pro Ala
            245                 250                 255

Tyr Gln Gln Gly Gln Asn Gln Leu Tyr Asn Glu Leu Asn Leu Gly Arg
            260                 265                 270

Arg Glu Glu Tyr Asp Val Leu Asp Lys Arg Gly Arg Asp Pro Glu
            275                 280                 285

Met Gly Gly Lys Pro Arg Arg Lys Asn Pro Gln Glu Gly Leu Tyr Asn
290                 295                 300

Glu Leu Gln Lys Asp Lys Met Ala Glu Ala Tyr Ser Glu Ile Gly Met
305                 310                 315                 320

Lys Gly Glu Arg Arg Arg Gly Lys Gly His Asp Gly Leu Tyr Gln Gly
            325                 330                 335

Leu Ser Thr Ala Thr Lys Asp Thr Tyr Asp Ala Leu His Met Gln Ala
            340                 345                 350

Leu Pro Pro Arg
        355

<210> SEQ ID NO 75
<211> LENGTH: 2247
<212> TYPE: DNA
<213> ORGANISM: Artificial
<220> FEATURE:
<223> OTHER INFORMATION: LTG_ D0015 (Ef1a_CD33_4 VH CD8 BBz T2A tEGFR)

<400> SEQUENCE: 75
atgctgctgc tggtgaccag cctgctgctg tgcgaactgc cgcatccggc gtttctgctg      60
attccggagg tgcagctggt ggagtctggg ggaggcttgg tacagcctgg agggtccctg     120
agactctcct gtgcagcctc tggattcacc ttcagtagct atggcatgag ctgggtccgc     180
caggctccaa gacaagggct tgagtgggtg gccaacataa agcaagatgg aagtgagaaa     240
tactatgcgg actcagtgaa gggccgattc accatctcca gagacaattc caagaacacg     300
ctgtatctgc aaatgaacag cctgagagcc gaggacacag ccacgtatta ctgtgcgaaa     360
gaaaatgtgg actggggcca gggcaccctg gtcaccgtct cctcagcggc cgcaactacc     420 accccttgccc ctcggccgcc gactccggcc caaccatcg caagccaacc cctctccttg     480
cgccccgaag cttgccgccc ggccgcgggt ggagccgtgc atacccgggg ctggactttt     540
gcctgcgata tctacatttg gccccgctg ccggcactt cgcgcgtgct cctgctgtcg     600
ctggtcatca ccctttactg caagagggc cggaagaagc tgctttacat cttcaagcag     660
ccgttcatgc ggcccgtgca gacgactcag gagaggacg gatgctcgtg cagattccct     720
gaggaggaag aggggggatg cgaactgcgc gtcaagttct acggtccgc cgacgccccc     780 gcatatcaac agggccagaa tcagctctac aacgagctga acctgggaag agagaggag     840 tacgacgtgc tggacaagcg acgcggacgc gacccggaga tgggggggaa accacggcgg     900
aaaaaccctc aggaaggact gtacaacgaa ctccagaaag acaagatggc ggaagcctac     960
tcagaaatcg gatgaaggg agagcggagg agggaaagg gtcacgacgg gctgtaccag    1020
ggactgagca ccgccactaa ggatacctac gatgccttgc atatgcaagc actcccaccc    1080
cggtctagag ctaaacgctc tgggtctggt gaaggacgag gtagccttct tacgtgcgga    1140
gacgtggagg aaaacccagg accccgagcc aaacgaatgc tgctgcttgt tacaagcctt    1200
ttgctctgcg aactcccca tccagctttt ctcctgattc aaggaaggt ttgcaatgga    1260
```

-continued

```
atcggtatag gggagtttaa ggattcactt agcataaacg ctactaatat taaacacttc    1320
aaaaactgta cgagtataag tggagatctt cacattttgc cggttgcatt ccgaggcgat    1380
tcattcaccc acacgccacc gcttgaccca caagaattgg atattcttaa aaccgttaaa    1440
gaaataacgg ggttttgct cattcaagcg tggccagaaa atcgcactga cctccatgct    1500
ttcgagaacc tggagattat aagaggacga actaagcagc atggtcaatt ctcccttgct    1560
gtggtcagcc tgaacatcac cagtcttggt ttgcggtccc tcaaggaaat ttcagatgga    1620
gatgtcatca taagcggcaa caagaatttg tgctatgcaa ataccataaa ctggaaaaaa    1680
ctgtttggca cttccggcca gaaaaccaag attatttcaa atcggggtga aacagctgc     1740 aaagccaccg gccaggtttg tcatgccttg tgctctccgg aaggctgttg ggggccagaa    1800
cccagggact gcgtcagttg cagaaacgtc tcaagaggcc gcgaatgcgt tgacaagtgt    1860
aacctccttg agggtgagcc acgagagttt gttgagaaca gcgagtgtat acaatgtcac    1920
cctgaatgtt tgccccaggc tatgaatata acctgcacag gccgcgggcc tgataactgc    1980
atccagtgtg ctcattacat agatggacct cactgtgtga aaacctgccc ggccggagtt    2040
atgggagaaa acaacactct ggtgtggaaa tacgctgatg caggccacgt gtgccacctt    2100
tgtcacccga attgtacata tgggtgtacc ggtcctggac ttgaaggttg ccctaccaat    2160
ggccctaaaa tacccagtat cgcaactggc atggtaggcg ctcttctctt gctcttggta    2220
gttgctctcg gcataggtct ttttatg                                        2247
```

<210> SEQ ID NO 76
<211> LENGTH: 749
<212> TYPE: PRT
<213> ORGANISM: Artificial
<220> FEATURE:
<223> OTHER INFORMATION: LTG_ D0015 (Ef1a_CD33_4 VH CD8 BBz T2A tEGFR)

<400> SEQUENCE: 76

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Ala Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175
```

```
Gly Leu Asp Phe Ala Cys Asp Ile Tyr Ile Trp Ala Pro Leu Ala Gly
            180                 185                 190

Thr Cys Gly Val Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Gln Gln Gly Gln Asn Gln Leu Tyr Asn Glu
            260                 265                 270

Leu Asn Leu Gly Arg Arg Glu Glu Tyr Asp Val Leu Asp Lys Arg Arg
            275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Gly Lys Gly His Asp
            325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg Ser Arg Ala Lys Arg Ser Gly
            355                 360                 365

Ser Gly Glu Gly Arg Gly Ser Leu Leu Thr Cys Gly Asp Val Glu Glu
370                 375                 380

Asn Pro Gly Pro Arg Ala Lys Arg Met Leu Leu Leu Val Thr Ser Leu
385                 390                 395                 400

Leu Leu Cys Glu Leu Pro His Pro Ala Phe Leu Leu Ile Pro Arg Lys
            405                 410                 415

Val Cys Asn Gly Ile Gly Ile Gly Glu Phe Lys Asp Ser Leu Ser Ile
            420                 425                 430

Asn Ala Thr Asn Ile Lys His Phe Lys Asn Cys Thr Ser Ile Ser Gly
            435                 440                 445

Asp Leu His Ile Leu Pro Val Ala Phe Arg Gly Asp Ser Phe Thr His
            450                 455                 460

Thr Pro Pro Leu Asp Pro Gln Glu Leu Asp Ile Leu Lys Thr Val Lys
465                 470                 475                 480

Glu Ile Thr Gly Phe Leu Leu Ile Gln Ala Trp Pro Glu Asn Arg Thr
            485                 490                 495

Asp Leu His Ala Phe Glu Asn Leu Glu Ile Ile Arg Gly Arg Thr Lys
            500                 505                 510

Gln His Gly Gln Phe Ser Leu Ala Val Val Ser Leu Asn Ile Thr Ser
            515                 520                 525

Leu Gly Leu Arg Ser Leu Lys Glu Ile Ser Asp Gly Asp Val Ile Ile
            530                 535                 540

Ser Gly Asn Lys Asn Leu Cys Tyr Ala Asn Thr Ile Asn Trp Lys Lys
545                 550                 555                 560

Leu Phe Gly Thr Ser Gly Gln Lys Thr Lys Ile Ile Ser Asn Arg Gly
                565                 570                 575

Glu Asn Ser Cys Lys Ala Thr Gly Gln Val Cys His Ala Leu Cys Ser
            580                 585                 590
```

```
Pro Glu Gly Cys Trp Gly Pro Glu Pro Arg Asp Cys Val Ser Cys Arg
            595                 600                 605

Asn Val Ser Arg Gly Arg Glu Cys Val Asp Lys Cys Asn Leu Leu Glu
        610                 615                 620

Gly Glu Pro Arg Glu Phe Val Glu Asn Ser Glu Cys Ile Gln Cys His
625                 630                 635                 640

Pro Glu Cys Leu Pro Gln Ala Met Asn Ile Thr Cys Thr Gly Arg Gly
                645                 650                 655

Pro Asp Asn Cys Ile Gln Cys Ala His Tyr Ile Asp Gly Pro His Cys
            660                 665                 670

Val Lys Thr Cys Pro Ala Gly Val Met Gly Glu Asn Asn Thr Leu Val
        675                 680                 685

Trp Lys Tyr Ala Asp Ala Gly His Val Cys His Leu Cys His Pro Asn
690                 695                 700

Cys Thr Tyr Gly Cys Thr Gly Pro Gly Leu Glu Gly Cys Pro Thr Asn
705                 710                 715                 720

Gly Pro Lys Ile Pro Ser Ile Ala Thr Gly Met Val Gly Ala Leu Leu
                725                 730                 735

Leu Leu Leu Val Val Ala Leu Gly Ile Gly Leu Phe Met
            740                 745
```

<210> SEQ ID NO 77
<211> LENGTH: 2241
<212> TYPE: DNA
<213> ORGANISM: Artificial
<220> FEATURE:
<223> OTHER INFORMATION: LTG_D0016 (Ef1a CD33_4 VH CD8 28z T2A tEGFR)

<400> SEQUENCE: 77

```
atgctgctgc tggtgaccag cctgctgctg tgcgaactgc cgcatccggc gtttctgctg      60
attccggagg tgcagctggt ggagtctggg ggaggcttgg tacagcctgg agggtccctg     120
agactctcct gtgcagcctc tggattcacc ttcagtagct atggcatgag ctgggtccgc     180
caggctccaa gacaagggct gagtgggtg gccaacataa agcaagatgg aagtgagaaa     240
tactatgcgg actcagtgaa gggccgattc accatctcca gagacaattc caagaacacg     300
ctgtatctgc aaatgaacag cctgagagcc gaggacacag ccacgtatta ctgtgcgaaa     360
gaaaatgtgg actggggcca gggcaccctg gtcaccgtct cctcagcggc cgcgactacc     420
actcctgcac cacggccacc taccccagcc ccaccattgc aagccagcc actttcactg     480
cgccccgaag cgtgtagacc agctgctgga ggagccgtgc atacccgagg ctgggacttc     540
gcctgtgaca tctacatctg gcccccattg ctggaacttc gcggcgtgct gctcttgtct     600
ctggtcatta ccctgtactg ccggtcgaag aggtccagac tcttgcactc cgactacatg     660
aacatgactc ctagaaggcc cggacccact agaaagcact accagccgta cgcccctcct     720
cgggatttcg ccgcataccg gtccagagtg aagttcagcc gctcagccga tgcaccggcc     780
taccagcagg acagaaccca gctctacaac gagctcaacc tgggtcggcg ggaagaatat     840
gacgtgctgg acaaacggcg cggcagagat ccggagatgg ggggaaagcc gaggaggaag     900
aaccctcaag agggcctgta caacgaactg cagaaggaca gatggcgga agcctactcc     960
gagatcggca tgaagggaga acgccggaga gggaagggtc atgacggact gtaccagggc    1020
ctgtcaactg ccactaagga cacttacgat gcgctccata tgcaagcttt gccccgcgg    1080
agagctaaac gctctgggtc tggtgaagga cgaggtagcc ttcttacgtg cggagacgtg    1140
gaggaaaacc caggaccccg agccaaacga atgctgctgc ttgttacaag cctttgctc    1200
```

```
tgcgaactcc cccatccagc tttctcctg attccaagga aggtttgcaa tggaatcggt    1260
atagggagt ttaaggattc acttagcata aacgctacta atattaaaca cttcaaaaac    1320
tgtacgagta taagtggaga tcttcacatt ttgccggttg cattccgagg cgattcattc    1380
acccacacgc caccgcttga cccacaagaa ttggatattc ttaaaaccgt taagaaata    1440
acggggtttt tgctcattca agcgtggcca gaaaatcgca ctgacctcca tgctttcgag    1500
aacctggaga ttataagagg acgaactaag cagcatggtc aattctccct tgctgtggtc    1560
agcctgaaca tcaccagtct tggtttgcgg tccctcaagg aaatttcaga tggagatgtc    1620
atcataagcg gcaacaagaa tttgtgctat gcaaatacca taaactggaa aaaactgttt    1680
ggcacttccg ccagaaaac caagattatt tcaaatcggg gtgagaacag ctgcaaagcc    1740
accggccagg tttgtcatgc cttgtgctct ccggaaggct gttgggggcc agaacccagg    1800
gactgcgtca gttgcagaaa cgtctcaaga ggccgcgaat gcgttgacaa gtgtaacctc    1860
cttgagggtg agccacgaga gtttgttgag aacagcgagt gtatacaatg tcaccctgaa    1920
tgtttgcccc aggctatgaa tataacctgc acaggccgcg ggcctgataa ctgcatccag    1980
tgtgctcatt acatagatgg acctcactgt gtgaaaaacct gcccggccgg agttatggga    2040
gaaaacaaca ctctggtgtg gaaatacgct gatgcaggcc acgtgtgcca cctttgtcac    2100
ccgaattgta catatgggtg taccggtcct ggacttgaag gttgccctac caatggccct    2160
aaaataccca gtatcgcaac tggcatggta ggcgctcttc tcttgctctt ggtagttgct    2220
ctcggcatag gtcttttat g                                              2241

<210> SEQ ID NO 78
<211> LENGTH: 747
<212> TYPE: PRT
<213> ORGANISM: Artificial
<220> FEATURE:
<223> OTHER INFORMATION: LTG_D0016 (Ef1a CD33_4 VH CD8 28z T2A tEGFR)

<400> SEQUENCE: 78

Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Ala Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175
```

```
Gly Leu Asp Phe Ala Cys Asp Ile Tyr Ile Trp Ala Pro Leu Ala Gly
            180                 185                 190

Thr Cys Gly Val Leu Leu Ser Leu Val Ile Thr Leu Tyr Cys Arg
        195                 200                 205

Ser Lys Arg Ser Arg Leu Leu His Ser Asp Tyr Met Asn Met Thr Pro
210                 215                 220

Arg Arg Pro Gly Pro Thr Arg Lys His Tyr Gln Pro Tyr Ala Pro Pro
225                 230                 235                 240

Arg Asp Phe Ala Ala Tyr Arg Ser Arg Val Lys Phe Ser Arg Ser Ala
                245                 250                 255

Asp Ala Pro Ala Tyr Gln Gln Gly Gln Asn Gln Leu Tyr Asn Glu Leu
            260                 265                 270

Asn Leu Gly Arg Arg Glu Glu Tyr Asp Val Leu Asp Lys Arg Arg Gly
        275                 280                 285

Arg Asp Pro Glu Met Gly Gly Lys Pro Arg Arg Lys Asn Pro Gln Glu
    290                 295                 300

Gly Leu Tyr Asn Glu Leu Gln Lys Asp Lys Met Ala Glu Ala Tyr Ser
305                 310                 315                 320

Glu Ile Gly Met Lys Gly Glu Arg Arg Arg Gly Lys Gly His Asp Gly
                325                 330                 335

Leu Tyr Gln Gly Leu Ser Thr Ala Thr Lys Asp Thr Tyr Asp Ala Leu
            340                 345                 350

His Met Gln Ala Leu Pro Pro Arg Arg Ala Lys Arg Ser Gly Ser Gly
        355                 360                 365

Glu Gly Arg Gly Ser Leu Leu Thr Cys Gly Asp Val Glu Glu Asn Pro
    370                 375                 380

Gly Pro Arg Ala Lys Arg Met Leu Leu Leu Val Thr Ser Leu Leu Leu
385                 390                 395                 400

Cys Glu Leu Pro His Pro Ala Phe Leu Leu Ile Pro Arg Lys Val Cys
                405                 410                 415

Asn Gly Ile Gly Ile Gly Glu Phe Lys Asp Ser Leu Ser Ile Asn Ala
            420                 425                 430

Thr Asn Ile Lys His Phe Lys Asn Cys Thr Ser Ile Ser Gly Asp Leu
        435                 440                 445

His Ile Leu Pro Val Ala Phe Arg Gly Asp Ser Phe Thr His Thr Pro
    450                 455                 460

Pro Leu Asp Pro Gln Glu Leu Asp Ile Leu Lys Thr Val Lys Glu Ile
465                 470                 475                 480

Thr Gly Phe Leu Leu Ile Gln Ala Trp Pro Glu Asn Arg Thr Asp Leu
                485                 490                 495

His Ala Phe Glu Asn Leu Glu Ile Ile Arg Gly Arg Thr Lys Gln His
            500                 505                 510

Gly Gln Phe Ser Leu Ala Val Val Ser Leu Asn Ile Thr Ser Leu Gly
        515                 520                 525

Leu Arg Ser Leu Lys Glu Ile Ser Asp Gly Asp Val Ile Ile Ser Gly
    530                 535                 540

Asn Lys Asn Leu Cys Tyr Ala Asn Thr Ile Asn Trp Lys Lys Leu Phe
545                 550                 555                 560

Gly Thr Ser Gly Gln Lys Thr Lys Ile Ile Ser Asn Arg Gly Glu Asn
                565                 570                 575

Ser Cys Lys Ala Thr Gly Gln Val Cys His Ala Leu Cys Ser Pro Glu
            580                 585                 590
```

```
Gly Cys Trp Gly Pro Glu Pro Arg Asp Cys Val Ser Cys Arg Asn Val
            595                 600                 605

Ser Arg Gly Arg Glu Cys Val Asp Lys Cys Asn Leu Leu Glu Gly Glu
        610                 615                 620

Pro Arg Glu Phe Val Glu Asn Ser Glu Cys Ile Gln Cys His Pro Glu
625                 630                 635                 640

Cys Leu Pro Gln Ala Met Asn Ile Thr Cys Thr Gly Arg Gly Pro Asp
                645                 650                 655

Asn Cys Ile Gln Cys Ala His Tyr Ile Asp Gly Pro His Cys Val Lys
            660                 665                 670

Thr Cys Pro Ala Gly Val Met Gly Glu Asn Asn Thr Leu Val Trp Lys
        675                 680                 685

Tyr Ala Asp Ala Gly His Val Cys His Leu Cys His Pro Asn Cys Thr
690                 695                 700

Tyr Gly Cys Thr Gly Pro Gly Leu Glu Gly Cys Pro Thr Asn Gly Pro
705                 710                 715                 720

Lys Ile Pro Ser Ile Ala Thr Gly Met Val Gly Ala Leu Leu Leu Leu
                725                 730                 735

Leu Val Val Ala Leu Gly Ile Gly Leu Phe Met
            740                 745
```

```
<210> SEQ ID NO 79
<211> LENGTH: 36
<212> TYPE: DNA
<213> ORGANISM: Homo sapiens

<400> SEQUENCE: 79
gagagcaaat acgggccgcc atgtccccg tgtccg                              36

<210> SEQ ID NO 80
<211> LENGTH: 12
<212> TYPE: PRT
<213> ORGANISM: Homo sapiens

<400> SEQUENCE: 80

Glu Ser Lys Tyr Gly Pro Pro Cys Pro Pro Cys Pro
1               5                   10

<210> SEQ ID NO 81
<211> LENGTH: 327
<212> TYPE: DNA
<213> ORGANISM: Homo sapiens

<400> SEQUENCE: 81
gcaccaccag ttgctggccc tagtgtcttc ttgttccctc ccaagcccaa agacaccttg      60
atgatttcca gaactcctga ggttacctgc gttgtcgtag atgtttctca ggaggaccca     120
gaggtccaat taactggta cgttgatggg gtggaagttc acaatgcgaa gacaaagccg     180
cgggaagaac aatttcagtc cacttaccgg gttgtcagcg ttctgacggt attgcatcaa     240
gactggctta atggaaagga atataagtgt aaggtgtcca acaaaggttt gccgagcagt     300
attgagaaga ccatatcaaa ggcgaag                                         327

<210> SEQ ID NO 82
<211> LENGTH: 109
<212> TYPE: PRT
<213> ORGANISM: Homo sapiens
```

<400> SEQUENCE: 82

Ala Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Gln Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys
                100                 105

<210> SEQ ID NO 83
<211> LENGTH: 321
<212> TYPE: DNA
<213> ORGANISM: Homo sapiens

<400> SEQUENCE: 83
gggcagccgc gcgagccaca agtttacact tgccgccat ctcaagagga aatgactaaa      60
aaccaggtat ccttgacatg cctcgtaaaa ggatttatc catctgatat tgctgtggaa     120
tgggagtcta acgggcagcc ggaaaataat tacaaaacta caccacctgt gctcgattca    180
gatggaagtt tcttcctta cagtagactt acggtggaca atctaggtg caggaaggg     240 aatgtgttta gttgtagtgt aatgcacgag gcacttcata accactatac acagaagtca    300
ctgagtttga gtcttggcaa a                                              321

<210> SEQ ID NO 84
<211> LENGTH: 107
<212> TYPE: PRT
<213> ORGANISM: Homo sapiens

<400> SEQUENCE: 84

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
                100                 105

<210> SEQ ID NO 85
<211> LENGTH: 684
<212> TYPE: DNA
<213> ORGANISM: Homo sapiens

```
<400> SEQUENCE: 85
gagagcaaat acgggccgcc atgtcccccg tgtccggcac caccagttgc tggccctagt      60
gtcttcttgt tccctcccaa gcccaaagac accttgatga tttccagaac tcctgaggtt     120
acctgcgttg tcgtagatgt ttctcaggag gacccagagg tccaatttaa ctggtacgtt     180
gatgggtgg  aagttcacaa tgcgaagaca aagccgcggg aagaacaatt tcagtccact     240
taccgggttg tcagcgttct gacggtattg catcaagact ggcttaatgg aaaggaatat     300
aagtgtaagg tgtccaacaa aggtttgccg agcagtattg agaagaccat atcaaaggcg     360
aagggggcagc cgcgcgagcc acaagtttac actttgccgc catctcaaga ggaaatgact     420
aaaaaccagg tatccttgac atgcctcgta aaaggatttt atccatctga tattgctgtg     480
gaatgggagt ctaacgggca gccggaaaat aattacaaaa ctacaccacc tgtgctcgat     540
tcagatggaa gtttcttcct ttacagtaga cttacggtgg acaaatctag gtggcaggaa     600
gggaatgtgt ttagttgtag tgtaatgcac gaggcacttc ataaccacta tacacagaag     660
tcactgagtt tgagtcttgg caaa                                            684
```

<210> SEQ ID NO 86
<211> LENGTH: 228
<212> TYPE: PRT
<213> ORGANISM: Homo sapiens

<400> SEQUENCE: 86

```
Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225
```

<210> SEQ ID NO 87
<211> LENGTH: 1629
<212> TYPE: DNA
<213> ORGANISM: Artificial
<220> FEATURE:
<223> OTHER INFORMATION: LTG_D0035 (Ef1a_CD33_4 VH H CH2 CH3
      IgG4_CD8TM_CD28z)

<400> SEQUENCE: 87

```
atgctgctgc tggtgaccag cctgctgctg tgcgaactgc cgcatccggc gtttctgctg      60
attccggagg tgcagctggt ggagtctggg ggaggcttgg tacagcctgg agggtccctg     120
agactctcct gtgcagcctc tggattcacc ttcagtagct atggcatgag ctgggtccgc     180
caggctccaa gacaagggct tgagtgggtg gccaacataa agcaagatgg aagtgagaaa     240
tactatgcgg actcagtgaa gggccgattc accatctcca gagacaattc caagaacacg     300
ctgtatctgc aaatgaacag cctgagagcc gaggacacag ccacgtatta ctgtgcgaaa     360
gaaaatgtgg actggggcca gggcacccctg gtcaccgtct cctcagcggc cgcagagagc     420
aaatacgggc cgccatgtcc cccgtgtccg gcaccaccag ttgctggccc tagtgtcttc     480
ttgttccctc ccaagcccaa agacaccttg atgatttcca gaactcctga ggttacctgc     540
gttgtcgtag atgtttctca ggaggaccca gaggtccaat taactggta cgttgatggg     600 gtggaagttc acaatgcgaa gacaaagccg cgggaagaac aatttcagtc cacttaccgg     660
gttgtcagcg ttctgacggt attgcatcaa gactggctta atggaaagga atataagtgt     720
aaggtgtcca caaaggtttt gccgagcagt attgagaaga ccatatcaaa ggcgaagggg     780
cagccgcgcg agccacaagt ttacactttg ccgccatctc aagaggaaat gactaaaaac     840
caggtatcct tgacatgcct cgtaaaagga ttttatccat ctgatattgc tgtggaatgg     900
gagtctaacg ggcagccgga aaataattac aaaactacac acctgtgct cgattcagat     960 ggaagttct cctttacag tagacttacg gtggacaaat ctaggtggca ggaagggaat    1020
gtgtttagtt gtagtgtaat gcacgaggca cttcataacc actatacaca gaagtcactg    1080
agtttgagtc ttggcaaaat ctacatctgg gcgcccttgg ccgggacttg tggggtcctt    1140
ctcctgtcac tggttatcac cctttactgc cggtcgaaga ggtccagact cttgcactcc    1200
gactacatga acatgactcc tagaaggccc ggacccacta gaaagcacta ccagccgtac    1260
gcccctcctc gggatttcgc cgcataccgg tccagagtga agttcagccg ctcagccgat    1320
gcaccggcct accagcaggg acagaaccag ctctacaacg agctcaacct gggtcggcgg    1380
gaagaatatg acgtgctgga caaacggcgc ggcagagatc cggagatggg gggaaagccg    1440
aggaggaaga accctcaaga gggcctgtac aacgaactgc agaaggacaa gatggcggaa    1500
gcctactccg agatcggcat gaagggagaa cgccggagag ggaagggtca tgacggactg    1560
taccagggcc tgtcaactgc cactaaggac acttacgatg cgctccatat gcaagctttg    1620
ccccgcgg                                                              1629
```

<210> SEQ ID NO 88
<211> LENGTH: 543
<212> TYPE: PRT
<213> ORGANISM: Artificial
<220> FEATURE:
<223> OTHER INFORMATION: LTG_D0035 (Ef1a_CD33_4 VH H CH2 CH3
      IgG4_CD8TM_CD28z)

<400> SEQUENCE: 88

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Ala Glu Ser Lys Tyr Gly Pro
    130                 135                 140

Pro Cys Pro Pro Cys Pro Ala Pro Pro Val Ala Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser Gln Glu Asp Pro Glu Val
            180                 185                 190

Gln Phe Asn Trp Tyr Val Asp Gly Val Glu Val His Asn Ala Lys Thr
        195                 200                 205

Lys Pro Arg Glu Glu Gln Phe Gln Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Gly Leu Pro Ser Ser Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Gln Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Arg Leu Thr Val Asp Lys Ser Arg Trp
                325                 330                 335

Gln Glu Gly Asn Val Phe Ser Cys Ser Val Met His Glu Ala Leu His
            340                 345                 350

Asn His Tyr Thr Gln Lys Ser Leu Ser Leu Ser Leu Gly Lys Ile Tyr
        355                 360                 365

Ile Trp Ala Pro Leu Ala Gly Thr Cys Gly Val Leu Leu Leu Ser Leu
    370                 375                 380

Val Ile Thr Leu Tyr Cys Arg Ser Lys Arg Ser Arg Leu Leu His Ser
385                 390                 395                 400
```

```
Asp Tyr Met Asn Met Thr Pro Arg Arg Pro Gly Pro Thr Arg Lys His
                405                 410                 415
Tyr Gln Pro Tyr Ala Pro Pro Arg Asp Phe Ala Ala Tyr Arg Ser Arg
            420                 425                 430
Val Lys Phe Ser Arg Ser Ala Asp Ala Pro Ala Tyr Gln Gln Gly Gln
        435                 440                 445
Asn Gln Leu Tyr Asn Glu Leu Asn Leu Gly Arg Arg Glu Glu Tyr Asp
    450                 455                 460
Val Leu Asp Lys Arg Arg Gly Arg Asp Pro Glu Met Gly Gly Lys Pro
465                 470                 475                 480
Arg Arg Lys Asn Pro Gln Glu Gly Leu Tyr Asn Glu Leu Gln Lys Asp
            485                 490                 495
Lys Met Ala Glu Ala Tyr Ser Glu Ile Gly Met Lys Gly Glu Arg Arg
                500                 505                 510
Arg Gly Lys Gly His Asp Gly Leu Tyr Gln Gly Leu Ser Thr Ala Thr
            515                 520                 525
Lys Asp Thr Tyr Asp Ala Leu His Met Gln Ala Leu Pro Pro Arg
    530                 535                 540
```

COMPOSITIONS AND METHODS FOR TREATING CANCER WITH ANTI-CD33 IMMUNOTHERAPY

CROSS-REFERENCE TO RELATED APPLICATIONS

This application is a divisional application and claims priority to U.S. patent application Ser. No. 15/934,770, filed Mar. 23, 2018, issued as U.S. Pat. No. 10,426,797, which claims the benefit of priority under 35 U.S.C. Section 119(e) to U.S. Provisional Patent Application No. 62/620,139, filed Jan. 22, 2018, and U.S. Provisional Patent Application No. 62/476,438 filed on Mar. 24, 2017, the entire contents of which are incorporated herein by reference.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing which has been submitted electronically in ASCII format and is hereby incorporated by reference in its entirety. Said ASCII copy, created on Mar. 20, 2018, is named Sequence Listing.txt and is 124 kilobytes in size.

FIELD OF THE DISCLOSURE

This application relates to the field of cancer, particularly to CD33 antigen binding domains and chimeric antigen receptors (CARs) containing such CD33 antigen binding domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

CD33 is a 67 kDa transmembrane cell surface glycoprotein receptor. CD33 is a member of sialic acid-binding immunoglobulin-like lectins (SIGLEC) family. Proteins in this family mediate adhesion of leukocytes to endothelial cells by binding sialylated glycans. (Kelm S, Schauer R, Crocker P R. Glycoconj J. 1996; 13:913-926). In addition, CD33 functions as an inhibitory receptor through immunoreceptor tyrosine-based inhibitory motifs (ITIMs). CD33 receptor activation leads to phosphorylation of two tyrosines (Y340 and Y358) in CD33 cytoplasmic tail, which serves as a docking site for SHP phosphatases, and is involved in inhibitory signal transduction cascades, such as downregulation of calcium mobilization (Paul SP1, Taylor L S, Stansbury E K, McVicar D W Blood. 2000 Jul. 15; 96(2): 483-90).

CD33 is a myeloid lineage differentiation antigen, and it is highly expressed on myeloid progenitor cells (Andrews R G, Torok-Storb B, Bernstein ID. Blood. 1983; 62:124-132), but is only expressed at low levels in differentiated myeloid cells, namely macrophages and granulocytes (Simmons D, Seed B. J Immunol. 1988; 141:2797-2800). By contrast, CD33 has been reported to be expressed on 87.8%-99% of acute myeloblastic leukemias (AML) (A Ehningerl et al. Blood Cancer Journal (2014) 4, e218; Christina Krupka et al. Blood 2014 123:356-365). AML is a devastating disease, with 5-year survival rate of approximately 26% (available on the world wide web at cancer.net/cancer-types/leukemia-acute-myeloid-aml/statistics). The present standard of care for AML consists of remission induction treatment by high dose of chemotherapy or radiation, followed by consolidation, comprised of allogeneic stem cell transplantation and additional courses of chemotherapy as needed (available on the world wide web at cancer.org/cancer/acute-myeloid-leukemia/treating/typical-treatment-of-aml.html). High toxicity associated with this treatment, as well as the risk of complications, such as myelosuppression or GVHD, motivate the search for better therapeutic alternatives.

A number of novel approaches to treat AML, including antibody-drug conjugates (SGN-CD33A, Vadastuximab Talirine, Stein A. S. et al. (2015). Blood, 126(23), 324; Phase I-II clinical trial NCT02706899), a bispecific T-cell-engaging antibody (AMG330, Laszlo G S et al. Blood 2013:123 (4):554-561, NCT02520427), and CART-33 cells (Wang Q S et al. Mol Ther. 2015 January; 23(1):184-91, NCT01864902) are currently being investigated. However, several of the novel approaches have been held back due to clinical toxicity. Seattle Genetics Phase I clinical trials testing SGN-CD33 drug were recently put on hold due to risk of hepatotoxicity (available on the world wide web at businesswire.com/news/home/20161227005087/en/Seattle-Genetics-Announces-Clinical-Hold-Phase-1). Gemtuzumab ozogamicin (Mylotarg, Pfizer/Wyeth) was voluntarily withdrawn from the market by the manufacturer in 2010, following incidence of potentially fatal veno-occlusive liver disease observed in a post-marketing clinical trial (Jacob M. Rowe and Bob Löwenberg Blood 2013 121:4838-4841). Despite recent reintroduction of Mylotarg by FDA for CD33+ adult AML, and for relapsed/refractory pediatric AML, new, more conservative lower dosage and new regiments have been prescribed for this drug (FDA press release September 2017, available on the world wide web at fda.gov). The efficacy of this treatment, the durability of patients' responses to Mylotarg, instances of tumor antigen escape and its safety profile under the new regiments remain to be determined. Therefore, the need for safe efficacious and durable treatments for AML remains imminent.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after an single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al Clin Cancer Res. 2012; 18(8):2199-209; Lehner M et al. PLoS One. 2012; 7 (2):e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARS that are in a second generation CD28/CD3-ζ (Lee D W et al. American Society of Hematology Annual Meeting. New Orleans, La.; December 7-10, 2013) and a CD137/CD3-ζsignaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3- and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single ScFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations. (Hegde M et al. Mol Ther. 2013; 21(11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-0 by the expression of a decoy receptor further demonstrates that degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. A number of antibody-based modalities targeting CD33-positive tumors are currently in development, including an anti-CD33 antibody-drug conjugate (Stein A. S. et al. Blood, 2015, 126(23), 324), a bispecific T cell engager (BiTE), (Laszlo G S et al. Blood 2013:123(4):554-561), and CART cells (Wang Q S et al. Mol Ther. 2015 January; 23(1):184-91). Recent work in pre-clinical models of AML has shown that lysis of CD33 positive AML blasts and tumor cell lines by CD33-targeting modalities can be achieved in vitro and in vivo, however a number of challenges to this approach became apparent in the clinical context, including treatment-associated toxicity (available on the world wide web at businesswire.com/news/home/20161227005087/en/Seattle-Genetics-Announces-Clinical-Hold-Phase-1; Rowe J M and Löwenberg B, Blood 2013 121:4838-4841, Wang Q S et al. Mol Ther. 2015 January; 23(1):184-91, NCT01864902) and suboptimal efficacy, (Walter R B, et al. Blood. 2012; 119(26): 6198-6208; Cowan A J, et al. Biosci 2013; 18(4):1311-1334). Moreover, in BiTEs-based approach, the reliance upon high-density CD33 antigen expression and the need for additional T cell co-stimulation/checkpoint blockage for optimal BiTE function remain a challenge (Laszlo G S et al. Blood. 2014; 123(4):554-56, Laszlo G S et al. *Blood Cancer Journal* (2015) 5, e340). Accordingly, there is an urgent and long felt need in the art for discovering novel compositions and methods for treatment of AML using an approach that can exhibit specific and efficacious anti-tumor effect without the aforementioned short comings.

The present invention addresses these needs by providing CAR compositions and therapeutic methods that can be used to treat cancers and other diseases and/or conditions. In particular, the present invention as disclosed and described herein provides CARs that may be used the treatment of diseases, disorders or conditions associated with dysregulated expression of CD33 and which CARs contain CD33 antigen binding domains that exhibit a high surface expression on transduced T cells, exhibit a high degree of cytolysis and transduced T cell in vivo expansion and persistence.

SUMMARY

Novel anti-CD33 antibodies or antigen binding domains thereof and chimeric antigen receptors (CARs) that contain such CD33 antigen binding domains are provided herein, as well as host cells (e.g., T cells) expressing the receptors, and nucleic acid molecules encoding the receptors. CAR may consist either of a single molecule expressed on the effector cell surface, or a CAR comprised of an effector cell-expressed signaling module and a soluble targeting module, such as when the soluble targeting module binds to the cell-expressed signaling module, a complete functional CAR is formed. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

Thus, in one aspect, an isolated polynucleotide encoding a human anti-CD33 antibody or a fragment thereof is provided comprising a nucleic acid sequence selected from the group consisting of SEQ ID NOs: 1, 3, 5, 7, 9, and 11.

In one embodiment, an isolated polynucleotide encoding a fully human anti-CD33 antibody or a fragment thereof is provided, wherein the antibody or a fragment thereof comprises a fragment selected from the group consisting of an Fab fragment, an F(ab')2 fragment, an Fv fragment, and a single chain Fv (ScFv).

In one embodiment, an isolated polynucleotide encoding a fully human anti-CD33 antibody or a fragment thereof is provided, wherein the antibody or a fragment thereof comprises an amino acid sequence selected from the group consisting of SEQ ID NOs: 2, 4, 6, 8, 10, and 12.

In one aspect, an isolated nucleic acid molecule encoding a chimeric antigen receptor (CAR) is provided comprising, from N-terminus to C-terminus, at least one CD33 antigen binding domain encoded by a nucleotide sequence comprising a nucleic acid sequence selected from the group consisting of SEQ ID NOs: 1, 3, 5, 7, 9, and 11, at least one transmembrane domain, and at least one intracellular signaling domain.

In one embodiment, an isolated nucleic acid molecule encoding the CAR is provided wherein the encoded extracellular CD33 antigen binding domain comprises at least one single chain variable fragment of an antibody that binds to CD33.

In another embodiment, an isolated nucleic acid molecule encoding the CAR is provided wherein the encoded extracellular CD33 antigen binding domain comprises at least one heavy chain variable region of an antibody that binds to CD33.

In one embodiment, the targeting domain of the CAR is expressed separately in the form of monoclonal antibody, ScFv Fab, Fab'2 and is containing an antigen-targeting domain comprising a nucleic acid sequence selected from the group consisting of SEQ ID NOs: 1, 3, 5, 7, 9, and 11, coupled to an additional binding tag or epitope, whereas the effector-cell expressed component of the CAR contains a binding domain specifically directed to bind the tag or epitope expressed on the soluble CAR module, such as specific binding on the soluble component of the CAR to the cell bound component of the CAR forms the full functional CAR structure.

In another embodiment, the targeting domain of the CAR is expressed separately in the form of a monoclonal antibody, ScFv Fab, Fab'2 and contains an antigen-targeting domain comprising a nucleic acid sequence selected from the group consisting of SEQ ID NOs: 1, 3, 5, 7, 9, and 11, and an additional scFv, whereas the effector-cell expressed component of the CAR contains a tag or epitope specifically reactive with the additional scFv expressed on the soluble CAR module, such as specific binding on the soluble component of the CAR to the cell bound component of the CAR forms the full functional CAR structure.

In yet another embodiment, an isolated nucleic acid molecule encoding the CAR is provided wherein the encoded CAR extracellular CD33 antigen binding domain further comprises at least one lipocalin-based antigen binding antigen (anticalins) that binds to CD33.

In one embodiment, an isolated nucleic acid molecule is provided wherein the encoded extracellular CD33 antigen binding domain is connected to the transmembrane domain by a linker domain.

In another embodiment, an isolated nucleic acid molecule encoding the CAR is provided wherein the encoded CD33 extracellular antigen binding domain is preceded by a sequence encoding a leader or signal peptide.

In yet another embodiment, an isolated nucleic acid molecule encoding the CAR is provided comprising at least one CD33 antigen binding domain encoded by a nucleotide sequence comprising a nucleic acid sequence selected from the group consisting of SEQ ID NOs: 1, 3, 5, 7, 9, and 11, and wherein the CAR additionally encodes an extracellular antigen binding domain targets an antigen that includes, but is not limited to, CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular CD33 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 13, SEQ ID NO: 39, SEQ ID NO: 41, or SEQ ID NO: 43.

In yet another embodiment, an isolated nucleic acid molecule encoding the CAR is provided wherein the encoded leader sequence comprises the amino acid sequence of SEQ ID NO: 14 SEQ ID NO: 40, SEQ ID NO: 42, or SEQ ID NO: 44.

In one aspect, a chimeric antigen receptor (CAR) is provided herein comprising, from N-terminus to C-terminus, at least one CD33 antigen binding domain, at least one transmembrane domain, and at least one intracellular signaling domain.

In one embodiment, a CAR is provided wherein the extracellular CD33 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In some embodiments, the CAR is provided wherein CAR additionally encodes an extracellular antigen binding domain comprising CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, the CAR is provided wherein the extracellular antigen binding domain comprises an immunoglobulin variable heavy chain only (VH) anti-CD19 antigen binding domain, an anti-CD20 VH antigen binding domain, an anti-CD22 VH antigen binding domain, an anti-ROR1 VH antigen binding domain, an anti-mesothelin VH antigen binding domain, an anti-CD33 VH antigen binding domain, an anti-CD38 VH antigen binding domain, an anti-CD123 (IL3RA) VH antigen binding domain, an anti-CD138 VH antigen binding domain, an anti-BCMA (CD269) VH antigen binding domain, an anti-GPC2 VH antigen binding domain, an anti-GPC3 VH antigen binding domain, an anti-FGFR4 VH antigen binding domain, an anti-c-Met VH antigen binding domain, an anti-PMSA VH antigen binding domain, an anti-glycolipid F77 VH antigen binding domain, an anti-EGFRvIII VH antigen binding domain, an anti-GD-2 VH antigen binding domain, an anti-NY-ESO-1 TCR VH antigen binding domain, an anti-MAGE A3 TCR VH antigen binding domain, or an amino acid sequence with 85%, 90%, 95%, 96%, 97%, 98% or 99% identity thereof, or any combination thereof.

In another embodiment, the CAR is provided wherein the extracellular antigen binding domain comprises a protein or a peptide (P) sequence capable of specifically binding target antigen, which may be derived from a natural or a synthetic sequence comprising anti-CD19 P antigen binding domain, an anti-CD20 P antigen binding domain, an anti-CD22 P antigen binding domain, an anti-ROR1 P antigen binding domain, an anti-mesothelin P antigen binding domain, an anti-CD33 P antigen binding domain, an anti-CD38 P antigen binding domain, an anti-CD123 (IL3RA) P antigen binding domain, an anti-CD138 P antigen binding domain, an anti-BCMA (CD269) P antigen binding domain, an anti-GPC2 P antigen binding domain, an anti-GPC3 P antigen binding domain, an anti-FGFR4 P antigen binding domain, an anti-c-Met P antigen binding domain, an anti-PMSA P antigen binding domain, an anti-glycolipid F77 P antigen binding domain, an anti-EGFRvIII P antigen binding domain, an anti-GD-2 P antigen binding domain, an anti-NY-ESO-1 TCR P antigen binding domain, an anti-MAGE A3 TCR P antigen binding domain, or an amino acid sequence with 85%, 90%, 95%, 96%, 97%, 98% or 99% identity thereof, or any combination thereof. In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 15 (LTG 1905 EF1a VH-2 CD33-CD8 TM-41BB-CD3 zeta nucleic acid sequence (FIG. 2A)). In one embodiment, the nucleic acid sequence encodes a CAR comprising the amino acid sequence of SEQ ID NO: 16 (LTG 1905 EF1a VH-2 CD33-CD8 TM-41BB-CD3 zeta amino acid sequence (FIG. 2A)).

In another embodiment, the nucleic acid sequence encoding a CAR comprises the nucleic acid sequence of SEQ ID NO: 17 (LTG 1906 EF1a-VH-4 CD33-CD8 TM-41BB-CD3 zeta nucleic acid sequence (FIG. 2B)). In one embodiment, the nucleic acid sequence encodes a CAR comprising the amino acid sequence of SEQ ID NO: 18 (LTG 1906 EF1a-VH-4 CD33-CD8 TM-41BB-CD3 zeta amino acid sequence (FIG. 2B)).

In another embodiment, the nucleic acid sequence encoding a CAR comprises the nucleic acid sequence of SEQ ID NO: 19 (LTG1936 EF1a ScFv9 CD33 CD8 TM-41BB-CD3 zeta CAR nucleotide sequence (FIG. 2C)). In one embodiment, the nucleic acid sequence encodes a CAR comprising the amino acid sequence of SEQ ID NO: 20 (LTG1936 EF1a ScFv9 CD33 CD8 TM-41BB-CD3 zeta CAR amino acid sequence (FIG. 2C)).

In another embodiment, the nucleic acid sequence encoding a CAR comprises the nucleic acid sequence of SEQ ID NO: 21 (LTG1937 EF1a ScFv10 CD33 CD8 TM-41BB-CD3 zeta nucleic acid sequence (FIG. 2D)). In one embodiment, the nucleic acid sequence encodes a CAR comprising the amino acid sequence of SEQ ID NO: 22 (LTG1937 EF1a ScFv10 CD33 CD8 TM-41BB-CD3 amino acid sequence (FIG. 2D)).

In another embodiment, the nucleic acid sequence encoding a CAR comprises the nucleic acid sequence of SEQ ID NO: 23 (LTG1938 EF1a ScFv12 CD33 CD8 TM-41BB-CD3 zeta nucleic acid sequence (FIG. 2E)). In one embodiment, the nucleic acid sequence encodes a CAR comprising the amino acid sequence of SEQ ID NO: 24 LTG1938 EF1a ScFv12 CD33 CD8 TM-41BB-CD3 zeta amino acid sequence (FIG. 2E)).

In another embodiment, the nucleic acid sequence encoding a CAR comprises the nucleic acid sequence of SEQ ID NO: 25 (LTG1939 EF1a ScFv15 CD33 CD8 TM-41BB-CD3 zeta nucleic acid sequence (FIG. 2F)). In one embodiment, the nucleic acid sequence encodes a CAR comprising the amino acid sequence of SEQ ID NO: 26 (LTG1939 EF1a ScFv15 CD33 CD8 TM-41BB-CD3 zeta amino acid sequence (FIG. 2F)).

In another embodiment, the nucleic acid sequence encoding a CAR comprises the nucleic acid sequence of SEQ ID NO: 69 (LTG1927 EF1a-CD33_4 CD8 TM-CD28-CD3 zeta nucleic acid sequence (FIG. 12A)). In one embodiment, the nucleic acid sequence encodes a CAR comprising the amino acid sequence of SEQ ID NO: 70 (LTG1927 EF1a-CD33_4 CD8 TM-CD28-CD3 zeta amino acid sequence (FIG. 12A)).

In another embodiment, the nucleic acid sequence encoding a CAR comprises the nucleic acid sequence of SEQ ID NO: 71 (LTG_D0033 Ef1a-CD33_4 VH TNFRSF19H_TM_CD28z nucleic acid sequence (FIG. 12B)). In one embodiment, the nucleic acid sequence encodes a CAR comprising the amino acid sequence of SEQ ID NO: 72 (LTG_D0033 (Ef1a-CD33_4 VH TNFRSF19H_TM_CD28z) amino acid sequence (FIG. 12B)).

In another embodiment, the nucleic acid sequence encoding a CAR comprises the nucleic acid sequence of SEQ ID NO: 73 (LTG_D0034 Ef1a-CD33_4 VH TNFRSF19H_TM 4-1BBz nucleic acid sequence (FIG. 12C)). In one embodiment, the nucleic acid sequence encodes a CAR comprising the amino acid sequence of SEQ ID NO: 74 (LTG_D0034 Ef1a-CD33_4 VH TNFRSF19H_TM_4-1BBz amino acid sequence (FIG. 12C)).

In another embodiment, the nucleic acid sequence encoding a CAR comprises the nucleic acid sequence of SEQ ID NO: 87 (LTG_D0035 Ef1a CD33_4 VH H CH2 CH3 IgG4_CD8TM_CD28z nucleic acid sequence (FIG. 12F)). In one embodiment, the nucleic acid sequence encodes a CAR comprising the amino acid sequence of SEQ ID NO: 88 (LTG_D0035 Ef1a CD33_4 VH H CH2 CH3 IgG4_CD8TM_CD28z amino acid sequence (FIG. 12F)).

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid sequence encoding a CAR comprises the nucleic acid sequence of SEQ ID NO: 75 (LTG_D0015 Ef1a-CD33_4 VH CD8 BBz T2A tEGFR nucleic acid sequence (FIG. 12D)). In one embodiment, the nucleic acid sequence encodes a CAR comprising the amino acid sequence of SEQ ID NO: 76 (LTG_D0015 Ef1a-CD33_4 VH CD8 BBz T2A tEGFR amino acid sequence (FIG. 12D)).

In another embodiment, the nucleic acid sequence encoding a CAR comprises the nucleic acid sequence of SEQ ID NO: 77 (LTG_D0016 Ef1a-CD33_4 VH CD8 28z T2A tEGFR nucleic acid sequence (FIG. 12E)). In one embodiment, the nucleic acid sequence encodes a CAR comprising the amino acid sequence of SEQ ID NO: 78 (LTG_D0015 Ef1a-CD33_4 VH CD8 28z T2A tEGFR amino acid sequence (FIG. 12E)).

In one embodiment, the nucleic acid molecule encoding the disclosed CARS can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8$^+$ T cell.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain comprising a CD33 antigen binding domain comprising the amino acid sequence of SEQ ID NO. 2, 4, 6, 8, 10, and 12, at least one linker domain, at least one transmembrane domain, and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds CD33, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In yet another aspect, a method for diagnosing a disease, disorder or condition associated with the expression of CD33 on a cell, is provided comprising a) contacting the cell with a human anti-CD33 antibody or fragment thereof, wherein the antibody or a fragment thereof comprises an amino acid sequence selected from the group consisting of SEQ ID NOs: 2, 4, 6, 8, 10, and 12; and b) detecting the presence of CD33 wherein the presence of CD33 diagnoses for the disease, disorder or condition associated with the expression of CD33.

In one embodiment, the disease, disorder or condition associated with the expression of CD33 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of a CD33-related disease in a mammal, is provided comprising detecting the expression of CD33 in a sample derived from the mammal comprising: a) contacting the sample with a human anti-CD33 antibody or fragment thereof, wherein the antibody or a fragment thereof comprises an amino acid sequence selected from the group consisting of SEQ ID NOs: 2, 4, 6, 8, 10, and 12; and b) detecting the presence of CD33 wherein the presence of CD33 diagnoses for a CD33-related disease in the mammal.

In another embodiment, a method of inhibiting CD33-dependent T cell inhibition, is provided comprising contacting a cell with a human anti-CD33 antibody or fragment thereof, wherein the antibody or a fragment thereof comprises an amino acid sequence selected from the group consisting of SEQ ID NOs: 2, 4, 6, 8, 10, and 12. In one embodiment, the cell is selected from the group consisting of a CD33-expressing tumor cell, a tumor-associated macrophage, and any combination thereof.

In another embodiment, a method of blocking T-cell inhibition mediated by a CD33-expressing cell and altering the tumor microenvironment to inhibit tumor growth in a mammal, is provided comprising administering to the mammal an effective amount of a composition comprising an isolated anti-CD33 antibody or fragment thereof, wherein the antibody or a fragment thereof comprises an amino acid sequence selected from the group consisting of SEQ ID NOs: 2, 4, 6, 8, 10, and 12. In one embodiment, the cell is selected from the group consisting of a CD33-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-CD33 antibody or fragment thereof, wherein the antibody or a fragment thereof comprises an amino acid sequence selected from the group consisting of SEQ ID NOs: 2, 4, 6, 8, 10, and 12. In one embodiment, the antibody or fragment thereof inhibits the interaction between a first cell with a T cell, wherein the first cell is selected from the group consisting of a CD33-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds CD33 and/or one or more of the aforementioned antigens, under conditions sufficient to form an immune complex of the antigen binding domain on the CAR and the extracellular domain of CD33 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular CD33 antigen binding domain comprising the amino acid sequence of SEQ ID NOs. 2, 4, 6, 8, 10, or 12, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one CD33 antigen binding domain comprising the amino acid sequence of SEQ ID NOs. 2, 4, 6, 8, 10, or 12, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one CD33 antigen binding domain comprising the amino acid sequence of SEQ ID NOs. 2, 4, 6, 8, 10, or 12, or any combination thereof, at least one transmembrane domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein, In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIG. 1 depicts a schematic of the general domain structure of CARs with novel extracellular CD33 antigen binding domain sequences. A chimeric antigen receptor is composed of an extracellular CD33-binding immunoglobulin single chain fragment variable (ScFv) domain, or an immunoglobulin heavy chain fragment variable only (VH) domain, a hinge domain derived from CD8 (FIGS. 1A, 1B, 1F, 1G), TNFRSF19 (FIGS. 1C, 1D), of IgG4 (FIG. 1E), a transmembrane domain derived from CD8 (FIGS. 1A, 1B, 1E, 1F, 1G), TNFRSF19 (FIGS. 1C, 1D), an intracellular signaling costimulatory domain derived from CD137/4-1BB (FIGS. 1A, 1C, 1F) or CD28 (FIGS. 1B, 1D, 1E, 1G), and CD3 zeta signaling domain. Some bicistronic constructs incorporate a tag derived from truncated EGFR (tEGFR) via ribosomal skipping 2A sequence (FIGS. 1F, 1G).

FIG. 2 depicts several chimeric antigen receptors (CARs) containing novel extracellular CD33 antigen binding domain sequences. The general scheme for the CARs includes, from the N terminus to the C terminus, a Signal peptide, anti-CD33 binder variable heavy chain fragment or a linked single chain fragment variable (ScFv), extracellular linker, transmembrane, 4-1BB, CD3 zeta. FIG. 2A depicts a lentiviral vector expressing the CAR the LTG 1905 EF1a VH-2 CD33-CD8 TM-41BB-CD3 zeta nucleic acid sequence and the encoded amino acid sequence. FIG. 2B depicts a lentiviral vector expressing the CAR containing the LTG 1906 (EF1a-VH-4 CD33-CD8 TM-41BB-CD3 zeta) nucleic acid sequence and the encoded amino acid sequence. FIG. 2C depicts a lentiviral vector expressing the CAR containing the LTG1936 EF1a ScFv9 CD33 CD8 TM-41BB-CD3 zeta nucleotide sequence and the encoded amino acid sequence. FIG. 2D depicts a lentiviral vector expressing the CAR containing the LTG1937 EF1a ScFv10 CD33 CD8 TM-41BB-CD3 zeta nucleic acid sequence and the encoded amino acid sequence. FIG. 2E depicts a lentiviral vector expressing the CAR containing the LTG1938 EF1a ScFv12 CD33 CD8 TM-41BB-CD3 zeta nucleic acid sequence and the encoded amino acid sequence. FIG. 2F depicts a lentiviral vector expressing the CAR containing the LTG1939 EF1a ScFv15 CD33 CD8 TM-41BB-CD3 zeta nucleic acid sequence and the encoded amino acid sequence.

FIG. 6 depicts Anti CD33 CART surface expression in primary human T cells. CAR T cells redirected to CD33 tumor antigen via the use of ScFv targeting domains were generated by lentiviral transduction. CAR T detection was performed by flow cytometry. T cells were washed twice in cold PBS-EDTA buffer and stained with CD33-Fc peptide followed by anti Fc-AF647 reagent. Data were acquired on MACSQuant 10 flow cytometer in the APC channel. UTD-non-transduced cells, 1398-GFP-negative controls.

FIG. 10 depicts the tumor rejection kinetics by CD33-targeting CAR T cells as assessed in vivo using bioluminescent imaging. NSG mice were inoculated with $1.0 \times 10^6$ MOLM-14 CD33$^+$ AML cells on day 0, and $5.0 \times 10^6$ CAR T$^+$ cells/mouse was administered on study day 5. Tumor burden was assessed weekly between days 14-35 via bioluminescent imaging. A. Average Radiance +/−SEM, N=6 mice/group. B. Kaplan-Meier curves depicting the percentage of mice surviving in each experimental group over the course of experiment, N=6 mice/group. TA-tumor alone, UTD-untransduced T cells control.

FIG. 11 depicts the functionality of CD33-targeting CAR T cells as assessed in vivo. NSG mice were inoculated with $1.0 \times 10^6$ MOLM-14 CD33$^+$ AML cells on day 0, and $5.0 \times 10^6$ CAR T$^+$ cells/mouse was administered on study day 5. Blood was collected from mice on study day 19 and analyzed for circulating CAR T, tumor cells, and the levels of inflammatory cytokines. A. CART cells and MOLM-14 tumor cells were acquired by flow cytometry, with absolute cell numbers determined using CountBright beads. B. The level of inflammatory cytokines in mouse plasma was assessed by MACS Human Multiplex Bead Array. N=6 mice/group. TA-tumor alone, UTD-untransduced T cells control. Groups were compared by two way ANOVA and Dunnett's post-hoc test. ***$p<0.001$, *$p<0.05$, NS— non-significant.

FIG. 12 depicts several chimeric antigen receptors (CARs) containing novel extracellular VH CD33_4 antigen binding domain sequence in the context of different CAR configurations. The general scheme for the CARs includes, from the N terminus to the C terminus, a Signal peptide, anti-CD33 binder variable heavy chain fragment extracellular linker, transmembrane domain, costimulatory domain, and CD3 zeta activation domain. Some sequences contain a tEGFR tag peptide separated by 2A ribosomal skip sequence, downstream from CAR sequence. FIG. 12A depicts a lentiviral vector expressing the CAR containing the LTG1927 EF1a CD33_4 CD8 TM_CD28 CD3 zeta nucleic acid sequence and the encoded amino acid sequence. FIG. 12B depicts a lentiviral vector expressing the CAR containing the LTG_D0033 EF1a CD33_4 VH TNFRSF19H_TM_CD28 zeta nucleic acid sequence and the encoded amino acid sequence. FIG. 12C depicts a lentiviral vector expressing the CAR containing the LTG D0034 Ef1a_CD33_4 VH TNFRSF19H_TM_4-1BB CD3 zeta nucleic acid sequence and the encoded amino acid sequence. FIG. 12D depicts a lentiviral vector expressing the CAR containing LTG_D0015 CD33_4VH CD8 BB CD3 zeta T2A tEGFR nucleic acid sequence and the encoded amino acid sequence. FIG. 12E depicts a lentiviral vector expressing the CAR containing the LTG_D0016 CD33_4VH CD8 28 CD3 zeta T2A tEGFR nucleic acid sequence and the encoded amino acid sequence. FIG. 12F depicts a lentiviral vector expressing the CAR containing the LTG_D0035 Ef1a CD33_4 VH H CH2 CH3 IgG4_CD8TM_CD28 CD3 zeta nucleic acid sequence and the encoded amino acid sequence.

DETAILED DESCRIPTION

Definitions

Figure 3:
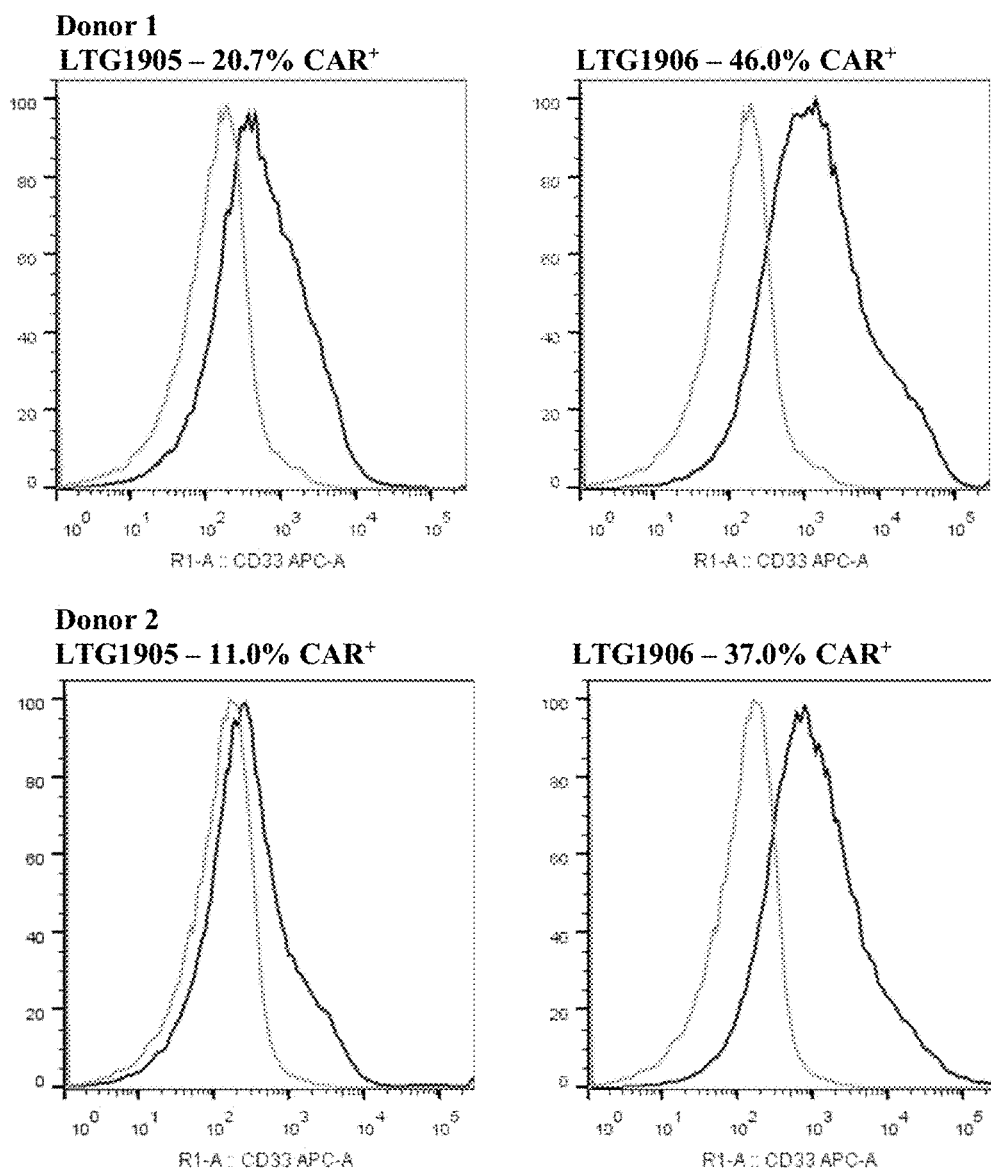
FIG. 3 depicts Anti CD33 CART surface expression in primary human T cells. CAR T cells redirected to CD33 tumor antigen via the use of variable heavy chain only targeting domains were generated by lentiviral transduction. CART detection was performed by flow cytometry. T cells were washed twice in cold PBS-EDTA buffer and stained with CD33-Fc peptide followed by anti Fc-AF647 reagent. Data were acquired on MACSQuant 10 flow cytometer in the APC channel. NT-non-transduced cells, GFP-negative controls.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+-0.20% or in some instances .+-0.10%, or in some instances .+-0.5%, or in some instances .+-0.1%, or in some instances .+-0.01% from the specified value, as such variations are appropriate to perform the disclosed methods.

Unless otherwise noted, the technical terms herein are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for CD33 antibodies or fragments thereof as well as chimeric antigen receptors (CARs) having such CD33 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human antigen binding domain in a CAR, rather than using mouse-derived antigen binding fragments which are prone to induce anti-mouse immune response and CAR T elimination in a host (c.f., the UPenn-sponsored clinical trial using mouse derived SS1 ScFv sequence, NCT02159716), may also determine the functional activity of a CAR-expressing T cell.

The CARs disclosed herein are expressed at a high level in a cell. A cell expressing the CAR has a high in vivo proliferation rate, produces large amounts of cytokines, and has a high cytotoxic activity against a cell having, on its surface, a CD33 antigen to which a CAR binds. The use of a human extracellular CD33 antigen binding domain results in generation of a CAR that functions better in vivo, while avoiding the induction of anti-CAR immunity in the host immune response and the killing of the CAR T cell population. The CARs expressing the entirely human extracellular CD33 ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to CD33. This latter property allows investigators to better tune efficacy vs toxicity, and/or tissue specificity of the CAR T product, since lower-affinity binders may have higher specificity to tumors vs normal tissues due to higher expression of CD33 on tumors than normal tissue, which may prevent on-target off tumor toxicity and bystander cell killing.

What follows is a detailed description of the inventive CARs including a description of their extracellular CD33 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one CD33 antigen binding domain capable of binding to CD33, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARS the ability to recognize antigen independent of antigen processing, thus bypassing a major mechanism of tumor escape. Moreover, when expressed in T-cells, CARS advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and CD33. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

In one preferred embodiment, the tumor antigen is CD33 and the tumors associated with expression of CD33 comprise lung mesothelioma, ovarian, and pancreatic cancers that express high levels of the extracellular protein CD33, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; over-expressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD33, c-Met, PSMA, Glycolipid F77, EGFRvIII, GD-2, MY-ESO-1 TCR, MAGE A3 TCR, and the like.

In a preferred embodiment, the antigen binding domain portion of the CAR targets the extracellular CD33 antigen.

In one preferred embodiment, the isolated nucleic acid molecule encoding the extracellular CD33 VH-2 antigen binding domain comprises a nucleotide sequence of SEQ ID NO: 1, or a sequence with 85%, 90%, 95%, 96%, 97%, 98% or 99% identity thereof. In one embodiment, an isolated nucleic acid molecule is provided wherein the encoded extracellular CD33 VH-2 antigen binding domain comprises an amino acid sequence of SEQ ID NO: 2, or an amino acid sequence with 85%, 90%, 95%, 96%, 97%, 98% or 99% identity to an amino acid sequence of SEQ ID NO: 2.

In one preferred embodiment, the isolated nucleic acid molecule encoding the extracellular CD33 VH-4 antigen binding domain comprises a nucleotide sequence of SEQ ID NO: 3, or a sequence with 85%, 90%, 95%, 96%, 97%, 98% or 99% identity thereof. In one embodiment, an isolated nucleic acid molecule is provided wherein the encoded extracellular CD33 VH-4 antigen binding domain comprises an amino acid sequence of SEQ ID NO: 4, or an amino acid sequence with 85%, 90%, 95%, 96%, 97%, 98% or 99% identity to an amino acid sequence of SEQ ID NO: 4.

In one preferred embodiment, the isolated nucleic acid molecule encoding the extracellular CD33 ScFv 9 antigen binding domain comprises a nucleotide sequence of SEQ ID NO: 5, or a sequence with 85%, 90%, 95%, 96%, 97%, 98% or 99% identity thereof. In one embodiment, an isolated nucleic acid molecule is provided wherein the encoded extracellular CD33 ScFv 9 antigen binding domain comprises an amino acid sequence of SEQ ID NO: 6, or an amino acid sequence with 85%, 90%, 95%, 96%, 97%, 98% or 99% identity to an amino acid sequence of SEQ ID NO: 6.

In one preferred embodiment, the isolated nucleic acid molecule encoding the extracellular CD33 ScFv 10 antigen binding domain comprises a nucleotide sequence of SEQ ID NO: 7, or a sequence with 85%, 90%, 95%, 96%, 97%, 98% or 99% identity thereof. In one embodiment, an isolated nucleic acid molecule is provided wherein the encoded extracellular CD33 ScFv 10 antigen binding domain comprises an amino acid sequence of SEQ ID NO: 8, or an amino acid sequence with 85%, 90%, 95%, 96%, 97%, 98% or 99% identity to an amino acid sequence of SEQ ID NO: 8.

In one preferred embodiment, the isolated nucleic acid molecule encoding the extracellular CD33 ScFv 12 antigen binding domain comprises a nucleotide sequence of SEQ ID NO: 9, or a sequence with 85%, 90%, 95%, 96%, 97%, 98% or 99% identity thereof. In one embodiment, an isolated nucleic acid molecule is provided wherein the encoded extracellular CD33 ScFv 12 antigen binding domain comprises an amino acid sequence of SEQ ID NO: 10, or an amino acid sequence with 85%, 90%, 95%, 96%, 97%, 98% or 99% identity to an amino acid sequence of SEQ ID NO: 10.

In one preferred embodiment, the isolated nucleic acid molecule encoding the extracellular CD33 ScFv 15 antigen binding domain comprises a nucleotide sequence of SEQ ID NO: 11, or a sequence with 85%, 90%, 95%, 96%, 97%, 98% or 99% identity thereof. In one embodiment, an isolated nucleic acid molecule is provided wherein the encoded extracellular CD33 ScFv 15 antigen binding domain comprises an amino acid sequence of SEQ ID NO: 12, or an amino acid sequence with 85%, 90%, 95%, 96%, 97%, 98% or 99% identity to an amino acid sequence of SEQ ID NO: 12.

The generation and binding characteristics of the specific CD33 variable heavy chain only and ScFv antigen binding fragments or antigen binders described herein is shown in Example 1.

In the various embodiments of the CD33-specific CARs disclosed herein, the general scheme is set forth in FIG. 1 and includes, from the N-terminus to the C-terminus, a signal or leader peptide, anti-CD33 ScFv, extracellular linker, CD8 transmembrane, 4-1BB, CD3 zeta, wherein the bolded text represents the cloning sites for linking domains.

In one embodiment, the nucleic acid sequence encoding a CAR comprises the nucleic acid sequence of SEQ ID NO: 15, and encodes the CAR comprising the amino acid sequence as set forth in SEQ ID NO: 16 [LTG 1905 EF1a VH-2 CD33-CD8 TM-41BB-CD3 zeta amino acid sequence (as depicted in FIG. 2A)].

In one embodiment, the nucleic acid sequence encoding a CAR comprises the nucleic acid sequence of SEQ ID NO: 15, or a sequence with 85%, 90%, 95%, 96%, 97%, 98% or 99% identity thereof, and encodes the CAR comprising the amino acid sequence as set forth in SEQ ID NO: 16 or a sequence with 85%, 90%, 95%, 96%, 97%, 98% or 99% identity thereof LTG 1905 EF1a VH-2 CD33-CD8 TM-41BB-CD3 zeta amino acid sequence (as depicted in FIG. 2A)].

In another embodiment, the nucleic acid sequence encoding a CAR comprises the nucleic acid sequence of SEQ ID NO: 17, and encodes the CAR comprising the amino acid sequence as set forth in SEQ ID NO: 18 [LTG 1906 EF1a-VH-4 CD33-CD8 TM-41BB-CD3 zeta amino acid sequence (as depicted in FIG. 2B)].

In another embodiment, the nucleic acid sequence encoding a CAR comprises the nucleic acid sequence of SEQ ID NO: 17 or a sequence with 85%, 90%, 95%, 96%, 97%, 98% or 99% identity thereof, and encodes the CAR comprising the amino acid sequence as set forth in SEQ ID NO: 18 or a sequence with 85%, 90%, 95%, 96%, 97%, 98% or 99% identity thereof [LTG 1906 EF1a-VH-4 CD33-CD8 TM-41BB-CD3 zeta amino acid sequence (as depicted in FIG. 2B)].

In another embodiment, the nucleic acid sequence encoding a CAR comprises the nucleic acid sequence of SEQ ID NO: 19, and encodes the CAR comprising the amino acid sequence as set forth in SEQ ID NO: 20 [LTG1936 EF1a ScFv9 CD33 CD8 TM-41BB-CD3 zeta CAR amino acid sequence (as depicted in FIG. 2C)].

In another embodiment, the nucleic acid sequence encoding a CAR comprises the nucleic acid sequence of SEQ ID NO: 19 or a sequence with 85%, 90%, 95%, 96%, 97%, 98% or 99% identity thereof, and encodes the CAR comprising the amino acid sequence as set forth in SEQ ID NO: 20 or a sequence with 85%, 90%, 95%, 96%, 97%, 98% or 99% identity thereof [LTG1936 EF1a ScFv9 CD33 CD8 TM-41BB-CD3 zeta CAR amino acid sequence (as depicted in FIG. 2C)].

In yet another embodiment, the nucleic acid sequence encoding a CAR comprises the nucleic acid sequence of SEQ ID NO: 21, and encodes the CAR comprising the amino acid sequence as set forth in SEQ ID NO: 22 [LTG1937 EF1a ScFv10 CD33 CD8 TM-41BB-CD3 amino acid sequence (as depicted in FIG. 2D)].

In yet another embodiment, the nucleic acid sequence encoding a CAR comprises the nucleic acid sequence of SEQ ID NO: 21 or a sequence with 85%, 90%, 95%, 96%, 97%, 98% or 99% identity thereof, and encodes the CAR comprising the amino acid sequence as set forth in SEQ ID NO: 22 or a sequence with 85%, 90%, 95%, 96%, 97%, 98% or 99% identity thereof [LTG1937 EF1a ScFv10 CD33 CD8 TM-41BB-CD3 amino acid sequence (as depicted in FIG. 2D)].

In yet another embodiment, the nucleic acid sequence encoding a CAR comprises the nucleic acid sequence of SEQ ID NO: 23, and encodes the CAR comprising the amino acid sequence as set forth in SEQ ID NO: 24 [LTG1938 EF1a ScFv12 CD33 CD8 TM-41BB-CD3 zeta amino acid sequence (as depicted in FIG. 2E)].

In yet another embodiment, the nucleic acid sequence encoding a CAR comprises the nucleic acid sequence of SEQ ID NO: 23 or a sequence with 85%, 90%, 95%, 96%, 97%, 98% or 99% identity thereof, and encodes the CAR comprising the amino acid sequence as set forth in SEQ ID NO: 24 or a sequence with 85%, 90%, 95%, 96%, 97%, 98% or 99% identity thereof [LTG1938 EF1a ScFv12 CD33 CD8 TM-41BB-CD3 zeta amino acid sequence (as depicted in FIG. 2E)].

In yet another embodiment, the nucleic acid sequence encoding a CAR comprises the nucleic acid sequence of SEQ ID NO: 25, and encodes the CAR comprising the amino acid sequence as set forth in SEQ ID NO: 26 [(LTG1939 EF1a ScFv15 CD33 CD8 TM-41BB-CD3 zeta amino acid sequence (as depicted in FIG. 2F)].

In yet another embodiment, the nucleic acid sequence encoding a CAR comprises the nucleic acid sequence of SEQ ID NO: 25 or a sequence with 85%, 90%, 95%, 96%, 97%, 98% or 99% identity thereof, and encodes the CAR comprising the amino acid sequence as set forth in SEQ ID NO: 26 or a sequence with 85%, 90%, 95%, 96%, 97%, 98% or 99% identity thereof [(LTG1939 EF1a ScFv15 CD33 CD8 TM-41BB-CD3 zeta amino acid sequence (as depicted in FIG. 2F)].

The surface expression of anti-CD33 CARs incorporating immunoglobulin heavy chain variable domain (VH) and single chain fragment variable (ScFv) sequences reactive with CD33 antigen, is shown in Example 2 infra and summarized in Table 2. The expression level for each ScFv- or VH-containing CAR was determined by flow cytometric analysis of LV-transduced T cells from healthy donors using a recombinant CD33-Fc peptide, followed by anti-human Fc F(ab')2 fragment conjugated to AF647, and detected in the APC channel, (c.f., Example 2, FIGS. 3 and 6). The VH-based anti-CD33 CAR constructs 1905 and 1906 (black traces) were readily detected on the surface of T cells from two donors, demonstrating the reproducibility of T cell transduction. By contrast, no CAR expression was detected in the negative control non-transduced T cells (gray traces), and GFP control (not shown), thus demonstrating the specificity of the detection method used (c.f., Example 2, FIG. 3 and Table 2). Similarly, the ScFv-based anti-CD33 CAR constructs 1936, 1937, 1938 and 1939 were highly expressed in human primary T cells (black traces) as compared to non-transduced T cell controls (gray traces). Representative results from one donor are shown.

Figure 4:
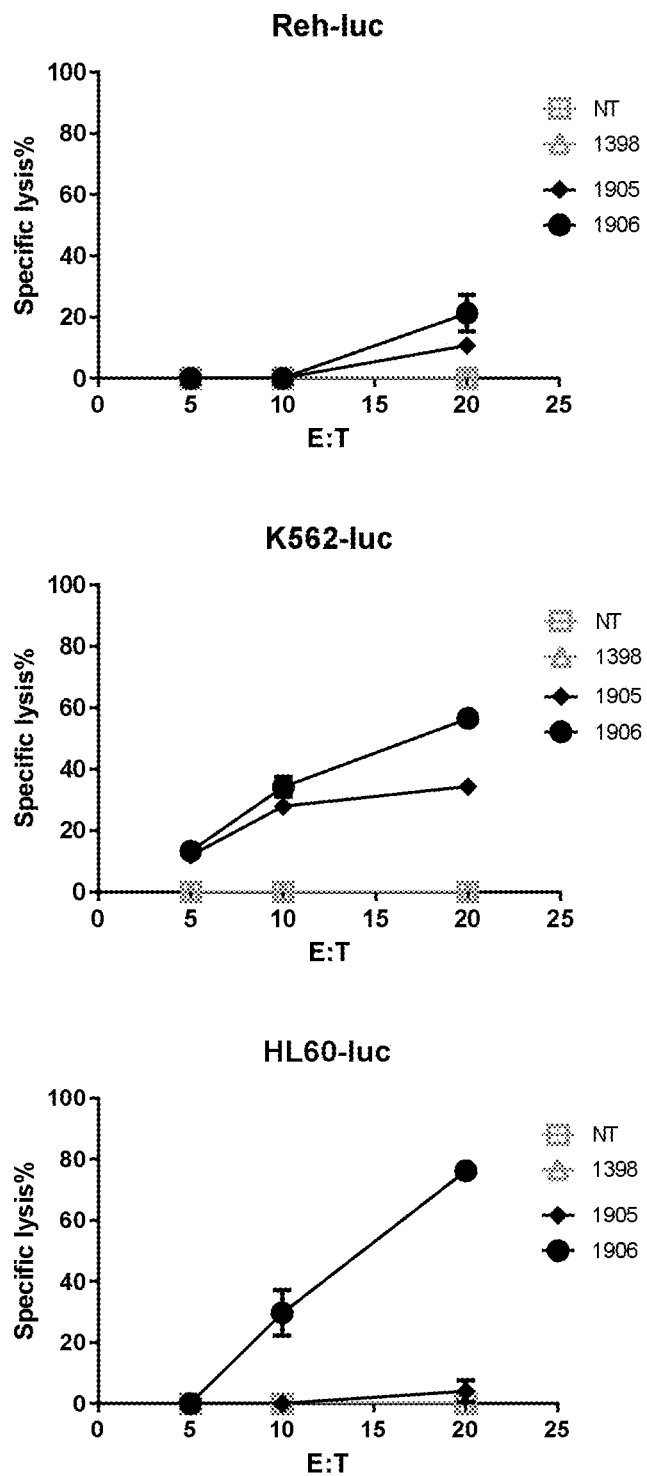
FIG. 4 depicts anti CD33 CAR T cells incorporating immunoglobulin heavy chain variable domain binders demonstrate cytolysis of CD33-positive tumors in vitro. CAR T cells expressing anti-CD33 constructs were incubated with CD33-high (HL-60), CD33-moderate (K562) and CD33-low (Reh) targets stably transduced with firefly luciferase, at effector to target ratio of 5, 10 and 20 overnight. Then, CART cytotoxic activity was assessed by luciferase activity measurement as described in the Materials and Methods. N=3+/−SEM.
Figure 7:
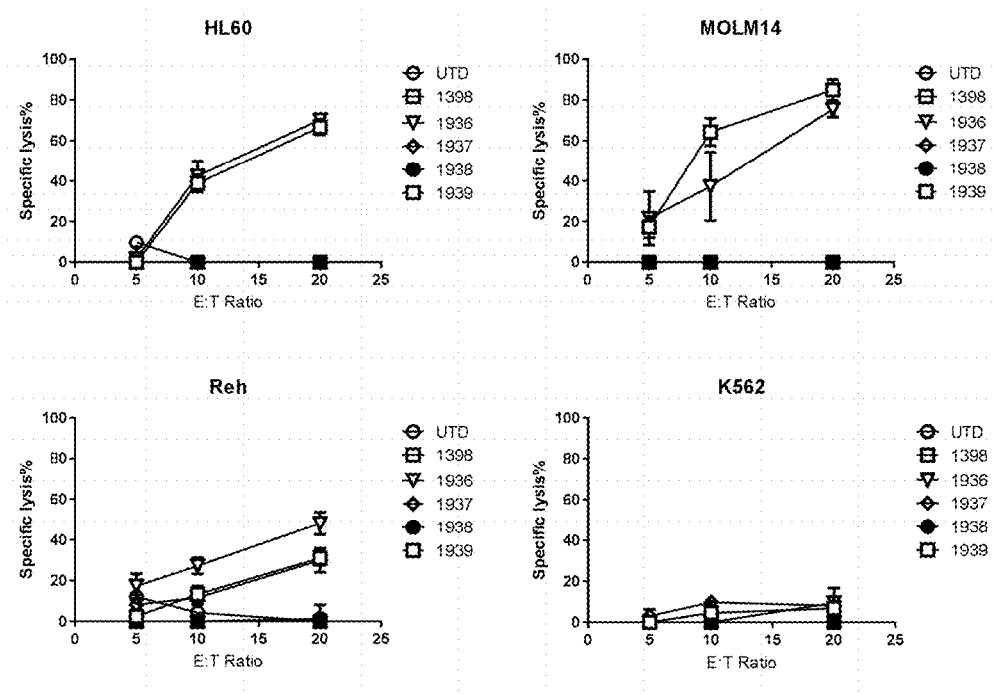
FIG. 7 depicts anti CD33 CAR T cells incorporating immunoglobulin heavy chain variable domain binders demonstrate cytolysis of CD33-positive tumors in vitro. CAR T cells expressing anti-CD33 constructs were incubated with CD33-high (HL-60, MOLM-14), CD33-moderate (K562) and CD33-low (Reh) targets stably transduced with firefly luciferase, at effector to target ratio of 5, 10 and 20 overnight. Then, CART cytotoxic activity was assessed by luciferase activity measurement as described in the Materials and Methods. N=3+/−SEM.
Figure 8:
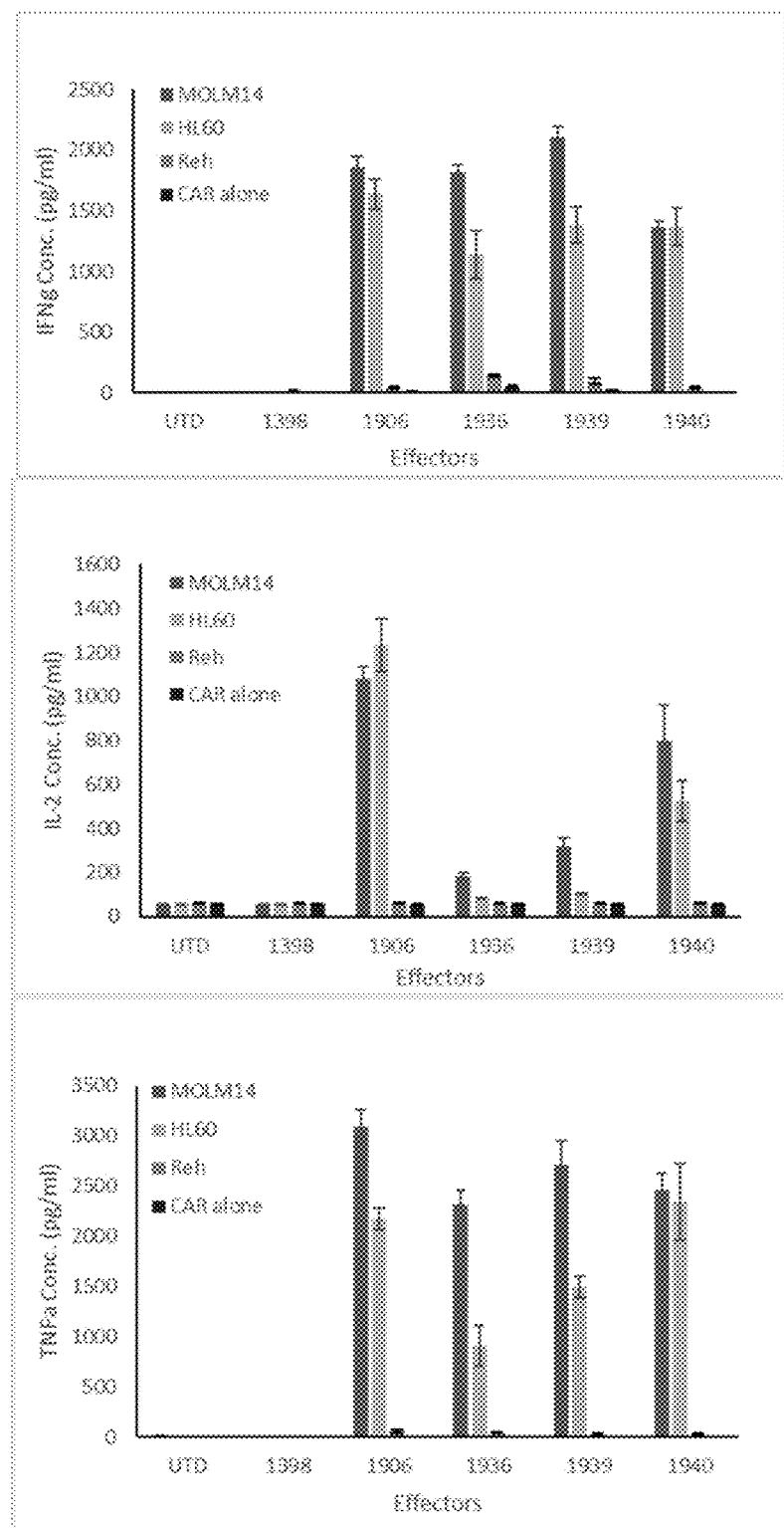
FIG. 8 depicts CD33-specifc scFv-based and VH-based CAR T cells elaborate high levels of cytokines when co-cultured with CD33-positive leukemia lines. Anti-CD33 CART cells were co-incubated with CD33-high (HL-60, MOLM-14) or CD33-low (Reh) leukemia lines overnight at E:T ratio of 1:1, then supernatants were analyzed for cytokine concentrations by ELISA. N=3+/−SD. Negative controls: UTD-non-transduced T cells, 1398—GFP-transduced T cells.

As shown in Example 2 FIG. 4 and FIG. 7, high cytolytic activity of the CD33 CARs was demonstrated when lentiviral vectors (LV) expressing the following CARs were created and tested for anti-leukemia activity. Each experimental CAR contains the 4-1BB/CD3-zeta chain signaling motif and the specific anti-CD33 binding motif/domain noted therein. Four leukemia target lines with varying CD33 surface expression were used: HL-60 and MOLM-14 (high), Reh and K562 (low). The VH-domain-based CAR-T constructs LTG1905 and LTG1906 lysed the CD33-low K562 cells, although LTG1906 showed superior cytolytic function at the effector to target (E:T) ratios listed on the x-axis (c.f., FIG. 4, LTG1905 and LTG1906, black diamond and circle, respectively. When combined with the CD33-high HL-60 tumor line, LTG1906, but not LTG1905, demonstrated potent killing function, underscoring the robustness of construct LTG1906. By contrast, no specific cytolytic activity was exerted by either one of the negative control groups: NT, (untransduced T cells), and 1398 (T cells transduced with GFP control). Therefore, the cytolytic activity of anti CD33 CARs LTG1906 and LTG1905 we observed against CD33-expressing tumor lines is both target-specific and CART-dependent.

By comparison, ScFv-based anti-CD33 CAR constructs LTG1936 and LTG1939 were able to efficiently lyse CD33-high tumor lines HL-60 and MOLM-14, whereas they only partially lysed the CD33-low Reh tumor line, and had no specific lytic activity against K562, (cf., FIG. 7, LTG1398 and LTG1936 white square and white overturned triangle, respectively). This finding demonstrates the efficiency and specificity of the generated CAR constructs. Unexpectedly, the additional CAR constructs tested in this set, LTG1937 and LTG1938, were inefficient in lysing the CD33-high tumor lines, thus again demonstrating that CART design is not trivial and soluble antibody characteristics do not directly translate to CAR functionality.

The capacity of anti-CD33 CAR T cells for cytokine secretion was then evaluated. Tumor cells were co-incubated with CAR T cells or control T cells at effector to target ratio of 10:1 overnight, and culture supernatants were analyzed by ELISA for IFN gamma, TNF alpha and IL-2 (c.f., FIG. 5 and Table 2). Of note, CAR T-expressing cells LTG1905 and LTG1906 elaborated high levels of IFN gamma, TNF alpha and IL-2, whereas the negative control NT and 1398 groups yielded no appreciable cytokine induction. Surprisingly, CD33 CAR LTG1905 tended to yield greater levels of induced cytokines against all tested tumor lines as compared to construct LTG1906. This result is in contrast with lower in vitro cytolytic function of LTG1905 as compared to LTG1906 (c.f., FIG. 4), and suggests that multiple CAR T functional endpoints need to be tested on construct by construct basis.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with an exemplary extracellular CD33 variable heavy chain only and ScFv antigen binding domains, other nucleotide and/or amino acid variants within the CD33 variable heavy chain only and ScFv antigen binding domains may be used to derive the CD33 antigen binding domains for use in the CARs described herein.

Depending on the desired antigen to be targeted, the CAR can be additionally engineered to include the appropriate antigen binding domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR additionally targets CD19. Preferably, the antigen binding domain in the CAR is anti-CD19 ScFv, wherein the nucleic acid sequence of the anti-CD19 ScFv comprises the sequence set forth in SEQ ID NO: 37 In one embodiment, the anti-CD19 ScFv comprises the nucleic acid sequence that encodes the amino acid sequence of SEQ ID NO: 30. In another embodiment, the anti-CD19 ScFv portion of the CAR comprises the amino acid sequence set forth in SEQ ID NO: 38.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus*, *Escherichia coli*, *Pseudomonas*, or *Salmonella*. Particularly, there is provided a CAR capable of binding to an antigen derived from an infectious bacterium, for example, *Helicobacter pyloris*, *Legionella pneumophilia*, a bacterial strain of *Mycobacteria* sps. (e.g. *M. tuberculosis*, *M. avium*, *M. intracellulare*, *M. kansaii*, or *M. gordonea*), *Staphylococcus aureus*, *Neisseria gonorrhoeae*, *Neisseria meningitides*, *Listeria monocytogenes*, *Streptococcus pyogenes*, Group A *Streptococcus*, Group B *Streptococcus* (*Streptococcus agalactiae*), *Streptococcus pneumoniae*, or *Clostridium tetani*, or a combination thereof 2. Transmembrane Domain With respect to the transmembrane domain, the CAR comprises one or more transmembrane domains fused to the extracellular CD33 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 27. In one embodiment, the CD8 transmembrane domain comprises the nucleic acid sequence that encodes the amino acid sequence of SEQ ID NO: 28. In another embodiment, the CD8 transmembrane domain comprises the amino acid sequence of SEQ ID NO: 28.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:28, or a sequence with 95-99% identity to an amino acid sequence of SEQ ID NO:28.

In some instances, the transmembrane domain of the CAR comprises the CD8.alpha.hinge domain. In one embodiment, the CD8 hinge domain comprises the nucleic acid sequence of SEQ ID NO: 29. In one embodiment, the CD8 hinge domain comprises the nucleic acid sequence that encodes the amino acid sequence of SEQ ID NO: 30. In another embodiment, the CD8 hinge domain comprises the amino acid sequence of SEQ ID NO: 30, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

In one embodiment, the transmembrane domain in the CAR of the invention is the TNFRSF19 transmembrane domain. In one embodiment, the TNFRSF19 transmembrane domain comprises the nucleic acid sequence of SEQ ID NO: 51. In one embodiment, the TNFRSF19 transmembrane domain comprises the nucleic acid sequence that encodes the amino acid sequence of SEQ ID NO: 52. In another embodiment, the TNFRSF19 transmembrane domain comprises the amino acid sequence of SEQ ID NO: 52.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:52, or a sequence with 95-99% identity to an amino acid sequence of SEQ ID NO:52.

3. Spacer Domain

In the CAR, a spacer domain, also termed hinge domain, can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 79,645,667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 31) which is a hinge region of CD8.alpha. (NCBI RefSeq: NP.sub.-001759.3), amino acid numbers 135 to 195 of CD8.beta. (GenBank: AAA35664.1), amino acid numbers 315 to 396 of CD4 (NCBI RefSeq: NP.sub.-000607.1), or amino acid numbers 137 to 152 of CD28 (NCBI RefSeq: NP.sub.-006130.1) can be used. Also, as the spacer domain, a part of a constant region of an antibody H chain or L chain (CH1 region or CL region, for example, a peptide having an amino acid sequence shown in SEQ ID NO.: 32) can be used. Further, the spacer domain may be an artificially synthesized sequence.

In addition, an entire or a part of amino acids comprising the constant region of a human IgG4 (UniProt ID: P01861), including CH1, (amino acid numbers 1-98), hinge, SEQ ID NO: 80, and the corresponding nucleotide SEQ ID NO:79, (amino acid numbers 99-110), CH2, amino acid SEQ ID NO: 81 and corresponding nucleotide SEQ ID NO: 80, (amino acid numbers 111-220) and CH3, SEQ ID NO:84 and corresponding nucleotide SEQ ID NO: 83, (amino acid numbers 221-327) or a combination thereof, such as IgG4 Hinge CH2 CH3 domain, SEQ ID NO: 86, and the corresponding nucleotide SEQ ID NO: 85, can be used.

In one embodiment, the spacer domain of the CAR comprises the TNFRSF19 hinge domain which comprises the nucleic acid sequence of SEQ ID NO: 53. In one embodiment, the TNFRSF19 hinge domain comprises the nucleic acid sequence that encodes the amino acid sequence of SEQ ID NO: 54. In another embodiment, the TNFRSF19 hinge domain comprises the amino acid sequence of SEQ ID NO: 54, or a sequence with 95-99% identify thereof.

In one embodiment, the spacer domain of the CAR comprises the TNFRSF19 truncated hinge domain comprises the nucleic acid sequence of SEQ ID NO: 55. In one embodiment, the TNFRSF19 truncated hinge domain comprises the nucleic acid sequence that encodes the amino acid sequence of SEQ ID NO: 56. In another embodiment, the TNFRSF19 truncated hinge domain comprises the amino acid sequence of SEQ ID NO: 56, or a sequence with 95-99% identify thereof.

In one embodiment, the TNFRSF19 hinge and transmembrane domains comprise the nucleic acid sequence of SEQ ID NO: 49. In one embodiment, the TNFRSF19 hinge and transmembrane domains comprise the nucleic acid sequence that encodes the amino acid sequence of SEQ ID NO: 50. In another embodiment, the TNFRSF19 hinge and transmembrane domains comprise the amino acid sequence of SEQ ID NO: 50, or a sequence with 95-99% identify thereof.

In one embodiment, a CD8a hinge domain is fused to a TNFRSF19 transmembrane domain comprising the nucleic acid sequence of SEQ ID NO: 57. In one embodiment, the CD8a hinge domain is fused to a TNFRSF19 transmembrane domain comprises the nucleic acid sequence that encodes the amino acid sequence of SEQ ID NO: 58. In another embodiment, the CD8a hinge domain is fused to a TNFRSF19 transmembrane domain comprises the amino acid sequence of SEQ ID NO: 58, or a sequence with 95-99% identify thereof.

Further, in the CAR, a signal peptide sequence, also termed leader peptide, can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 14).

In one embodiment, the CD8 alpha leader peptide, is comprising the nucleic acid sequence of SEQ ID NO: 43. In one embodiment, CD8 alpha leader peptide comprises the nucleic acid sequence that encodes the amino acid sequence of SEQ ID NO: 44. In another embodiment, the CD8a hinge domain is fused to a TNFRSF19 transmembrane domain comprises the amino acid sequence of SEQ ID NO: 44, or a sequence with 95-99% identify thereof.

In another embodiment, the GMCSF leader peptide, is comprising the nucleic acid sequence of SEQ ID NO: 39. In one embodiment, the GMCSF leader peptide, comprises the nucleic acid sequence that encodes the amino acid sequence of SEQ ID NO: 40. In another embodiment, the CD8a hinge domain is fused to a TNFRSF19 transmembrane domain comprises the amino acid sequence of SEQ ID NO: 40, or a sequence with 95-99% identify thereof.

In another embodiment, the TNFRSF19 leader peptide is comprising the nucleic acid sequence of SEQ ID NO: 41. In one embodiment, TNFRSF19 leader peptide, and CD8 alpha leader peptide comprises the nucleic acid sequence that encodes the amino acid sequence of SEQ ID NO: 42. In another embodiment, the CD8a hinge domain is fused to a TNFRSF19 transmembrane domain comprises the amino acid sequence of SEQ ID NO: 42, or a sequence with 95-99% identify thereof.

In one embodiment, a tag sequence encoding a truncated sequence of epidermal growth factor receptor (tEGFR) is comprising the nucleic acid sequence of SEQ ID NO: 67. In one embodiment, tEGFR comprises the nucleic acid sequence that encodes the amino acid sequence of SEQ ID NO: 68. In another embodiment, the tEGFR tag comprises the amino acid sequence of SEQ ID NO: 68, or a sequence with 95-99% identify thereof.

In one embodiment, a furin recognition site and downstream T2A self-cleaving peptide sequence, designed for simultaneous bicistronic expression of the tag sequence and the CAR sequence, is comprising the nucleic acid sequence of SEQ ID NO: 65. In one embodiment, furin and T2A sequence comprises the nucleic acid sequence that encodes the amino acid sequence of SEQ ID NO: 66. In another embodiment, the tEGFR tag comprises the amino acid sequence of SEQ ID NO: 66 or a sequence with 95-99% identify thereof.

In one embodiment, an upstream furin recognition site and T2A self-cleaving peptide sequence and a furin recognition downstream site, designed for simultaneous bicistronic expression of the tag sequence and the CAR sequence, is comprising the nucleic acid sequence of SEQ ID NO: 67. In one embodiment, furin and T2A sequence comprises the nucleic acid sequence that encodes the amino acid sequence of SEQ ID NO: 68. In another embodiment, the tEGFR tag comprises the amino acid sequence of SEQ ID NO: 68 or a sequence with 95-99% identify thereof.

In one embodiment, the targeting domain of the CAR is expressed separately in the form of monoclonal antibody, ScFv Fab, Fab'2 and is containing at binding tag or epitope, whereas the effector-cell expressed component of the CAR contains a binding domain specifically directed to bind the tag or epitope expressed on the soluble CAR module, such as specific binding on the soluble component of the CAR to the cell bound component forms the full functional CAR structure.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.-932170.1), amino acid numbers 45 to 86 of Fc.epsilon.RI.gamma. (NCBI RefSeq: NP.sub.-004097.1), amino acid numbers 201 to 244 of Fc.epsilon.RI.beta. (NCBI RefSeq: NP.sub.-000130.1), amino acid numbers 139 to 182 of CD3.gamma. (NCBI RefSeq: NP.sub.-000064.1), amino acid numbers 128 to 171 of CD3.delta. (NCBI RefSeq: NP.sub.-000723.1), amino acid numbers 153 to 207 of CD3.epsilon. (NCBI RefSeq: NP.sub.-000724.1), amino acid numbers 402 to 495 of CD5 (NCBI RefSeq: NP.sub.-055022.2), amino acid numbers 707 to 847 of 0022 (NCBI RefSeq: NP.sub.-001762.2), amino acid numbers 166 to 226 of CD79a (NCBI RefSeq: NP.sub.-001774.1), amino acid numbers 182 to 229 of CD79b (NCBI RefSeq: NP.sub.-000617.1), and amino acid numbers 177 to 252 of CD66d (NCBI RefSeq: NP.sub.-001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.-001758.2), amino acid numbers 421 to 458 of CD4 (NCBI RefSeq: NP.sub.-000607.1), amino acid numbers 402 to 495 of CD5 (NCBI RefSeq: NP.sub.-055022.2), amino acid numbers 207 to 235 of CD8.alpha. (NCBI RefSeq: NP.sub.-001759.3), amino acid numbers 196 to 210 of CD83 (GenBank: AAA35664.1), amino acid numbers 181 to 220 of CD28 (NCBI RefSeq: NP.sub.-006130.1), amino acid numbers 214 to 255 of CD137 (4-1BB, NCBI RefSeq: NP.sub.-001552.2), amino acid numbers 241 to 277 of CD134 (OX40, NCBI RefSeq: NP.sub.-003318.1), and amino acid numbers 166 to 199 of ICOS (NCBI RefSeq: NP.sub.-036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 33, SEQ ID NO: 45, or SEQ ID NO: 59, respectively and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 34, SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 34, SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

In one embodiment, the intracellular domain in the CAR is designed to comprise the signaling domain of CD28 and the signaling domain of CD3-zeta, wherein the signaling domain of CD28 comprises the nucleic acid sequence set forth in SEQ ID NO: 45, or SEQ ID NO: 59, respectively, and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of CD28 and the signaling domain of CD3-zeta, wherein the signaling domain of CD28 comprises the nucleic acid sequence that encodes the amino acid sequence of SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of CD28 and the signaling domain of CD3-zeta, wherein the signaling domain of CD28 comprises the amino acid sequence set forth in SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithne, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holtiger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 79,645,667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated RCA60 and RCA120 according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethyl aminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-marmosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions.

By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λ[|$]$¨$$[|$]$¨AÄ[|$]$¨güTIO, λʊTI 1, λZapII (Stra-tagene), EMBL4, and λNMI 149, also can be used. Examples of plant expression vectors include pBIO1, pBI101.2, pBHOl 0.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2µ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a $E.$ $coli$ cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., Th1 and Th2 cells, $CD8^+$ T cells (e.g., cytotoxic T cells), tumor infiltrating cells, memory T cells, memory stem cells, i.e. Tscm, naive T cells, and the like. The T cell may be a $CD8^+$ T cell or a $CD4^+$ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a non-toxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masopro col, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenus) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science,* 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Isolation of CD33-Specific Antibodies from a Fully Human Phage-Displayed ScFv and VH Library
Materials and Methods:
a) Production of Human Phage-Displayed ScFv and VH CD33-Specific Antibodies
A naïve human ScFv (recombinant single chain fragment variable of immunoglobulin) phage display library (approximate diversity, $10^{10}$ unique specificities), constructed from peripheral blood B cells of 50 healthy donors (Z. Y. Zhu and D. S. Dimitrov, unpublished data) and a human VH (immunoglobulin heavy chain variable domain) library, were used for selection of ScFvs or VH specific for recombinant human CD33. Amplified libraries of $10^{12}$ phage-displayed ScFv or VH were incubated with 5, 3, and 1, μg of coated CD33 in a 5×100-μl volume, distributed equally in 5 wells of a 96-well plate for 2 h at room temperature during the first, second and third rounds of biopanning, respectively. After each round of incubation the wells were washed 5 times for the first round and 10 times for the later rounds with phosphate-buffered saline containing 0.05% Tween 20 (PBST) to remove nonspecifically bound phage, the bound phage were mixed with TG1 competent cells for 1 hour at 37° C., and the phage was amplified from the infected cells and used in the next round of biopanning. After the third round of biopanning, 380 clones were randomly picked from the infected TG1 cells and each inoculated into 150 μl 2YT medium containing 100 μg/ml carbenicillin and 0.2% glucose in 96-well plates by using the automated BioRobotics BioPick colony picking system (Genomic Solutions, Ann Arbor, Mich.). After the bacterial cultures reached an optical density at 600 nm (OD600) of 0.5, helper phage M13K07 at a multiplicity of infection (MOI) of 10 and kanamycin at 50 μg/ml (final concentration) were added to the medium, and the plates were further incubated at 30° C. overnight in a shaker at 250 rpm. The phage supernatants were mixed with 3% nonfat milk in PBS at a 4:1 volume ratio and used for enzyme-linked immunosorbent assay (ELISA) to identify clones of phage displaying ScFvs or VHs with high CD33 binding affinity. The supernatants were incubated for 2 h at room temperature with recombinant human CD33 coated at 50 ng per well in 96-well plates and washed five times with PBST, (after overnight incubation at 4° C. it was blocked with 3% nonfat milk in PBS and washed three times with PBS containing 0.05% Tween 20.) CD33-bound phage were detected using horseradish peroxidase-conjugated goat anti-M13 antibody. After incubation with the antibody, the non-specifically bound antibody was removed by washing wells, and the 3,3,'5,5'-tetramethylbenzidine (TMB) substrate was added, and solution absorbance at 450 nm (A450) measured. Clones that bound to CD33 with A450 of >1.0 were selected for further characterization.

b) Expression and purification of selected soluble ScFvs or VHs.

The VH and VL of the selected clones and VH of the domain binders were DNA sequenced, and the ScFvs or VHs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 μg/ml ampicillin and 0.2% glucose, and incubated at 37° C. with shaking at 250 rpm. When the culture OD at 600 nm reached 0.90, isopropyl-β-d-thiogalactopyranoside at a 0.5 mM final concentration was added, and the culture was further incubated overnight at 30° C. The bacterial pellet was collected after centrifugation at 8,000×g for 20 min and resuspended in PBS buffer containing 0.5 mU polymixin B (Sigma-Aldrich, St. Louis, Mo.). After 30 min incubation with rotation at 50 rpm at room temperature, the resuspended pellet was centrifuged at 25,000×g for 25 min at 4° C., and the supernatant was used for ScFv purification using the Ni-NTA resin following vendor protocol (Qiagen).

c) ELISA Binding Assay

50 μl of the diluted recombinant human CD33 in PBS at 2 ug/ml was coated in a 96-well plate at 4° C. overnight. Purified ScFv or VHs (from above) with His and Flag tags were serially diluted and added into the target protein coated wells. After washing, a 1:3000 diluted HRP conjugated anti-Flag antibody was added for 1 hr at RT. After washing, 3,3,5,5'-Tetramethylbenzidine (TMB) substrate was added, 1N H$_2$SO$_4$ was added to stop the reaction after incubation at room temperature for 10 minutes, and the O.D. was read at 450 nm to quantify the relative ability of ScFv to bind CD33.

Results:

Based upon the results of the ELISA binding assay, four separate ScFs clones specific for recombinant human CD33 were identified and labeled as human anti-CD33 ScFv binders m1033-9 (ScFv9), m1033-10 (ScFv10), m1033-12 (ScFv12) and m1033-15 (ScFv15), respectively. Two unique VH domain binders m1033-2 (VH-2) and m1033-4 (VH-4) were also identified from the ELISA binding assay. The generation of chimeric antigen receptors expressing the VH-2, VH-4, ScFv9, ScFv10, ScFv12 and ScFv15 human anti-CD33 binders is outlined in Example 2, infra.

Example 2

CARs Expressing Anti-CD33 Fully Human Heavy Chain Ig Only-Based, or scFv-Based Binding Sequences In this example, anti-CD33 CAR T cells derived from novel fully human immunoglobulin heavy chain only, of single chain fragment variable (scFv) binder sequences are described. The novel anti-CD33 CART constructs have demonstrated high level expression in primary human T cells and specific and potent cytotoxic and cytokine functions against CD33-positive tumor cells.

Homo sapiens CD33 (sialic acid binding Ig-like lectin 3, SIGLEC3, SIGLEC-3, gp67, p67) is a well-investigated target on Acute Myeloid leukemia (AML). CD33 humanized antibody (lintuzumab) and a CD33 antibody-drug conjugate (gemtuzumab ozogamincin, or GO, Pfizer) showed some efficacy but failed to demonstrate robust therapeutic benefit in clinical trials (1.

Feldman E J et al. J Clin Oncol 2005; 23(18):4110-4116, 2. Petersdorf S H, et al. Blood 2013; 121(24):4854-4860). AMG330, a CD33-CD3 bispecific T cell engager (BiTE) is also being investigated (Krupka C et al. Blood 2014 123: 356-365). As of this year, GO has been re-introduced to the clinic at an altered, much lower dose, and in a revised regiment, however sufficient clinical data for re-evaluation of this agent yet needs to be accrued. Another agent presently in development, a CD33-tagreting antibody-drug conjugate vadastuximab talirine (SGN-CD33A), recently lead to a clinical hold on several Phase I/II trials due to hepatic toxicity (available on the world wide web at investor.seattle-genetics.com/phoenix.zhtml?c=124860&p=irol-newsArticle&ID=2232880), underscoring the imminent need for identifying safe and efficacious CD33-targeting modalities.

CD33 CARs were designed using CD33 binding sequences derived from either immunoglobulin VH domain, or full length ScFv under the control of EF1a promoter and tested in vitro for transduction efficiency, killing function and cytokine production.

Materials and Methods:

(a) Cell Lines

Human cell lines promyelocytic leukemia HL-60, acute lymphocytic leukemia Reh, monocytic leukemia THP-1, and myelogenous leukemia K562 cell lines were purchased from American Tissue Culture Collection (ATCC, Manassas, Va.). The acute myeloid leukemia MOLM-14 line was purchased from the German Collection of Microorganisms and Cell Lines (DSMZ, Braunschweig Germany). The cell lines were cultured in RPMI-1640 Medium (ATCC) supplemented with 10% heat-inactivated fetal bovine serum. THP-1 culture medium also contained 0.05% beta mercaptoethanol. Luciferase-expressing subclones were generated by stably transducing wild-type leukemia lines with lentiviral vector encoding firefly luciferase with or without GFP (Lentigen Technology, Inc., Gaithersburg, Md.), followed by limiting dilution and selection of luciferase-positive clones.

(b) Creation of Chimeric Antigen Receptor (CAR)—Expression Vectors

CAR antigen-binding domain sequences were derived from human anti-CD33 ScFv or heavy chain variable fragments. CAR T constructs were generated by linking the binder sequence in frame to CD8a linking and transmembrane domains (UniProt sequence ID P01732, aa 138-206), and then to 4-1BB (CD137, aa 214-255, UniProt sequence ID Q07011) signaling domain and CD3 zeta signaling domain (CD247, aa 52-163, Ref sequence ID: NP_000725.1). For some constructs, CD28 costimulatory sequence, rather than 4-1BB costimulatory sequence was used. In some constructs the CD8 linking and/or transmembrane domain were replaced with domains derived from TNFRSF19 protein. For some sequences, truncated epidermal growth factor receptor (tEGFR) tag was incorporated in CAR construct via 2A peptide, to enable tagging of transduced cells in vitro and as a suicide switch for in vivo applications. CAR constructs sequences were cloned into a third generation lentiviral plasmid backbone (Lentigen Technology Inc., Gaithersburg, Md.). Lentiviral vector (LV) containing supernatants were generated by transient transfection of HEK 293T cells and vector pelleted by centrifugation of lentiviral vector-containing supernatants, and stored at −80° C.

(c) Primary T Cell Purification and Transduction

Human primary T cells from normal donors were purified from buffy coats following immunomagnetic bead selection of CD4$^+$ and CD8$^+$ cells according to manufacturer's protocol (Miltenyi Biotec, Bergisch Gladbach, Germany), cultivated in TexMACS medium supplemented with 40 IU/ml IL-2 at a density of 0.3 to 2×10$^6$ cells/ml, activated with CD3/CD28 MACS® GMP TransAct reagent (Miltenyi Biotec) and transduced on day 2 with lentiviral vectors encoding CAR constructs in the presence of 10 ug/ml protamine sulfate (Sigma-Aldrich, St. Louis, Mo.) overnight, and media exchanged on day 4. On day 3, cultures were transferred to TexMACS medium supplemented with 200 IU/ml IL-2, and propagated until harvest on day 7-10.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). Supernatants from co-cultures at E:T ratio of 10:1 were removed and analyzed by ELISA (eBioscience, San Diego, Calif.) for IFNγ, TNFα and IL-2 concentration.

(e) Flow Cytometric Analysis of CAR Surface Expression

For cell staining, half a million CAR T transduced cells were harvested from culture, washed two times in cold AutoMACS buffer supplemented with 0.5% bovine serum albumin (Miltenyi Biotec), and CAR surface expression detected by staining with CD33-Fc peptide (R&D, Minneapolis, Minn.) followed by anti Fc-AF647 conjugate (Jackson ImmunoResearch, West Grove, Pa.). Non-transduced cells were used as negative controls. Dead cells in all studies were excluded by 7AAD staining (BD Biosciences, San Jose, Calif.). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using FlowJo software (Ashland, Oreg.).

(f) In Vivo Analysis of CAR T Function The functionality of CD33-targeting CAR T cells was assessed in vivo. Six to eight weeks old NSG mice, 6 per group, were inoculated with $1.0 \times 10^6$ MOLM-14 CD33$^+$ AML cells on day 0. Tumor burden was determined by IVIS bioluminescent imaging on day 4, mice were randomized to groups with equal mean tumor burden, and $5.0 \times 10^6$ CAR T$^+$ cells/mouse were administered on study day 5. Tumor regression was determined by bioluminescent imaging on days 14, 21, 28 and 35. Mice survival was recorded and analyzed at the end of the study. To determine the presence of CAR T and tumor cells, blood was collected from all animals on study day 19. The absolute numbers of blood CAR T cell and MOLM-14 tumor cells were determined by flow cytometry, and the levels of inflammatory cytokines were measured in plasma by MACSPlex cytokine 12 human kit (Miltenyi Biotec) as per manufacturer's protocol.

(g) Flow Cytometric Analysis of CAR T and Tumor Cells in Mouse Blood.

For flow cytometry 50 ul blood was collected and analyzed for CAR T and MOLM-14 tumor cell number. First, red blood cells were lysed by Red Blood Cells Lysis Solution (Miltenyi Biotec) as per manufacturer's instructions, and white blood cells were stained with human CD45$^+$, CD3$^+$ (Miltenyi Biotec), and 7-AAD (BD Biosciences, San Jose, Calif.) and acquired on MACSQiant 10 flow cytometer (Miltenyi Biotec). MOLM-14-cells, stably expressing the GFP reporter gene, were detected in the B1 channel. Seven-AAD-positive dead cells were excluded from analysis. To facilitate direct quantitation of human T cell and MOLM-14 numbers in blood, CountBright Absolute Counting Beads (ThermoFischer Scientific, Waltham, Mass.) were added to each sample prior to acquisition and the corresponding absolute cell numbers were calculated as per manufacturer's protocol.

(h) Long-Term CAR T and Tumor Co-Incubation Assay

CART cell lines expressing various anti-CD33 CAR constructs and controls were combined with tumor target HL-60 cells at effector to target ratios ranging from 5:1 to 0.04:1 for 5 or 11 days. Negative controls UTD (untransduced cells), T cells alone (E:T 1:0) and GFP-expressing T cells (1398) were included. At each time point, cells were stained with anti-human CD33 and CD3 antibodies and 7-AAD, and acquired on MACSQuant 10 flow cytometer. To determine the percentages of surviving CAR T cells and tumor cells for each condition, cells were gated on Forward and Side scatter, singlets, 7-AAD$^-$, CD3$^+$ or CD33$^+$.

Results:

In order to evaluate the novel anti-CD33 fully human ScFv binding sequences, CAR constructs were designed incorporating each one of the heavy chain only binder sequences VH-2 or VH-4, or ScFv sequences ScFv9, ScFv10, ScFv12, or ScFv15 as a tumor antigen binding domain. In each CAR design, the tumor targeting domain was followed by a linker and transmembrane domains derived from the human CD8 protein, a 4-1BB costimulatory domain and a CD3 zeta signaling domain (Table 1 infra). Construct LTG1940, incorporating the ScFv binding domain derived from sequence My96, was used as a reference control or comparator.

TABLE 1

List of CD33-Targeting CAR Constructs

LTG1905: EF1a VH-2 CD33 -CD8 TM-41BB-CD3 zeta
LTG1906: EF1a VH-4 CD33 -CD8TM-4-1BB-CD3 zeta
LTG1936: EF1a-ScFv9-CD8TM-4-1BB-CD3 zeta
LTG1937: EF1a-ScFv10-CD8TM-4-1BB-CD3 zeta
LTG1938: EF1a-ScFv12-CD33 CAR-CD8TM-4-1BB-CD3 zeta
LTG1939: EF1a-ScFv15-CD33 CAR-CD8TM-4-1BB-CD3 zeta
LTG1940: EF1a-My96_ScFv-CD33 CAR-CD8TM-4-1BB-CD3 zeta T Cells Transduced with Anti-CD33 Chimeric Antigen Receptors Demonstrate Surface Expression and Cytolytic Activity.

a) Surface Expression of Anti-CD33 CARs

To evaluate the novel anti-CD33 CARs, lentiviral vectors (LV) encoding CAR constructs under the control of human EF1a promoter were generated as described in Materials and Methods. Then, human primary T cells derived from two separate healthy donors were transduced with the four lentiviral vectors encoding CARs. Non-transduced cells from same donor (NT) or GFP-transduced cells from same donor served as negative controls.

T cells were activated on culture Day 0 with TransAct T cell reagent (active engagement of CD3 and CD28 antigens, Miltenyi Biotec, Inc.) in the presence of IL-2 as described in Materials and Methods. On culture Day 10, expression of anti-CD33 CARS on T cell surface was detected by CD33-Fc peptide followed by anti Fc-AF647 and analyzed by flow cytometry. Anti-CD33 CAR constructs demonstrated surface CAR expression.

b) Cytolytic Assay of Anti-CD33 CARs

To demonstrate the cytolytic function of the generated CAR T cells, a luciferase-based killing assay was performed using HL-60-luc, MOLM-14 (CD33-high), Reh-luc and K562-luc (CD33-low) leukemia lines stably expressing firefly luciferase. CART cells and target cells were combined at effector to target (E:T) ratios of 20, 10 and 5, and co-incubated overnight, then cell killing was assessed by luminescence as described in Materials and Methods (FIG. 3 FIG. 4; FIG. 6 and FIG. 7). When VH-based anti-CD33 CARs were tested, CART construct LTG1906 showed strong, E:T ratio-dependent cytotoxicity against CD33-high HL-60-luc line, modest cytolysis of CD33-lower expressing K562 line, and only weak cytolytic activity in CD33-low Reh-luc line. Therefore, the cytolytic activity was directly related to the levels of CD33 expression by leukemia. Furthermore, negative control GFP construct LTG1398, and NT (non-transduced T cells from same donor), were not cytolytic, demonstrating that the cytotoxicity was CART-dependent. Notably, the LTG1905 CAR construct was not cytolytic in HL-60 luc line, and only weakly cytolytic in K562-luc line.

Figure 5:
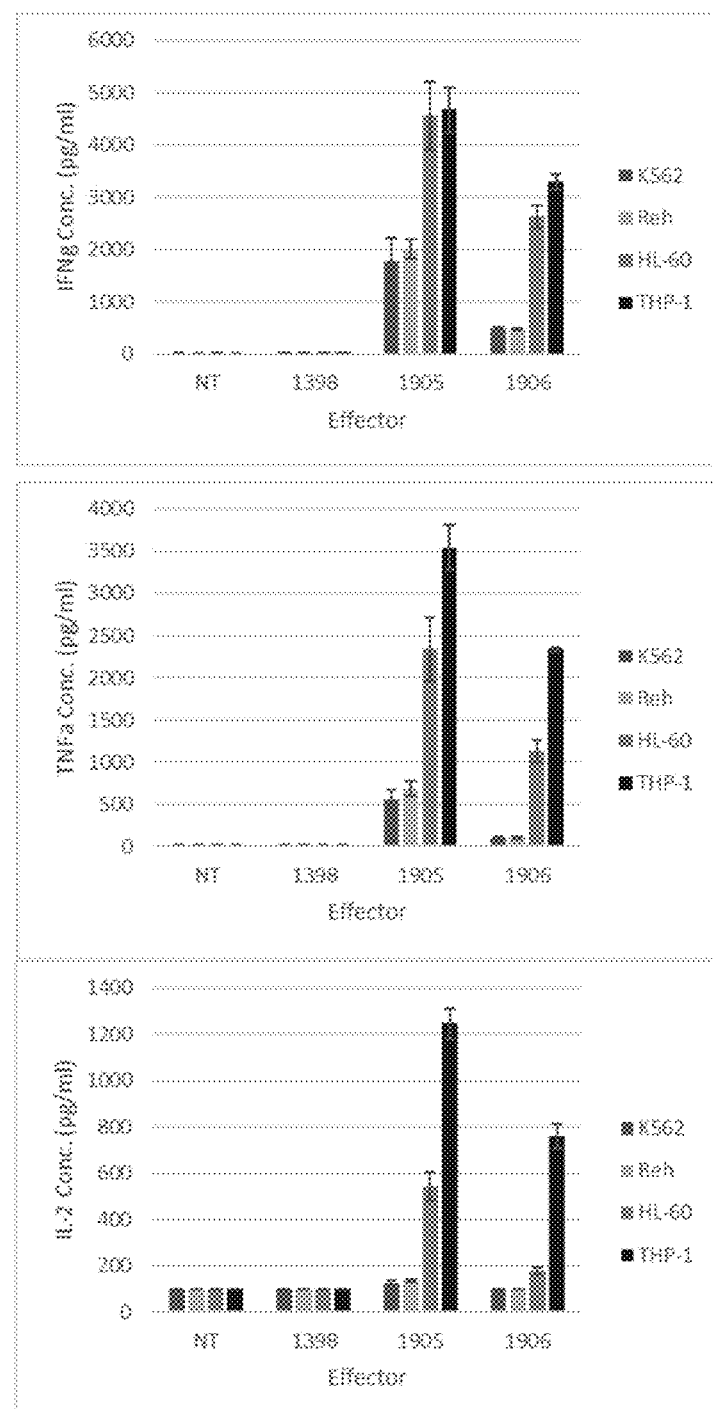
FIG. 5 depicts VH-based CD33-specifc CART cells elaborate high levels of cytokines when co-cultured with CD33-positive leukemia lines. Anti-CD33 CART cells were co-incubated with CD33-high (THP-1, HL-60) CD33-moderate (K562) or CD33-low (Reh) leukemia lines overnight at E:T ratio of 10:1, then supernatants were analyzed for cytokine concentrations by ELISA. N=3+/−SD. Negative controls: NT-non-transduced T cells, 1398—GFP-transduced T cells.

Similarly, construct LTG1906 elaborated high levels of IFNγ, TNFα, and IL-2 in response to CD33-highly positive tumor lines THP-1 and HL-60, whereas CAR T-secreted cytokines remained at low levels when challenged with leukemia lines K562 or Reh, which express low levels of CD33 antigen (FIG. 5). Interestingly, construct LTG1905, despite inefficient in vitro killing of CD33-positive HL-60 leukemia, elaborated very high levels of IFNγ, TNFα, and IL-2 as detected by ELISA. Therefore, CAR design and binder choice are not trivial, as some binders active in a soluble IgG or ScFv format and amenable to expression on T cell surface in a CAR T format, are nevertheless inefficient in killing CD33-positive tumors.

By comparison, when ScFv anti-CD33 CAR T cells were tested, constructs LTG1936 and LTG1939 demonstrated robust killing activity against the CD33-high tumor lines HL-60 and MOLM-14, whereas the activity was much lower against the CD33-low Reh tumor line, and virtually undetectable against the CD33-low K562 cells (FIG. 7). Surprisingly and unexpectedly, CAR constructs LTG 1937 and LTG1938 were inefficient in lysing CD33-positive tumor targets. This again demonstrates that the design of CAR T construct based on antibody fragments is not trivial because soluble antibody binding properties and/or solubility and/or multimerization properties, etc. may not directly translate to CAR functionality. Similarly to VH-only construct 1906, the scFv-based constructs 1936, 1939 and the My96 scFv-based comparator construct 1940 all elaborated high levels of IFN gamma and TNF alpha when challenged with highly CD33$^+$ tumor lines HL-60 and MOLM14, but showed virtually no cytokine induction in the presence of CD33$^{low}$ line Reh, or when CART cells were incubated alone, in the absence of target lines. CAR constructs 1937, 1938, which had shown poor in vitro killing function, were also inefficient in cytokine elaboration in response to tumor cells (data not shown). As comparing cytokine induction by MOLM14 and HL60, MOLM14 exhibits greater CD33 antigen density (30,000 sites per cell in MOLM14 vs 25,000 sites per cell in HL-60, data not shown), which corresponds to greater induction of IFN gamma and TNF alpha elicited by MOLM14 for all anti-CD33 constructs tested. Again, this demonstrates the antigen-specific nature of anti CD33 CAR activation. Unexpectedly, the induction of IL-2 was strong for CAR constructs 1906 and 1940, but moderate for CAR constructs 1936 and 1939.

Figure 9:
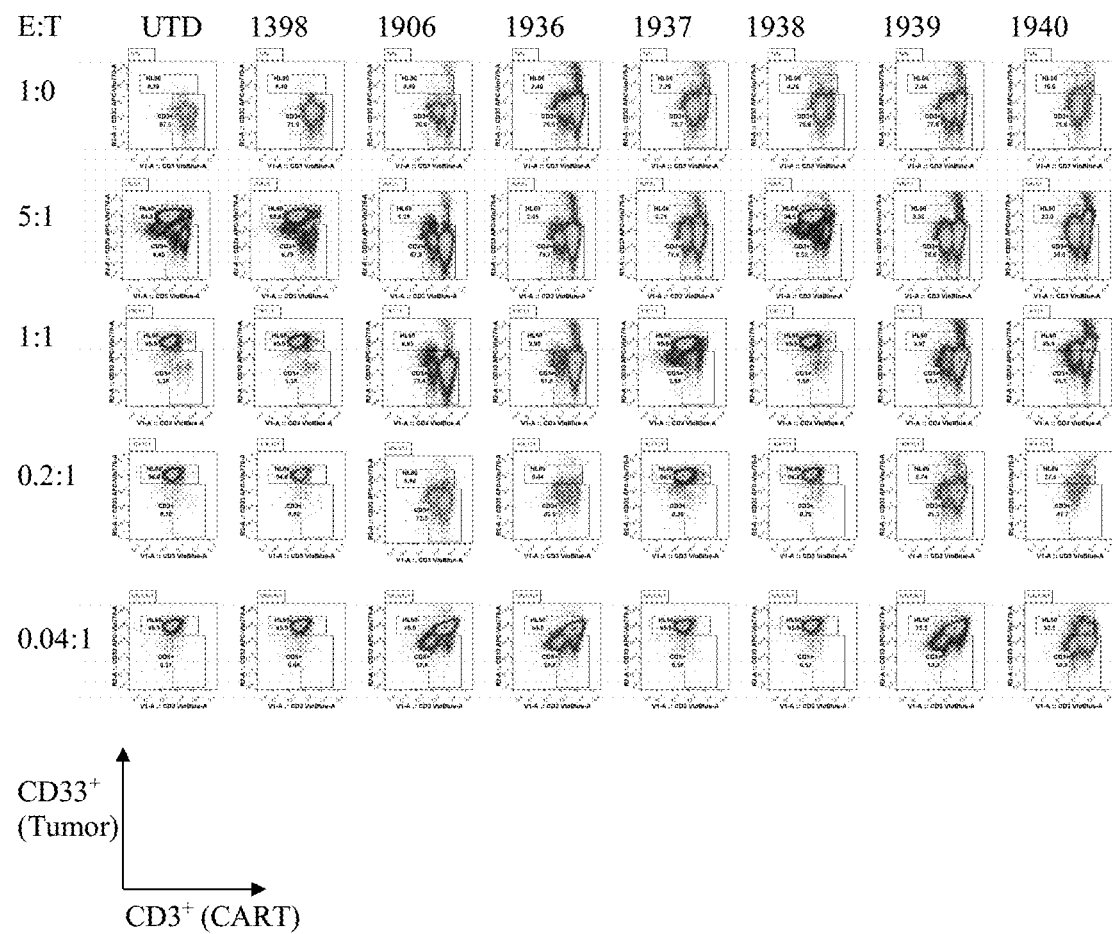
FIG. 9 depicts long-term co-incubation assay of CAR T cells expressing various anti CD33 constructs with HL-60 CD33$^+$ tumor cells. The anti-CD33 CAR T cell lines were combined with HL-60 CD33$^+$ tumor cells in culture at effector to target (E:T) ratios indicated and maintained for 11 days. Then, co-cultured cells were harvested and acquired by flow cytometry. Cells were gated based on single and side scatter, singlets, and dead cells were excluded via 7-AAD staining, as described in Materials and Methods. Boxes indicate the percentages of the surviving HL-60$^+$ tumor cells and the CD3$^+$ CAR T cells for each condition, as per labels. UTD-untransduced T cell control, 1398-GFP transduced T cells control, E:T 1:0 denotes T cells alone control.

A long-term co-incubation assay was then performed, by combining the CARs T cells incorporating different constructs in culture with the HL-60 CD33$^+$ tumor cells at E:T ratios ranging from 5:1 to 0.04:1. UTD, untransduced T cells, 1398, GFP-transduced T cells and E:t 0.1, T cells alone, were used as assay controls. Cells were co-cultured for either 5 days (data not shown) or 11 days, both days demonstrating similar trends in HL-60 elimination for each CAR construct (FIG. 9). In the negative control groups, UTD and 1398, tumor cells have outgrown and T cells disappeared, demonstrating that CAR-mediated stimulation of the T cells is required for cytolytic activity and for prolonged CAR T survival. CAR constructs 1398, 1398, which performed poorly in overnight in vitro assays, were not efficacious at HL-60 killing in this long term assay, and performed similarly to the negative control groups, with disappearance of CAR T cells from cultures and tumor persistence in all E:T ratios equal to or below 1:1. By contrast, the anti-CD33 CAR construct 1906, 1936 and 1939 were equally potent in CTL function to the comparator construct 1940, and successfully eliminated HL-60 tumor cells at E:T ratios as low as 0.2:1 (FIG. 9). Therefore, constructs 1906, 1936, 1939 and 1940 were selected for further evaluation in an in vivo model of AML.

To facilitate the comparison of anti CD33-CAR construct in vivo, a xenograft mouse model was utilized, as described in Materials and Methods. Briefly, NSG mice were inoculated with MOLM-14 cells stably expressing firefly luciferase and GFP on day 0, and five million CAR T cells per mouse were administered on study day 5. Tumor growth kinetics were measured by IVIS bioluminescent imaging on study days 14, 21, 28, 35, and CAR T function in mouse blood was assessed on study day 19.

As shown in FIG. 10A, mice engrafted with MOLM-14 tumors and left untreated (TA), or administered untransduced T cell control (UTD) succumbed to disease by study day 14. CAR constructs 1936 and 1939, demonstrated partial efficacy and delayed tumor growth and prolonged survival. Strikingly, CAR construct 1906 and the comparator construct 1940 mediated MOML-14 tumor rejection and all animals in these groups have survived to the end of the study at day 39 (FIGS. 10A and 10B).

Blood was taken from each animal on study day 19 in order to evaluate the CAR T cell levels in blood, MOLM-14 tumor cell levels in blood, and the levels of CAR T-secreted blood cytokines for each treatment group. The absolute CART and tumor cell numbers in blood samples were measured by flow cytometry (FIG. 11A, left panel). While there were no significant differences in the numbers of CAR T cells in each group, CAR T cells expressing construct 1906 tended to be higher than in other groups, followed by CAR comparator construct 1940. Interestingly, T cell levels were also high in the UTD control group, comprised of untransduced T cells, possibly due to the initial high number of cells infused in this group (8.0×10$^6$ cells/mouse). Notably, we detected a statistically significant reduction in the numbers of circulating blood MOLM-14 tumor cells in all CAR T groups as compared to UTD control (FIG. 11A, right panel). Furthermore, when comparing CAR T groups to each other, CAR 1906 and 1940 spurred the strongest reduction in MOLM-14 cells, which was significantly greater than that for CARs 1936 and 1939. Therefore, C A R 1906 and 1940 were the most efficient in controlling MOLM-14 levels in the blood, followed by CAR 1936 and CAR1939.

Measurable levels of inflammatory cytokines GM-CSF, IFN gamma and IL-2 were detected in mice dosed with CAR T cells or UTD controls. Although the differences between the levels of these cytokines were not significant, plasma GM-CSF and IFN gamma levels for construct 1906 tended to be higher, whereas the levels of IL-2 tended to be increased for CAR 1906 as well as CAR constructs 1940 and 1936 (FIG. 11B). These results underscore the elevated secretion of inflammatory cytokines by activated CAR T cells. No significant differences were detected between experimental groups, possibly because on study day 19 CAR T cells may have already been past maximal activation (of note differences in tumor burden are detected as early as study day 14, FIG. 10A), however CAR 1906 and 1940 which were most effective in tumor rejection also tended to secrete greater levels of cytokines.

In summary, high functionality of novel fully human anti-CD33 CAR constructs LTG1906, and partial functionality of constructs LTG1936 and LTG1939 (Table 2 infra) was demonstrated in vitro and in vivo. It is conceivable that the functionality of constructs LTG1936 and LTG1939 may be further improved by re-design of CAR spacer, linker or co-stimulatory domains, in order to allow better access to the specific epitopes they target, or increase the levels of CAR response to tumor epitope binding. The VH-based anti-CD33 CAR construct LTG1905 had low cytolytic effect, despite detectable surface expression by flow cytometry and high cytokine secretion. The ScFv-based CAR T constructs LTG1937 and LTG1938 were also inefficient in lysing target cell lines in vitro despite being highly expressed.

Example 3

Improved Functional Properties of CD33 CAR Moieties May be Achieved by Varying the Structure of Anti-CD33 CARs Expressing Fully Human Heavy Chain Only, or ScFv-Based Binding Sequences In this example, different structural configurations of anti-CD33 CAR T cells derived from novel fully human immunoglobulin heavy chain only or scFv binder sequences are described.

CART cells are postulated to secrete greater or lower levels of inflammatory cytokines, such as IL-2, IFN gamma, TNF alpha when challenged with antigen-expressing tumor cells, such as by incorporation in a CAR structure of a single CD28-derived vs CD137/4-1BB derived co-stimulatory domain ($2^{nd}$ generation CARs) in frame with activation domain, such as CD3 zeta, lacking co-stimulatory domain ($1^{st}$ generation CAR), or incorporating multiple co-stimulatory domains in tandem ($3^{rd}$ generation CARs).

In some constructs, incorporation of novel hinge and transmembrane domains, such as domains derived from human TNFRSF19 sequences, may endow the CAR with enhanced potency in tumor cell killing and cytokine response.

In addition, by varying the length and composition of CAR hinge aka linker domain, such as by replacing the CD8 alpha derived linker domain with TNFRSSF19-derived domain of varying length, or a domain derived from immunoglobulin constant region and/or hinge, such as IgG1-derived linker domain, or IgG4-derived linker domain, incorporating CH2, and/or CH3, and/or Hinge domain of the immunoglobulin molecule or their modifications, may yield better accessibility of tumor antigen to CAR binding domain. This is due to the fact that appropriate length and flexibility of the CAR hinge/linker domain are necessary for optimal accessibility, binding to tumor antigen, and CAR T cell activation.

Furthermore, incorporation of a tag molecule in CAR construct sequence that is expressed on CAR T cell surface is useful for 1) CAR T cell identification by flow cytometry during manufacturing, and in clinical applications, 2) CAR T cell sorting/isolation during manufacturing, 3) as a suicide tag for elimination of CAR T cells from patient's body in case of CAR-associated toxicity, such as B cell aplasia in response to anti-CD19 CAR, cytokine release syndrome, or CAR-associated neurotoxicity. For this purpose, the CAR construct sequence may include a truncated ectodomain and transmembrane portion of a native transmembrane protein, such as HER1/EGFR, HER2/Neu/erbB-2, NGFR/LNGFR/CD271, CD19, CD20 or other proteins. Mimotopes of these or other sequences may be used as well. Removal of tagged CAR T cells from patient's circulation will be achieved by administration of a tag-reactive clinical-grade antibody, such as antibody targeting EGFR (Cetuximab), HER2 (Trastuzumab), CD20 (Rituximab) or other proteins.

Select examples of the above mentioned CAR configurations are depicted in FIGS. 12A-12F, respectively. The anti-CD33 CAR constructs depicted were designed using CD33 binding sequences derived from immunoglobulin VH domain CD33_4, however, binder sequences in ScFv format may be used as well.

Materials and Methods:

(a) Creation of Chimeric Antigen Receptor (CAR)—Expression Vectors

CAR antigen-binding domain sequences were derived from human anti-CD33 ScFv or heavy chain variable fragments. CAR T constructs were generated by linking the binder sequence in frame to CD8a linking and transmembrane domains (UniProt sequence ID P01732, aa 138-206), and then to 4-1BB (CD137, aa 214-255, UniProt sequence ID Q07011) signaling domain and CD3 zeta signaling domain (CD247, aa 52-163, Ref sequence ID: NP 000725.1). For some constructs, CD28 costimulatory sequence (UniProt ID: P10747, transmembrane domain, aa 153-179) rather than 4-1BB costimulatory sequence was used. In some constructs the CD8 linking and/or transmembrane domain were replaced with domains of various length derived from TNFRSF19 protein (UniProt ID: Q9NS68). For some sequences, truncated epidermal growth factor receptor (tEGFR) tag (UniProt ID: P00533, various sequences) was incorporated in CAR construct via 2A peptide, to enable tagging of transduced cells in vitro and as a suicide switch for in vivo applications. CAR constructs sequences were cloned into a third generation lentiviral plasmid backbone (Lentigen Technology Inc., Gaithersburg, Md.). Lentiviral vector (LV) containing supernatants were generated by transient transfection of HEK 293T cells and vector pelleted by centrifugation of lentiviral vector-containing supernatants, and stored at −80° C.

TABLE 2

Summary of Expression and Function-Anti-CD33 CARs

| Experimental Group | CAR Expression | Cytolysis | Cytokines level | In vivo Tumor Rejection |
|---|---|---|---|---|
| NT or UTD (non-transduced control) | Undetected | None | N/A/ undetected | No |
| LTG1398 GFP | N/A/ undetected | None | N/A/ undetected | N/A |
| LTG1905 CAR | Detected | Low | Very High | N/A |
| LTG1906 CAR | Detected | High | High | Yes |
| LTG1936 CAR | Detected | High | High TNFa, IFNg/lowIL-2 | Partial |
| LTG1937 CAR | Detected | None | Low | N/A |
| LTG1938 CAR | Detected | None | Low | N/A |
| LTG1939 CAR | Detected | High | High TNFa, IFNg/lowIL-2 | Partial |
| LTG1940 CAR | Detected | High | High | Yes |

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

REFERENCE TO THE SEQUENCE LISTING

This application contains a Sequence Listing electronically submitted to the United States Patent and Trademark Office via a PDF file entitled "Sequence Listing". The Sequence Listing is incorporated by reference.

SEQUENCES OF THE DISCLOSURE

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

```
                                                                   SEQ ID NO: 1
nucleotide sequence of CD33-reactive immunoglobulin heavy chain
variable domain (VH-2)
gaggtgcagctggtggagtctgggggaggcttggtacagcctggagggtccctgagactctcctgtgcagcctctggattcacctt cagtagctatggcatgagctgggtccgccaggctccaaggaagggcctggagtggattggggaaatcaatcatagtggaagcaccaactac aacccgtccctcaagagtcgagtcaccatctccagagacaattccaagaacacgctgtatctgcaaatgaacagcctgagagccgaggaca cagccacgtattactgtgcgagaccccctcaactactactactacatggacgtctggggcaaagggaccacggtcaccgtctcctca SEQ ID NO: 2
amino acid sequence of CD33-reactive immunoglobulin heavy chain
variable domain (VH-2)
E V Q L V E S G G G L V Q P G G S L R L S C A A S G F T F S S Y

G M S W V R Q A P R K G L E W I G E I N H S G S T N Y N P S L K S R

V T I S R D N S K N T L Y L Q M N S L R A E D T A T Y Y C A R P L N

Y Y Y Y Y M D V W G K G T T V T V S S

SEQ ID NO: 3
nucleotide sequence of CD33-reactive immunoglobulin heavy chain
variable domain (VH-4)
gaggtgcagctggtggagtctgggggaggcttggtacagcctggagggtccctgagactctcctgtgcagcctctggattcacctt cagtagctatggcatgagctgggtccgccaggctccaagacaagggcttgagtgggtggccaacataaagcaagatggaagtgagaaata ctatgcggactcagtgaagggccgattcaccatctccagagacaattccaagaacacgctgtatctgcaaatgaacagcctgagagccgagg acacagccacgtattactgtgcgaaagaaaatgtggactggggccagggcaccctggtcaccgtctcctca SEQ ID NO: 4
amino acid sequence of CD33-reactive immunoglobulin heavy chain
variable domain (VH-4)
E V Q L V E S G G G L V Q P G G S L R L S C A A S G F T F S S Y

G M S W V R Q A P R Q G L E W V A N I K Q D G S E K Y Y A D S V K

G R F T I S R D N S K N T L Y L Q M N S L R A E D T A T Y Y C A K E

N V D W G Q G T L V T V S S

SEQ ID NO: 5
nucleotide sequence of CD3 3-reactive ScFv 9 binding domain
caggtgcagctggtgcaatctggggcagaggtgaaaaagcccggggagtctctgaggatctcctgtaagggttctggattcagttttcccacc tactggatcggctgggtgcgccagatgcccgggaaaggcctggagtggatggggatcatctatcctggtgactctgataccagatacagccc gtccttccaaggccaggtcaccatctcagccgacaagtccatcagcaccgcctacctgcagtggagcagcctgaaggcctcggacaccgcc atgtattactgtgcgagactagttggagatggctacaatacgggggcttttgatatctggggccaagggacaatggtcaccgtctcttcaggag gtggcgggtctggtggtggcggtagcggtggtggcggatccgatattgtgatgacccacactccactctctctgtccgtcaccctggacagc
```

```
cggcctccatctcctgcaagtctagtcagagcctcctgcatagtaatggaaagacctatttgtattggtacctgcagaagccaggccagcctcc acagctcctgatctatggagcttccaaccggttctctggagtgccagacaggttcagtggcagcgggtcagggacagatttcacactgaaaat cagccgggtggaggctgaggatgttggggtttattactgcatgcaaagtatacagcttcctatcaccttcGgccaagggacacgactggagat taaa
```

SEQ ID NO: 6
amino acid sequence of CD33-reactive ScFv 9 binding domain
```
Q V Q L V Q S G A E V K K P G E S L R I S C K G S G F S F P T Y

W I G W V R Q M P G K G L E W M G I I Y P G D S D T R Y S P S F Q G

Q V T I S A D K S I S T A Y L Q W S S L K A S D T A M Y Y C A R L V

G D G Y N T G A F D I W G Q G T M V T V S S G G G G S G G G G S G

G G G S D I V M T H T P L S L S V T P G Q P A S I S C K S S Q S L L H

S N G K T Y L Y W Y L Q K P G Q P P Q L L I Y G A S N R F S G V P D

R F S G S G S G T D F T L K I S R V E A E D V G V Y Y C M Q S I Q L P

I T F G Q G T R L E I K
```

SEQ ID NO: 7
nucleotide sequence of CD33-reactive ScFv 10 binding domain
```
caggtacagctgcagcagtcaggtccaggactggtgaagccctcgcagaccctctcactcacctgtgccatctccggggacagtgtctctag caacactgctgcttggaactggatcaggcagtccccatcgagaggccttgagtggctgggaaggacatactacaggtccaagtggtat aatgattatgcagtccctgtgaaaagtcgaataaccatcaacccagacacatccaagaaccagttctccctgcagctgaactctgtgactcccg aggacacggctgtgtattactgtgcaagagaaacgtattactatggttcggggagttattgggatgcttttgatatctggggccaagggaccac ggtcaccgtctcctcaggaggtggcgggtctggtagtggcggtagcggtggtggcggatcccagtctgtcgtgacgcagccgccctcagtg tctgcggccccaggacagaaggtcaccatctcctgctctggaagcagctccaacattgggaataattatgtatcctggtaccagcagctccca ggcacggcccccaaactcttcatctataaaaataatcagcggccctcagaggtccctgaccgattctctggctccaagtctggcacctcagcct ccctggccatcagtgggctccagtctgacgatgaggctgactactactgtgcagcatgggatgacaggctgaatggatatgtcttcggaactg ggaccaaggtcaccgtccta
```

SEQ ID NO: 8
amino acid sequence of CD33-reactive ScFv 10 binding domain
```
Q V Q L Q Q S G P G L V K P S Q T L S L T C A I S G D S V S S N

T A A W N W I R Q S P S R G L E W L G R T Y Y R S K W Y N D Y A V P

V K S R I T I N P D T S K N Q F S L Q L N S V T P E D T A V Y Y C A R

E T Y Y Y G S G S Y W D A F D I W G Q G T T V T V S S G G G G S G S

G G S G G G S Q S V V T Q P P S V S A A P G Q K V T I S C S G S S S

N I G N N Y V S W Y Q Q L P G T A P K L F I Y K N N Q R P S E V P D

R F S G S K S G T S A S L A I S G L Q S D D E A D Y Y C A A W D D R

L N G Y V F G T G T K V T V L
```

SEQ ID NO: 9
nucleotide sequence of CD33-reactive ScFv 12 binding domain
```
caggtacagctgcagcagtcaggtccaggactggtgaagccctcgcagaccctctcactcacctgtgccatctccggggacagtgtctctag caacagtgctgcttggaactggatcaggcagtccccatcgagaggccttgagtggctgggagggacatactacaggtccaagtggtataatg attatgcagtatctgtgaaaagtcgaataattatcaacgcagacacatcgaagaaccagttctccctgcagctgaactctgtgactcccgagga cacggctgtgtattactgtgcgaggggatattactatgatagtaccgactggttcgaccctggggccagggaaccctggtcaccgtctcctca ggaggtggcgggtctggtggtggcggtagcggtggtggcggatcctcttctgagctgactcaggacccaactgtgtctgtggccttgggaca
```

```
gacagtcaggatcacatgccaaggagacagcctcagaagctattatgcaagctggtaccagcagaagccaggacaggcccctgtacttgtc atctatggtaaaaacaaccggccctcagggatcccagaccgattctctggctccagctcaggaaacacagcttccttgaccatcactggggct caggcggaagatgaggctgactattactgttcctcccgggacggcagtggtcatccatatctcttcggacctgggaccaaggtcaccgttctt
```

SEQ ID NO: 10
amino acid sequence of CD33-reactive ScFv 12 binding domain
```
Q V Q L Q Q S G P G L V K P S Q T L S L T C A I S G D S V S S N

S A A W N W I R Q S P S R G L E W L G G T Y Y R S K W Y N D Y A V S

V K S R I I I N A D T S K N Q F S L Q L N S V T P E D T A V Y Y C A R

G Y Y Y D S T D W F D P W G Q G T L V T V S S G G G G S G G G G S

G G G G S S S E L T Q D P T V S V A L G Q T V R I T C Q G D S L R S Y

Y A S W Y Q Q K P G Q A P V L V I Y G K N N R P S G I P D R F S G S S

S G N T A S L T I T G A Q A E D E A D Y Y C S S R D G S H P Y L F

G P G T K V T V L
```

SEQ ID NO: 11
nucleotide sequence CD33-reactive ScFv 15 binding domain
```
gaggtccagctggtgcagtctggagcagaggtgaaaaagcccggggagtctctgaagatctcctgtaagggttctggatacagctttaccag ctactggatcggctgggtgcgccagatgcccgggaaaggcctggagtggatggggatcatctatcctggtgactctgataccagatacagcc cgtccttccaaggccaggtcaccatctcagccgacaagtccatcagcaccgcctacctgcagtggagcagcctgaaggcctcggacaccgc catgtattactgtgcgagactgactacggctgggggtatggacgtctggggccaagggaccacggtcaccgtctcctcaggaggtggcggg tctggtggtggcggtagcggtggtggcggatccgaaattgtgctgactcagtctccactctccctgcccgtcacccttggacagccggcctcc atctcctgcaggtctagtcaaagcctcgtacacagtgatggaaacacctacttgagttggcttcaccagaggccaggccagcctccaagactc ctaatgtataagatttctaaccggttctctggggtcacagacagattcagtggcagcgggtcagggacagatttcacactgaaaatcagccgg gtggaggctgaggatgttggggtttattactgcatgcaaggtatacacctaccgctcactttcggcggagggaccAagctggagatcaaa
```

SEQ ID NO: 12
amino acid sequence of CD33-reactive ScFv 15 binding domain
```
E V Q L V Q S G A E V K K P G E S L K I S C K G S G Y S F T S

Y W I G W V R Q M P G K G L E W M G I I Y P G D S D T R Y S P S F

Q G Q V T I S A D K S I S T A Y L Q W S S L K A S D T A M Y Y C A R

L T T A G G M D V W G Q G T T V T V S S G G G G S G G G G S G G G

G S E I V L T Q S P L S L P V T L G Q P A S I S C R S S Q S L V H S D

G N T Y L S W L H Q R P G Q P P R L L M Y K I S N R F S G V T D R F

S G S G S G T D F T L K I S R V E A E D V G V Y Y C M Q G I H L P L

T F G G G T K L E I K
```

SEQ ID NO: 13
nucleotide sequence of leader/signal peptide sequence
```
atgctgctgctggtgaccagcctgctgctgtgcgaactgccgcatccggcgtttctgctgattccg
```

SEQ ID NO: 14
amino acid sequence of leader/signal peptide sequence
MLLLVTSLLLCELPHPAFLLIP SEQ ID NO: 15
nucleotide sequence of LTG 1905_(EF1a- VH-2 CD33-CD8 TM-41BB-CD3 zeta)
```
ATGCTGCTGCTGGTGACCAGCCTGCTGCTGTGCGAACTGCCGCATCCGGCGTTT

TCTGCTGATTCCGGAGGTGCAGCTGGTGGAGTCTGGGGGAGGCTTGGTACAGCCTGG

AGGGTCCCTGAGACTCTCCTGTGCAGCCTCTGGATTCACCTTCAGTAGCTATGGCATG

AGCTGGGTCCGCCAGGCTCCAAGGAAGGGCCTGGAGTGGATTGGGGAAATCAATCAT

AGTGGAAGCACCAACTACAACCCGTCCCTCAAGAGTCGAGTCACCATCTCCAGAGAC
```

```
AATTCCAAGAACACGCTGTATCTGCAAATGAACAGCCTGAGAGCCGAGGACACAGCC

ACGTATTACTGTGCGAGACCCCTCAACTACTACTACTACATGGACGTCTGGGGCA

AAGGGACCACGGTCACCGTCTCCTCAGCGGCCGCAACTACCACCCCTGCCCCTCGGC

CGCCGACTCCGGCCCCAACCATCGCAAGCCAACCCCTCTCCTTGCGCCCCGAAGCTTG

CCGCCCGGCCGCGGGTGGAGCCGTGCATACCCGGGGGCTGGACTTTGCCTGCGATAT

CTACATTTGGGCCCCGCTGGCCGGCACTTGCGGCGTGCTCCTGCTGTCGCTGGTCATC

ACCCTTTACTGCAAGAGGGGCCGGAAGAAGCTGCTTTACATCTTCAAGCAGCCGTTC

ATGCGGCCCGTGCAGACGACTCAGGAAGAGGACGGATGCTCGTGCAGATTCCCTGAG

GAGGAAGAGGGGGGATGCGAACTGCGCGTCAAGTTCTCACGGTCCGCCGACGCCCCC

GCATATCAACAGGGCCAGAATCAGCTCTACAACGAGCTGAACCTGGGAAGGAGAGA

GGAGTACGACGTGCTGGACAAGCGACGCGGACGCGACCCGGAGATGGGGGGGAAAC

CACGGCGGAAAAACCCTCAGGAAGGACTGTACAACGAACTCCAGAAAGACAAGATG

GCGGAAGCCTACTCAGAAATCGGGATGAAGGGAGAGCGGAGGAGGGGAAAGGGTCA

CGACGGGCTGTACCAGGGACTGAGCACCGCCACTAAGGATACCTACGATGCCTTGCA

TATGCAAGCACTCCCACCCCGG
```

SEQ ID NO: 16
amino acid sequence of LTG 1905_(EF1a- VH-2 CD33 -CD8 TM-41BB-
CD3 zeta)

```
MLLLVTSLLLCELPHPAFLLIPEVQLVESGGGLVQPGGSLRLSCAASGFTFSSYGMS

WVRQAPRKGLEWIGEINHSGSTNYNPSLKSRVTISRDNSKNTLYLQMNSLRAEDTATYY

CARPLNYYYYYMDVWGKGTTVTVSSAAATTTPAPRPPTPAPTIASQPLSLRPEACRPAAG

GAVHTRGLDFACDIYIWAPLAGTCGVLLLSLVITLYCKRGRKKLLYIFKQPFMRPVQTTQ

EEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKGHDGLYQGLSTAT

KDTYDALHMQALPPR
```

SEQ ID NO: 17
nucleotide sequence of LTG 1906 (EF1a- VH-4 CD33 -CD8 TM-41BB-
CD3 zeta) nucleic acid sequence

```
ATGCTGCTGCTGGTGACCAGCCTGCTGCTGTGCGAACTGCCGCATCCGGCGTT

TCTGCTGATTCCGGAGGTGCAGCTGGTGGAGTCTGGGGGAGGCTTGGTACAGCCTGG

AGGGTCCCTGAGACTCTCCTGTGCAGCCTCTGGATTCACCTTCAGTAGCTATGGCATG

AGCTGGGTCCGCCAGGCTCCAAGACAAGGGCTTGAGTGGGTGGCCAACATAAAGCA

AGATGGAAGTGAGAAATACTATGCGGACTCAGTGAAGGGCCGATTCACCATCTCCAG

AGACAATTCCAAGAACACGCTGTATCTGCAAATGAACAGCCTGAGAGCCGAGGACAC

AGCCACGTATTACTGTGCGAAAGAAAATGTGGACTGGGGCCAGGGCACCCTGGTCAC

CGTCTCCTCAGCGGCCGCAACTACCACCCCTGCCCCTCGGCCGCCGACTCCGGCCCCA

ACCATCGCAAGCCAACCCCTCTCCTTGCGCCCCGAAGCTTGCCGCCCGGCCGCGGGT

GGAGCCGTGCATACCCGGGGGCTGGACTTTGCCTGCGATATCTACATTTGGGCCCCGC

TGGCCGGCACTTGCGGCGTGCTCCTGCTGTCGCTGGTCATCACCCTTTACTGCAAGAG

GGGCCGGAAGAAGCTGCTTTACATCTTCAAGCAGCCGTTCATGCGGCCCGTGCAGAC

GACTCAGGAAGAGGACGGATGCTCGTGCAGATTCCCTGAGGAGGAAGAGGGGGGAT

GCGAACTGCGCGTCAAGTTCTCACGGTCCGCCGACGCCCCCGCATATCAACAGGCC

AGAATCAGCTCTACAACGAGCTGAACCTGGGAAGGAGAGAGGAGTACGACGTGCTG
```

-continued

GACAAGCGACGCGGACGCGACCCGGAGATGGGGGGGAAACCACGGCGGAAAAACCC

TCAGGAAGGACTGTACAACGAACTCCAGAAAGACAAGATGGCGGAAGCCTACTCAG

AAATCGGGATGAAGGGAGAGCGGAGGAGGGGAAAGGGTCACGACGGGCTGTACCAG

GGACTGAGCACCGCCACTAAGGATACCTACGATGCCTTGCATATGCAAGCACTCCCA

CCCCGG

SEQ ID NO: 18 amino acid sequence of LTG 1906 (EF1a-VH-4 CD33 -CD8 TM-41BB-
CD3 zeta)
MLLLVTSLLLCELPHPAFLLIPEVQLVESGGGLVQPGGSLRLSCAASGFTFSSYGMS

WVRQAPRQGLEWVANIKQDGSEKYYADSVKGRFTISRDNSKNTLYLQMNSLRAEDTAT

YYCAKENVDWGQGTLVTVSSAAATTTPAPRPPTPAPTIASQPLSLRPEACRPAAGGAVHT

RGLDFACDIYIWAPLAGTCGVLLLSLVITLYCKRGRKKLLYIFKQPFMRPVQTTQEEDGCS

CRFPEEEEGGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLSTATKDTYD

ALHMQALPPR

SEQ ID NO. 19 nucleotide sequence of LTG1936_(EF1a_ScFv9 CD33 CD8 TM-41BB-
CD3 zeta CAR)
ATGCTGCTGCTGGTGACCAGCCTGCTGCTGTGCGAACTGCCGCATCCGGCGTT

TCTGCTGATTCCGCAGGTGCAGCTGGTGCAATCTGGGGCAGAGGTGAAAAAGCCCGG

GGAGTCTCTGAGGATCTCCTGTAAGGGTTCTGGATTCAGTTTTCCCACCTACTGGATC

GGCTGGGTGCGCCAGATGCCCGGGAAAGGCCTGGAGTGGATGGGGATCATCTATCCT

GGTGACTCTGATACCAGATACAGCCCGTCCTTCCAAGGCCAGGTCACCATCTCAGCC

GACAAGTCCATCAGCACCGCCTACCTGCAGTGGAGCAGCCTGAAGGCCTCGGACACC

GCCATGTATTACTGTGCGAGACTAGTTGGAGATGGCTACAATACGGGGGCTTTTGAT

ATCTGGGGCCAAGGGACAATGGTCACCGTCTCTTCAGGAGGTGGCGGGTCTGGTGGT

GGCGGTAGCGGTGGTGGCGGATCCGATATTGTGATGACCCACACTCCACTCTCTCTGT

CCGTCACCCCTGGACAGCCGGCCTCCATCTCCTGCAAGTCTAGTCAGAGCCTCCTGCA

TAGTAATGGAAAGACCTATTTGTATTGGTACCTGCAGAAGCCAGGCCAGCCTCCACA

GCTCCTGATCTATGAGCTTCCAACCGGTTCTCTGGAGTGCCAGACAGGTTCAGTGGC

AGCGGGTCAGGGACAGATTTCACACTGAAAATCAGCCGGGTGGAGGCTGAGGATGTT

GGGGTTTATTACTGCATGCAAAGTATACAGCTTCCTATCACCTTCGGCCAAGGGACAC

GACTGGAGATTAAAGCGGCCGCAACTACCACCCCTGCCCCTCGGCCGCCGACTCCGG

CCCCAACCATCGCAAGCCAACCCCTCTCCTTGCGCCCCGAAGCTTGCCGCCCGGCCGC

GGGTGGAGCCGTGCATACCCGGGGCTGGACTTTGCCTGCGATATCTACATTTGGGC

CCCGCTGGCCGGCACTTGCGGCGTGCTCCTGCTGTCGCTGGTCATCACCCTTTACTGC

AAGAGGGGCCGGAAGAAGCTGCTTTACATCTTCAAGCAGCCGTTCATGCGGCCCGTG

CAGACGACTCAGGAAGAGGACGGATGCTCGTGCAGATTCCCTGAGGAGGAAGAGGG

GGGATGCGAACTGCGCGTCAAGTTCTCACGGTCCGCCGACGCCCCCGCATATCAACA

GGGCCAGAATCAGCTCTACAACGAGCTGAACCTGGGAAGGAGAGAGGAGTACGACG

TGCTGGACAAGCGACGCGGACGCGACCCGGAGATGGGGGGGAAACCACGGCGGAAA

AACCCTCAGGAAGGACTGTACAACGAACTCCAGAAAGACAAGATGGCGGAAGCCTA

```
CTCAGAAATCGGGATGAAGGGAGAGCGGAGGAGGGGAAAGGGTCACGACGGGCTGT

ACCAGGGACTGAGCACCGCCACTAAGGATACCTACGATGCCTTGCATATGCAAGCAC

TCCCACCCCGG
```

SEQ ID NO. 20

```
amino acid sequence of LTG1936_(EF1a_ScFv9 CD33 CD8 TM-41BB-
CD3 zeta)
MLLLVTSLLLCELPHPAFLLIPQVQLVQSGAEVKKPGESLRISCKGSGFSFPTYWIGWVRQ

MPGKGLEWMGITYPGDSDTRYSPSFQGQVTISADKSISTAYLQWSSLKASDTAMYYCARL

VGDGYNTGAFDIWGQGTMVTVSSGGGGSGGGGSGGGGSDIVMTHTPLSLSVTPGQPASI

SCKSSQSLLHSNGKTYLYWYLQKPGQPPQLLIYGASNRFSGVPDRFSGSGSGTDFTLKISR

VEAEDVGVYYCMQSIQLPITFGQGTRLEIKAAATTTPAPRPPTPAPTIASQPLSLRPEACRP

AAGGAVHTRGLDFACDIYIWAPLAGTCGVLLLSLVITLYCKRGRKKLLYIFKQPFMRPVQ

TTQEEDGCSCRFPEEEEGGCELRVKFSRSADAPAYQQGQNQLYNELNLGRREEYDVLDK

RRGRDPEMGGKPRRKNPQEGLYNELQKDKMAEAYSEIGMKGERRRGKGHDGLYQGLS

TATKDTYDALHMQALPPR
```

SEQ ID NO. 21

```
nucleotide sequence of LTG1937_(EF1a_ScFv10 CD33 CD8 TM-41BB-
CD3 zeta CAR)
ATGCTGCTGCTGGTGACCAGCCTGCTGCTGTGCGAACTGCCGCATCCGGCGTT

TCTGCTGATTCCGCAGGTACAGCTGCAGCAGTCAGGTCCAGGACTGGTGAAGCCCTC

GCAGACCCTCTCACTCACCTGTGCCATCTCCGGGGACAGTGTCTCTAGCAACACTGCT

GCTTGGAACTGGATCAGGCAGTCCCCATCGAGAGGCCTTGAGTGGCTGGGAAGGACA

TACTACAGGTCCAAGTGGTATAATGATTATGCAGTCCCTGTGAAAAGTCGAATAACC

ATCAACCCAGACACATCCAAGAACCAGTTCTCCCTGCAGCTGAACTCTGTGACTCCCG

AGGACACGGCTGTGTATTACTGTGCAAGAGAAACGTATTACTATGGTTCGGGGAGTT

ATTGGGATGCTTTTGATATCTGGGGCCAAGGGACCACGGTCACCGTCTCCTCAGGAG

GTGGCGGGTCTGGTAGTGGCGGTAGCGGTGGTGGCGGATCCCAGTCTGTCGTGACGC

AGCCGCCCTCAGTGTCTGCGGCCCCAGGACAGAAGGTCACCATCTCCTGCTCTGGAA

GCAGCTCCAACATTGGGAATAATTATGTATCCTGGTACCAGCAGCTCCCAGGCACGG

CCCCCAAACTCTTCATCTATAAAAATAATCAGCGGCCCTCAGAGGTCCCTGACCGATT

CTCTGGCTCCAAGTCTGGCACCTCAGCCTCCCTGGCCATCAGTGGGCTCCAGTCTGAC

GATGAGGCTGACTACTACTGTGCAGCATGGGATGACAGGCTGAATGGATATGTCTTC

GGAACTGGGACCAAGGTCACCGTCCTAGCGGCCGCAACTACCACCCCTGCCCCTCGG

CCGCCGACTCCGGCCCCAACCATCGCAAGCCAACCCCTCTCCTTGCGCCCCGAAGCTT

GCCGCCCGGCCGCGGGTGGAGCCGTGCATACCCGGGGGCTGGACTTTGCCTGCGATA

TCTACATTTGGGCCCCGCTGGCCGGCACTTGCGGCGTGCTCCTGCTGTCGCTGGTCAT

CACCCTTTACTGCAAGAGGGGCCGGAAGAAGCTGCTTTACATCTTCAAGCAGCCGTT

CATGCGGCCCGTGCAGACGACTCAGGAAGAGGACGGATGCTCGTGCAGATTCCCTGA

GGAGGAAGAGGGGGGATGCGAACTGCGCGTCAAGTTCTCACGGTCCGCCGACGCCCC

CGCATATCAACAGGGCCAGAATCAGCTCTACAACGAGCTGAACCTGGGAAGGAGAG

AGGAGTACGACGTGCTGGACAAGCGACGCGGACGCGACCCGGAGATGGGGGGGAAA

CCACGGCGGAAAAACCCTCAGGAAGGACTGTACAACGAACTCCAGAAAGACAAGAT

GGCGGAAGCCTACTCAGAAATCGGGATGAAGGGAGAGCGGAGGAGGGGAAAGGGTC
```

-continued
ACGACGGGCTGTACCAGGGACTGAGCACCGCCACTAAGGATACCTACGATGCCTTGC

ATATGCAAGCACTCCCACCCCGG

SEQ ID NO: 22 amino acid sequence of LTG1937_(EF1a_ScFv10 CD33 CD8 TM-41BB-CD3 zeta)
MLLLVTSLLLCELPHPAFLLIPQVQLQQSGPGLVKPSQTLSLTCAISGDSVSSNTAA

WNWIRQSPSRGLEWLGRTYYRSKWYNDYAVPVKSRITINPDTSKNQFSLQLNSVTPEDT

AVYYCARETYYYGSGSYWDAFDIWGQGTTVTVSSGGGGSGSGGSGGGGSQSVVTQPPS

VSAAPGQKVTISCSGSSSNIGNNYVSWYQQLPGTAPKLFIYKNNQRPSEVPDRFSGSKSGT

SASLAISGLQSDDEADYYCAAWDDRLNGYVFGTGTKVTVLAAATTTPAPRPPTPAPTIAS

QPLSLRPEACRPAAGGAVHTRGLDFACDIYIWAPLAGTCGVLLLSLVITLYCKRGRKKLL

YIFKQPFMRPVQTTQEEDGCSCRFPEEEEGGCELRVKFSRSADAPAYQQGQNQLYNELNL

GRREEYDVLDKRRGRDPEMGGKPRRKNPQEGLYNELQKDKMAEAYSEIGMKGERRRG

KGHDGLYQGLSTATKDTYDALHMQALPPR

SEQ ID NO. 23 nucleotide sequence of LTG1938_(EF1a_ScFv12 CD33 CD8 TM-41BB-CD3 zeta)
ATGCTGCTGCTGGTGACCAGCCTGCTGCTGTGCGAACTGCCGCATCCGGCGTT

TCTGCTGATTCCGCAGGTACAGCTGCAGCAGTCAGGTCCAGGACTGGTGAAGCCCTC

GCAGACCCTCTCACTCACCTGTGCCATCTCCGGGGACAGTGTCTCTAGCAACAGTGCT

GCTTGGAACTGGATCAGGCAGTCCCCATCGAGAGGCCTTGAGTGGCTGGGAGGGACA

TACTACAGGTCCAAGTGGTATAATGATTATGCAGTATCTGTGAAAAGTCGAATAATT

ATCAACGCAGACACATCGAAGAACCAGTTCTCCCTGCAGCTGAACTCTGTGACTCCC

GAGGACACGGCTGTGTATTACTGTGCGAGGGGATATTACTATGATAGTACCGACTGG

TTCGACCCCTGGGGCCAGGGAACCCTGGTCACCGTCTCCTCAGGAGGTGGCGGGTCT

GGTGGTGGCGGTAGCGGTGGTGGCGGATCCTCTTCTGAGCTGACTCAGGACCCAACT

GTGTCTGTGGCCTTGGGACAGACAGTCAGGATCACATGCCAAGGAGACAGCCTCAGA

AGCTATTATGCAAGCTGGTACCAGCAGAAGCCAGGACAGGCCCCTGTACTTGTCATC

TATGGTAAAAACAACCGGCCCTCAGGGATCCCAGACCGATTCTCTGGCTCCAGCTCA

GGAAACACAGCTTCCTTGACCATCACTGGGGCTCAGGCGGAAGATGAGGCTGACTAT

TACTGTTCCTCCCGGGACGGCAGTGGTCATCCATATCTCTTCGGACCTGGGACCAAGG

TCACCGTTCTTGCGGCCGCAACTACCACCCCTGCCCCTCGGCCGCCGACTCCGGCCCC

AACCATCGCAAGCCAACCCCTCTCCTTGCGCCCCGAAGCTTGCCGCCCGGCCGCGGG

TGGAGCCGTGCATACCCGGGGGCTGGACTTTGCCTGCGATATCTACATTTGGGCCCCG

CTGGCCGGCACTTGCGGCGTGCTCCTGCTGTCGCTGGTCATCACCCTTTACTGCAAGA

GGGGCCGGAAGAAGCTGCTTTACATCTTCAAGCAGCCGTTCATGCGGCCCGTGCAGA

CGACTCAGGAAGAGGACGGATGCTCGTGCAGATTCCCTGAGGAGGAAGAGGGGGGA

TGCGAACTGCGCGTCAAGTTCTCACGGTCCGCCGACGCCCCCGCATATCAACAGGGC

CAGAATCAGCTCTACAACGAGCTGAACCTGGAAGGAGAGAGGAGTACGACGTGCT

GGACAAGCGACGCGGACGCGACCCGGAGATGGGGGGGAAACCACGGCGGAAAAAC

CCTCAGGAAGGACTGTACAACGAACTCCAGAAAGACAAGATGGCGGAAGCCTACTC

AGAAATCGGGATGAAGGGAGAGCGGAGGAGGGGAAAGGGTCACGACGGGCTGTACC

AGGGACTGAGCACCGCCACTAAGGATACCTACGATGCCTTGCATATGCAAGCACTCC

CACCCCGG

SEQ ID NO: 24 amino acid sequence of LTG1938_(EF1a_ScFv12 CD33 CD8 TM-41BB-CD3 zeta)
MLLLVTSLLLCELPHPAFLLIPQVQLQQSGPGLVKPSQTLSLTCAISGDSVSSNSAA

WNWIRQSPSRGLEWLGGTYYRSKWYNDYAVSVKSRIIINADTSKNQFSLQLNSVTPEDT

AVYYCARGYYYDSTDWFDPWGQGTLVTVSSGGGGSGGGGSGGGGSSSELTQDPTVSVA

LGQTVRITCQGDSLRSYYASWYQQKPGQAPVLVIYGKNNRPSGIPDRFSGSSSGNTASLTI

TGAQAEDEADYYCSSRDGSGHPYLFGPGTKVTVLAAATTTPAPRPPTPAPTIASQPLSLRP

EACRPAAGGAVHTRGLDFACDIYIWAPLAGTCGVLLLSLVITLYCKRGRKKLLYIFKQPF

MRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGL

YQGLSTATKDTYDALHMQALPPR

SEQ ID NO. 25 nucleotide sequence of LTG1939_(EF1a_ScFv15 CD33 CD8 TM-41BB-CD3 zeta)
ATGCTGCTGCTGGTGACCAGCCTGCTGCTGTGCGAACTGCCGCATCCGGCGTT

TCTGCTGATTCCGGAGGTCCAGCTGGTGCAGTCTGGAGCAGAGGTGAAAAAGCCCGG

GGAGTCTCTGAAGATCTCCTGTAAGGGTTCTGGATACAGCTTTACCAGCTACTGGATC

GGCTGGGTGCGCCAGATGCCCGGGAAAGGCCTGGAGTGGATGGGGATCATCTATCCT

GGTGACTCTGATACCAGATACAGCCCGTCCTTCCAAGGCCAGGTCACCATCTCAGCC

GACAAGTCCATCAGCACCGCCTACCTGCAGTGGAGCAGCCTGAAGGCCTCGGACACC

GCCATGTATTACTGTGCGAGACTGACTACGGCTGGGGGTATGGACGTCTGGGCCAA

GGGACCACGGTCACCGTCTCCTCAGGAGGTGGCGGGTCTGGTGGTGGCGGTAGCGGT

GGTGGCGGATCCGAAATTGTGCTGACTCAGTCTCCACTCTCCCTGCCCGTCACCCTTG

GACAGCCGGCCTCCATCTCCTGCAGGTCTAGTCAAAGCCTCGTACACAGTGATGGAA

ACACCTACTTGAGTTGGCTTCACCAGAGGCCAGGCCAGCCTCCAAGACTCCTAATGT

ATAAGATTTCTAACCGGTTCTCTGGGGTCACAGACAGATTCAGTGGCAGCGGGTCAG

GGACAGATTTCACACTGAAAATCAGCCGGGTGGAGGCTGAGGATGTTGGGGTTTATT

ACTGCATGCAAGGTATACACCTACCGCTCACTTTCGGCGGAGGGACCAAGCTGGAGA

TCAAAGCGGCCGCAACTACCACCCCTGCCCCTCGGCCGCCGACTCCGGCCCCAACCA

TCGCAAGCCAACCCCTCTCCTTGCGCCCCGAAGCTTGCCGCCCGGCCGCGGGTGGAG

CCGTGCATACCCGGGGGCTGGACTTTGCCTGCGATATCTACATTTGGGCCCCGCTGGC

CGGCACTTGCGGCGTGCTCCTGCTGTCGCTGGTCATCACCCTTTACTGCAAGAGGGGC

CGGAAGAAGCTGCTTTACATCTTCAAGCAGCCGTTCATGCGGCCCGTGCAGACGACT

CAGGAAGAGGACGGATGCTCGTGCAGATTCCCTGAGGAGGAAGAGGGGGGATGCGA

ACTGCGCGTCAAGTTCTCACGGTCCGCCGACGCCCCCGCATATCAACAGGGCCAGAA

TCAGCTCTACAACGAGCTGAACCTGGGAAGGAGAGAGGAGTACGACGTGCTGGACA

AGCGACGCGGACGCGACCCGGAGATGGGGGGGAAACCACGGCGGAAAAACCCTCAG

GAAGGACTGTACAACGAACTCCAGAAAGACAAGATGGCGGAAGCCTACTCAGAAAT

CGGGATGAAGGGAGAGCGGAGGAGGGGAAAGGGTCACGACGGGCTGTACCAGGGA

CTGAGCACCGCCACTAAGGATACCTACGATGCCTTGCATATGCAAGCACTCCCACCC

CGG

SEQ ID NO: 26 amino acid sequence of LTG1939_(EF1a_ScFv15 CD33 CD8 TM-
41BB-CD3 zeta)
MLLLVTSLLLCELPHPAFLLIPEVQLVQSGAEVKKPGESLKISCKGSGYSFTSYWIG

WVRQMPGKGLEWMGIIYPGDSDTRYSPSFQGQVTISADKSISTAYLQWSSLKASDTAMY

YCARLTTAGGMDVWGQGTTVTVSSGGGGSGGGGSGGGGSEIVLTQSPLSLPVTLGQPAS

ISCRSSQSLVHSDGNTYLSWLHQRPGQPPRLLMYKISNRFSGVTDRFSGSGSGTDFTLKIS

RVEAEDVGVYYCMQGIHLPLTFGGGTKLEIKAAATTTPAPRPPTPAPTIASQPLSLRPEAC

RPAAGGAVHTRGLDFACDIYIWAPLAGTCGVLLLSLVITLYCKRGRKKLLYIFKQPFMRP

VQTTQEEDGCSCRFPEEEEGGCELRVKFSRSADAPAYQQGQNQLYNELNLGRREEYDVL

DKRRGRDPEMGGKPRRKNPQEGLYNELQKDKMAEAYSEIGMKGERRRGKGHDGLYQG

LSTATKDTYDALHMQALPPR

SEQ ID NO: 27 nucleotide sequence of DNA CD8 transmembrane domain
atctacatct gggcgccctt ggccgggact tgtggggtcc ttctcctgtc actggttatc acccttact gc

SEQ ID NO: 28 amino acid sequence of CD8 transmembrane domain
Ile Trp Ala Pro Leu Ala Gly Thr Cys Gly Val Leu Leu Leu Ser Leu Val Ile Thr Leu Tyr Cys

SEQ ID NO: 29 nucleotide sequence of DNA CD8 hinge domain
accacgacgc cagcgccgcg accaccaaca ccggcgccca ccatcgcgtc gcagcccctg tccctgcgcc cagaggcgtg ccggccagcg cggggggcg cagtgcacac gagggggctg gacttcgcct gtgat

SEQ ID NO: 30 amino acid sequence of CD8 hinge domain
Thr Thr Thr Pro Ala Pro Arg Pro Pro Thr Pro Ala Pro Thr Ile Ala Ser Gln Pro Leu Ser Leu Arg Pro Glu Ala Cys Arg Pro Ala Ala Gly Gly Ala Val His Thr Arg Gly Leu Asp Phe Ala Cys Asp Ile Tyr

SEQ ID NO: 31 amino acid sequence of amino acid numbers 118 to 178 hinge region of
CD8.alpha. (NCBI RefSeq: NP.sub.--001759.3)
Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly Gly Cys Glu Leu

SEQ ID NO: 32 amino acid sequence of Human IgG CL sequence
Gly Gln Pro Lys Ala Ala Pro Ser Val Thr Leu Phe Pro Pro Ser Ser Glu Glu Leu Gln Ala Asn Lys Ala Thr Leu Val Cys Leu Ile Ser Asp Phe Tyr Pro Gly Ala Val Thr Val Ala Trp Lys Ala Asp Ser Ser Pro Val Lys Ala Gly Val Glu Thr Thr Thr Pro Ser Lys Gln Ser Asn Asn Lys Tyr Ala Ala Ser Ser Tyr Leu Ser Leu Thr Pro Glu Gln Trp Lys Ser His Arg Ser Tyr Ser Cys Gln Val Thr His Glu Gly Ser Thr Val Glu Lys Thr Val Ala Pro Thr Glu Cys Ser

SEQ ID NO: 33 nucleotide sequence of DNA signaling domain of 4-1BB
aaacggggca gaaagaaact cctgtatata ttcaaacaac catttatgag accagtacaa actactcaag aggaagatgg ctgtagctgc cgatttccag aagaagaaga aggaggatgt gaactg -continued SEQ ID NO: 34
amino acid sequence of signaling domain of 4-1BB
Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly Gly Cys Glu Leu SEQ ID NO: 35
nucleotide sequence of DNA signaling domain of CD3-zeta
agagtgaagt tcagcaggag cgcagacgcc cccgcgtaca agcagggcca gaaccagctc tataacgagc tcaatctagg acgaagagag gagtacgatg ttttggacaa gagacgtggc cgggaccctg agatgggggg aaagccgaga aggaagaacc ctcaggaagg cctgtacaat gaactgcaga aagataagat ggcggaggcc tacagtgaga ttgggatgaa aggcgagcgc cggaggggca aggggcacga tggcctttac caggtctca gtacagccac caaggacacc tacgacgccc ttcacatgca ggccctgccc cctcgc SEQ ID NO: 36
amino acid sequence of CD3 zeta
Arg Val Lys Phe Ser Arg Ser Ala Asp Ala Pro Ala Tyr Lys Gln Gly Gln Asn Gln Leu Tyr Asn Glu Leu Asn Leu Gly Arg Arg Glu Glu Tyr Asp Val Leu Asp Lys Arg Arg Gly Arg Asp Pro Glu Met Gly Gly Lys Pro Arg Arg Lys Asn Pro Gln Glu Gly Leu Tyr Asn Glu Leu Gln Lys Asp Lys Met Ala Glu Ala Tyr Ser Glu Ile Gly Met Lys Gly Glu Arg Arg Arg Gly Lys Gly His Asp Gly Leu Tyr Gln Gly Leu Ser Thr Ala Thr Lys Asp Thr Tyr Asp Ala Leu His Met Gln Ala Leu Pro Pro Arg SEQ ID NO: 37
nucleotide sequence of Scvf cd 19
gacatccaga tgacacagac tacatcctcc ctgtctgcct ctctgggaga cagagtcacc atcagttgca gggcaagtca ggacattagt aaatatttaa attggtatca gcagaaacca gatggaactg ttaaactcct gatctaccat acatcaagat tacactcagg agtcccatca aggttcagtg gcagtgggtc tggaacagat tattctctca ccattagcaa cctggagcaa gaagatattg ccacttactt ttgccaacag ggtaatacgc ttccgtacac gttcggaggg gggaccaagc tggagatcac aggtggcggt ggctcgggcg gtggtgggtc gggtggcggc ggatctgagg tgaaactgca ggagtcagga cctggcctgg tggcgccctc acagagcctg tccgtcacat gcactgtctc aggggtctca ttacccgact atggtgtaag ctggattcgc cagcctccac gaaagggtct ggagtggctg ggagtaatat ggggtagtga aaccacatac tataattcag ctctcaaatc cagactgacc atcatcaagg acaactccaa gagccaagtt ttcttaaaaa tgaacagtct gcaaactgat gacacagcca tttactactg tgccaaacat tattactacg gtggtagcta tgctatggac tactgggggcc aaggaacctc agtcaccgtc tcctca SEQ ID NO: 38
amino acid sequence of ScvF cd 19
Asp Ile Gln Met Thr Gln Thr Thr Ser Ser Leu Ser Ala Ser Leu Gly Asp Arg Val Thr Ile Ser Cys Arg Ala Ser Gln Asp Ile Ser Lys Tyr Leu Asn Trp Tyr Gln Gln Lys Pro Asp Gly Thr Val Lys Leu Leu Ile Tyr His Thr Ser Arg Leu His Ser Gly Val Pro Ser Arg Phe Ser Gly Ser Gly Ser Gly Thr Asp Tyr Ser Leu Thr Ile Ser Asn Leu Glu Gln Glu Asp Ile Ala Thr Tyr Phe Cys Gln Gln Gly Asn Thr Leu Pro Tyr Thr Phe Gly Gly Gly Thr Lys Leu Glu Ile Thr Gly Gly Gly Gly Ser 100

105 110 Gly Gly Gly Gly Ser Gly Gly Gly Gly Ser Glu Val Lys Leu Gln Glu Ser Gly Pro Gly Leu

Val Ala Pro Ser Gln Ser Leu Ser Val Thr Cys Thr Val Ser Gly Val Ser Leu Pro Asp Tyr Gly Val

Ser Trp Ile Arg Gln Pro Pro Arg Lys Gly Leu Glu Trp Leu Gly Val Ile Trp Gly Ser Glu Thr Thr

Tyr Tyr Asn Ser Ala Leu Lys Ser Arg Leu Thr Ile Ile Lys Asp Asn Ser Lys Ser Gln Val Phe Leu

Lys Met Asn Ser Leu Gln Thr Asp Asp Thr Ala Ile Tyr Tyr Cys Ala Lys His Tyr Tyr Tyr Gly Gly

Ser Tyr Ala Met Asp Tyr Trp Gly Gln Gly Thr Ser Val Thr Val Ser Ser

-continued nucleotide sequence of GMCSF leader peptide  
ATGCTGCTGCTGGTGACCAGCCTGCTGCTGTGCGAACTGCCGCATCCGGCGTTTCTGCTG

ATTCCG

SEQ ID NO: 39 amino acid sequence of GMCSF leader peptide  
MLLLVTSLLLCELPHPAFLLIP

SEQ ID NO: 40 nucleotide sequence of TNFRSF19 leader peptide  
GGCTCTGAAAGTGCTGTTGGAACAAGAAAAGACCTTCTTCACCTTGCTCGTGTTGCTGGG

GTACCTGTCCTGCAAAGTCACCTGT

SEQ ID NO: 41 amino acid sequence of TNFRSF19 leader peptide  
MALKVLLEQEKTFFTLLVLLGYLSCKVTC

SEQ ID NO: 42 nucleotide sequence of CD8 alpha leader peptide  
atggcgctgccggtgaccgcgctgctgctgccgctggcgctgctgctgcatgcggcgcgc ccg

SEQ ID NO: 43 amino acid sequence of CD8 alpha leader peptide  
MALPVTALLLPLALLLHAARP

SEQ ID NO: 44 nucleotide sequence of CD28 co-stimulatory domain  
CGGTCGAAGAGGTCCAGACTCTTGCACTCCGACTACATGAACATGACTCC

TAGAAGGCCCGGACCCACTAGAAAGCACTACCAGCCGTACGCCCCTCCTC

GGGATTTCGCCGCATACCGG TCC

SEQ ID NO: 45 amino acid sequence of CD28 co-stimulatory domain  
RSKRSRLLHSDYMNMTPRRPGPTRKHYQPYAPPRDFAAYRS

SEQ ID NO: 46 nucleotide sequence of CD3 zeta activation domain  
AGAGTGAAGTTCAGCCGCTCAGCCGATGCACCGGCCTACCAGCAGGGACA

GAACCAGCTCTACAACGAGCTCAACCTGGGTCGGCGGGAAGAATATGAC

GTGCTGGACAAACGGCGCGGCAGAGATCCGGAGATGGGGGGAAAGCCGA

GGAGGAAGAACCCTCAAGAGGGCCTGTACAACGAACTGCAGAAGGACAA

GATGGCGGAAGCCTACTCCGAGATCGGCATGAAGGGAGAACGCCGGAGA

GGGAAGGGTCATGACGGACTGTACCAGGGCCTGTCAACTGCCACTAAGGA

CACTTACGATGCGCTCCATATGCAAGCTTTGCCCCCGCGG

SEQ ID NO: 47 amino acid sequence of CD3 zeta activation domain  
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

SEQ ID NO: 48 nucleotide sequence of TNFRSF19 hinge and transmembrane domain  
(transmembrane domain underlined)  
GCGGCCGCGGTCGGATTCCAAGACATGGAATGCGTGCCCTGCGGCGACCCGCCACCTCCT

TACGAGCCGCACTGCGCATCGAAGGTCAACCTCGTGAAGATCGCGAGCACCGCGTCCTCA

CCCCGGGATACTGCTCTG <u>GCCGCCGTGATTTGTTCCGCCTTGGCCACCGTGCTTCTGGCC</u>

<u>CTGCTGATCCTCTGTGTGATC</u>

SEQ ID NO: 49

```
                                                                      SEQ ID NO: 50
amino acid sequence of TNFRSF19 hinge and transmembrane domain
(transmembrane domain underlined)
A A A V G F Q D M E C V P C G D P P P P Y E P H C A S K V N L V K I A S T A S S P R D T A

L A A V I C S A L A T V L L A L L I L C V I

SEQ ID NO: 51
nucleotide sequence of TNFRSF19 transmembrane domain
GCCGCCGTGATTTGTTCCGCCTTGGCCACCGTGCTTCTGGCCCTGCTGATCCTCTGTGTG

ATC

SEQ ID NO: 52
amino acid sequence of TNFRSF19 transmembrane domain
A A V I C S A L A T V L L A L L I L C V I SEQ ID NO: 53
nucleotide sequence of TNFRSF19 hinge domain
GCGGCCGCGGTCGGATTCCAAGACATGGAATGCGTGCCCTGCGGCGACCCGCCACCTCCT

TACGAGCCGCACTGCGCATCGAAGGTCAACCTCGTGAAGATCGCGAGCACCGCGTCCTCA

CCCCGGGATACTGCTCTG

SEQ ID NO: 54
amino acid sequence of TNFRSF19 hinge domain
A A A V G F Q D M E C V P C G D P P P P Y E P H C A S K V N L V K I A S T A S S P R D T A L SEQ ID NO: 55
nucleotide sequence of truncated TNFRSF19 hinge domain
TACGAGCCTCACTGCGCCAGCAAAGTCAACTTGGTGAAGATCGCGAGCACTGCCTCGTCC

CCTCGGGACACTGCTCTGGC

SEQ ID NO: 56
amino acid sequence of truncated TNFRSF19 hinge domain
Y E P H C A S K V N L V K I A S T A S S P R D T A L SEQ ID NO: 57
nucleotide sequence of CD8a hinge domain fused to TNFRSF19
transmembrane domain (transmembrane sequence underlined)
GCGGCCGCGCCCGCCCCTCGGCCCCCGACTCCTGCCCCGACGATCGCTTCCCAACCTCTC

TCGCTGCGCCCGGAAGCATGCCGGCCCGCCGCGGTGGCGCTGTCCACACTCGCGGACTG

GACTTTGATACCGCACTG GCGGCCGTGATCTGTAGCGCCCTGGCCACCGTGCTGCTGGCG

CTGCTCATCCTTTGCGTGATCTACTGCAAGCGGCAGCCTAGG

SEQ ID NO: 58
amino acid sequence of CD8a hinge domain fused to TNFRSF19
transmembrane domain (transmembrane sequence underlined)
A A A P A P R P P T P A P T I A S Q P L S L R P E A C R P A A G G A V

H T R G L D F D T A L A A V I C S A L A T V L L A L L I L C V I Y C K

R Q P R

SEQ ID NO: 59
nucleotide sequence of CD28 co-stimulatory domain
CGGTCGAAGAGGTCCAGACTCTTGCACTCCGACTACATGAACATGACTCCTAGAAGGCCC

GGACCCACTAGAAAGCACTACCAGCCGTACGCCCCTCCTCGGGATTTCGCCGCATACCGG

TCC

SEQ ID NO: 60
amino acid sequence of CD28 co-stimulatory domain
RSKRSRLLHSDYMNMTPRRPGPTRKHYQPYAPPRDFAAYRS SEQ ID NO: 61
nucleotide sequence of CD3 zeta version 2
cgcgtgaaatttagccgcagcgcggatgcgccggcgtatcagcagggccagaaccagctg tataacgaactgaacctgggccgccgcgaagaatatgatgtgctggataaacgccgcggc cgcgatccggaaatgggcggcaaaccgcgccgcaaaaacccgcaggaaggcctgtataac gaactgcagaaagataaaatggcggaagcgtatagcgaaattggcatgaaaggcgaacgc
```

```
cgccgcggcaaaggccatgatggcctgtatcagggcctgagcaccgcgaccaaagatacc tatgatgcgctgcatatgcaggcgctgccgccgcgc
```

SEQ ID NO: 62 amino acid sequence of CD3 zeta version 2
R V K F S R S A D A P A Y Q Q G Q N Q L Y N E L N L G R R

E E Y D V L D K R R G R D P E M G G K P R R K N P Q E G L

Y N E L Q K D M A E A Y S E I G M K G E R R R G K H D

G L Y Q G L S T A T K D T Y D A L H M Q A L P P R

SEQ ID NO: 63 nucleotide sequence of Furin P2A Furin
```
CGCGCGAAACGCAGCGGCAGCGGCGCGACCAACTTTAGCCTGCTGAAAC

AGGCGGGCGAT GTGGAAGAAAACCCGGGCCCGCGAGCAAAGAGG
```

SEQ ID NO: 64 amino acid sequence of Furin P2A Furin (furin sequence underlined)
<u>RAKR</u>SGSGATNFSLLKQAGDVEENPGP<u>RAKR</u>

SEQ ID NO: 65 nucleotide sequence of Furin T2A
```
AGAGCTAAACGCTCTGGGTCTGGTGAAGGACGAGGTAGCCTTCTTACGTG

CGGAGACGTGGAGGAAAACCCAGGACCC
```

SEQ ID NO: 66 amino acid sequence of Furin T2A (furin sequence underlined)
<u>RAKR</u>SGSGEGRGSLLTCGDVEENPGP

SEQ ID NO: 67 nucleotide sequence of truncated EGFR (tEGFR) tag
```
AGGAAGGTTTGCAATGGAATCGGTATAGGGGAGTTTAAGGATTCACTTAGCATAAACGCT

ACTAATATTAAACACTTCAAAAACTGTACGAGTATAAGTGGAGATCTTCACATTTTGCCG

GTTGCATTCCGAGGCGATTCATTCACCCACACGCCACCGCTTGACCCACAAGAATTGGAT

ATTCTTAAAACCGTTAAAGAAATAACGGGGTTTTTGCTCATTCAAGCGTGGCCAGAAAAT

CGCACTGACCTCCATGCTTTCGAGAACCTGGAGATTATAAGAGGACGAACTAAGCAGCAT

GGTCAATTCTCCCTTGCTGTGGTCAGCCTGAACATCACCAGTCTTGGTTTGCGGTCCCTC

AAGGAAATTTCAGATGGAGATGTCATCATAAGCGGCAACAAGAATTTGTGCTATGCAAAT

ACCATAAACTGGAAAAAACTGTTTGGCACTTCCGGCCAGAAAACCAAGATTATTTCAAAT

CGGGGTGAGAACAGCTGCAAAGCCACCGGCCAGGTTTGTCATGCCTTGTGCTCTCCGGAA

GGCTGTTGGGGGCCAGAACCCAGGGACTGCGTCAGTTGCAGAAACGTCTCAAGAGGCCGC

GAATGCGTTGACAAGTGTAACCTCCTTGAGGGTGAGCCACGAGAGTTTGTTGAGAACAGC

GAGTGTATACAATGTCACCCTGAATGTTTGCCCCAGGCTATGAATATAACCTGCACAGGC

CGCGGGCCTGATAACTGCATCCAGTGTGCTCATTACATAGATGGACCTCACTGTGTGAAA

ACCTGCCCGGCCGGAGTTATGGGAGAAAACAACACTCTGGTGTGGAAATACGCTGATGCA

GGCCACGTGTGCCACCTTTGTCACCCGAATTGTACATATGGGTGTACCGGTCCTGGACTT

GAAGGTTGCCCTACCAATGGCCCTAAAATACCCAGTATCGCAACTGGCATGGTAGGCGCT

CTTCTCTTGCTCTTGGTAGTTGCTCTCGGCATAGGTCTTTTTATG
```

SEQ ID NO: 68 amino acid sequence of truncated EGFR (tEGFR) tag
RKVCNGIGIGEFKDSLSINATNIKHFKNCTSISGDLHILPVAFRGDSFTHTPPLDPQELD

ILKTVKEITGFLLIQAWPENRTDLHAFENLEIIRGRTKQHGQFSLAVVSLNITSLGLRSL

KEISDGDVIISGNKNLCYANTINWKKLFGTSGQKTKIISNRGENSCKATGQVCHALCSPE

GCWGPEPRDCVSCRNVSRGRECVDKCNLLEGEPREFVENSECIQCHPECLPQAMNITCTG

RGPDNCIQCAHYIDGPHCVKTCPAGVMGENNTLVWKYADAGHVCHLCHPNCTYGCTGPGL

EGCPTNGPKIPSIATGMVGALLLLLVVALGIGLFM

SEQ ID NO: 69 nucleotide sequence of LTG1927 (EF1a-CD33_4-CD8 TM-CD28-CD3 zeta-cfrag)
ATGCTGCTGCTGGTGACCAGCCTGCTGCTGTGCGAACTGCCGCATCCGGCGTTTCTGCTG

ATTCCGGAGGTGCAGCTGGTGGAGTCTGGGGGAGGCTTGGTACAGCCTGGAGGGTCCCTG

AGACTCTCCTGTGCAGCCTCTGGATTCACCTTCAGTAGCTATGGCATGAGCTGGGTCCGC

CAGGCTCCAAGACAAGGGCTTGAGTGGGTGGCCAACATAAAGCAAGATGGAAGTGAGAAA

TACTATGCGGACTCAGTGAAGGGCCGATTCACCATCTCCAGAGACAATTCCAAGAACACG

CTGTATCTGCAAATGAACAGCCTGAGAGCCGAGGACACAGCCACGTATTACTGTGCGAAA

GAAAATGTGGACTGGGGCCAGGGCACCCTGGTCACCGTCTCCTCAGCGGCCGCGACTACC

ACTCCTGCACCACGGCCACCTACCCCAGCCCCCACCATTGCAAGCCAGCCACTTTCACTG

CGCCCCGAAGCGTGTAGACCAGCTGCTGGAGGAGCCGTGCATACCCGAGGGCTGGACTTC

GCCTGTGACATCTACATCTGGGCCCCATTGGCTGGAACTTGCGGCGTGCTGCTCTTGTCT

CTGGTCATTACCCTGTACTGCCGGTCGAAGAGGTCCAGACTCTTGCACTCCGACTACATG

AACATGACTCCTAGAAGGCCCGGACCCACTAGAAAGCACTACCAGCCGTACGCCCCTCCT

CGGGATTTCGCCGCATACCGGTCCAGAGTGAAGTTCAGCCGCTCAGCCGATGCACCGGCC

TACCAGCAGGGACAGAACCAGCTCTACAACGAGCTCAACCTGGGTCGGCGGGAAGAATAT

GACGTGCTGGACAAACGGCGCGGCAGAGATCCGGAGATGGGGGGAAAGCCGAGGAGGAAG

AACCCTCAAGAGGGCCTGTACAACGAACTGCAGAAGGACAAGATGGCGGAAGCCTACTCC

GAGATCGGCATGAAGGGAGAACGCCGGAGAGGGAAGGGTCATGACGGACTGTACCAGGGC

CTGTCAACTGCCACTAAGGACACTTACGATGCGCTCCATATGCAAGCTTTGCCCCCGCGG

SEQ ID NO: 70 amino acid sequence of LTG1927 (EF1a-CD33_4-CD8 TM-CD28-CD3 zeta-cfrag)
MLLLVTSLLLCELPHPAFLLIPEVQLVESGGGLVQPGGSLRLSCAASGFTFSSYGMSWVR

QAPRQGLEWVANIKQDGSEKYYADSVKGRFTISRDNSKNTLYLQMNSLRAEDTATYYCAK

ENVDWGQGTLVTVSSAAATTTPAPRPPTPAPTIASQPLSLRPEACRPAAGGAVHTRGLDF

ACDIYIWAPLAGTCGVLLLSLVITLYCRSKRSLLHSDYMNMTPRRPGPTRKHYQPYAPP

RDFAAYRSRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

SEQ ID NO: 71 nucleotide sequence of LTG_D0033 (Ef1a_CD33_4 VH TNFRSF19 H_TM_CD28z) nucleotide sequence
ATGCTGCTGCTGGTGACCAGCCTGCTGCTGTGCGAACTGCCGCATCCGGCGTTTCTGCTG

ATTCCGGAGGTGCAGCTGGTGGAGTCTGGGGGAGGCTTGGTACAGCCTGGAGGGTCCCTG

AGACTCTCCTGTGCAGCCTCTGGATTCACCTTCAGTAGCTATGGCATGAGCTGGGTCCGC

CAGGCTCCAAGACAAGGGCTTGAGTGGGTGGCCAACATAAAGCAAGATGGAAGTGAGAAA

TACTATGCGGACTCAGTGAAGGGCCGATTCACCATCTCCAGAGACAATTCCAAGAACACG

CTGTATCTGCAAATGAACAGCCTGAGAGCCGAGGACACAGCCACGTATTACTGTGCGAAA

GAAAATGTGGACTGGGGCCAGGGCACCCTGGTCACCGTCTCCTCAGCGGCCGCAGTCGGA

TTCCAAGACATGGAATGCGTGCCCTGCGGCGACCCGCCACCTCCTTACGAGCCGCACTGC

GCATCGAAGGTCAACCTCGTGAAGATCGCGAGCACCGCGTCCTCACCCCGGGATACTGCT

CTGGCCGCCGTGATTTGTTCCGCCTTGGCCACCGTGCTTCTGGCCCTGCTGATCCTCTGT

```
GTGATCCGGTCGAAGAGGTCCAGACTCTTGCACTCCGACTACATGAACATGACTCCTAGA

AGGCCCGGACCCACTAGAAAGCACTACCAGCCGTACGCCCCTCCTCGGGATTTCGCCGCA

TACCGGTCCAGAGTGAAGTTCAGCCGCTCAGCCGATGCACCGGCCTACCAGCAGGGACAG

AACCAGCTCTACAACGAGCTCAACCTGGGTCGGCGGGAAGAATATGACGTGCTGGACAAA

CGGCGCGGCAGAGATCCGGAGATGGGGGGAAAGCCGAGGAGGAAGAACCCTCAAGAGGGC

CTGTACAACGAACTGCAGAAGGACAAGATGGCGGAAGCCTACTCCGAGATCGGCATGAAG

GGAGAACGCCGGAGAGGGAAGGGTCATGACGGACTGTACCAGGGCCTGTCAACTGCCACT

AAGGACACTTACGATGCGCTCCATATGCAAGCTTTGCCCCCGCGG
```

SEQ ID NO: 72 amino acid sequence of LTG_D0033 (Ef1a_CD33_4 VH TNFRSF19 H_TM_CD28z) nucleotide sequence
```
MLLLVTSLLLCELPHPAFLLIPEVQLVESGGGLVQPGGSLRLSCAASGFTFSSYGMSWVR

QAPRQGLEWVANIKQDGSEKYYADSVKGRFTISRDNSKNTLYLQMNSLRAEDTATYYCAK

ENVDWGQGTLVTVSSAAAVGFQDMECVPCGDPPPPYEPHCASKVNLVKIASTASSPRDTA

LAAVICSALATVLLALLILCVIRSKRSRLLHSDYMNMTPRRPGPTRKHYQPYAPPRDFAA

YRSRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR
```

SEQ ID NO: 73 nucleotide sequence of LTG_D0034 (Ef1a_CD33_4 VH TNFRSF19 H_TM_4-1BBz) nucleotides
```
ATGCTGCTGCTGGTGACCAGCCTGCTGCTGTGCGAACTGCCGCATCCGGCGTTTCTGCTG

ATTCCGGAGGTGCAGCTGGTGGAGTCTGGGGGAGGCTTGGTACAGCCTGGAGGGTCCCTG

AGACTCTCCTGTGCAGCCTCTGGATTCACCTTCAGTAGCTATGGCATGAGCTGGGTCCGC

CAGGCTCCAAGACAAGGGCTTGAGTGGGTGGCCAACATAAAGCAAGATGGAAGTGAGAAA

TACTATGCGGACTCAGTGAAGGGCCGATTCACCATCTCCAGAGACAATTCCAAGAACACG

CTGTATCTGCAAATGAACAGCCTGAGAGCCGAGGACACAGCCACGTATTACTGTGCGAAA

GAAAATGTGGACTGGGGCCAGGGCACCCTGGTCACCGTCTCCTCAGCGGCCGCAGTCGGA

TTCCAAGACATGGAATGCGTGCCCTGCGGCGACCCGCCACCTCCTTACGAGCCGCACTGC

GCATCGAAGGTCAACCTCGTGAAGATCGCGAGCACCGCGTCCTCACCCCGGGATACTGCT

CTGGCCGCCGTGATTTGTTCCGCCTTGGCCACCGTGCTTCTGGCCCTGCTGATCCTCTGT

GTGATCAAGAGGGGCCGGAAGAAGCTGCTTTACATCTTCAAGCAGCCGTTCATGCGGCCC

GTGCAGACGACTCAGGAAGAGGACGGATGCTCGTGCAGATTCCTGAGGAGGAAGAGGGG

GGATGCGAACTGAGAGTGAAGTTCAGCCGCTCAGCCGATGCACCGGCCTACCAGCAGGGA

CAGAACCAGCTCTACAACGAGCTCAACCTGGGTCGGCGGGAAGAATATGACGTGCTGGAC

AAACGGCGCGGCAGAGATCCGGAGATGGGGGGAAAGCCGAGGAGGAAGAACCCTCAAGAG

GGCCTGTACAACGAACTGCAGAAGGACAAGATGGCGGAAGCCTACTCCGAGATCGGCATG

AAGGGAGAACGCCGGAGAGGGAAGGGTCATGACGGACTGTACCAGGGCCTGTCAACTGCC

ACTAAGGACACTTACGATGCGCTCCATATGCAAGCTTTGCCCCCGCGG
```

SEQ ID NO: 74 amino acid sequence of LTG_D0034 (Ef1a_CD33_4 VH TNFRSF19 H_TM_4-1BBz)
```
MLLLVTSLLLCELPHPAFLLIPEVQLVESGGGLVQPGGSLRLSCAASGFTFSSYGMSWVR

QAPRQGLEWVANIKQDGSEKYYADSVKGRFTISRDNSKNTLYLQMNSLRAEDTATYYCAK

ENVDWGQGTLVTVSSAAAVGFQDMECVPCGDPPPPYEPHCASKVNLVKIASTASSPRDTA

LAAVICSALATVLLALLILCVIKRGRKKLLYIFKQPFMRPVQTTQEEDGCSCRFPEEEEG
```

-continued

GCELRVKFSRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQALPPR

SEQ ID NO: 75 nucleotide sequence of LTG_ D0015 (Ef1a_CD33_4VH CD8 BBz T2A tEGFR)
ATGCTGCTGCTGGTGACCAGCCTGCTGCTGTGCGAACTGCCGCATCCGGCGTTTCTGCTG

ATTCCGGAGGTGCAGCTGGTGGAGTCTGGGGGAGGCTTGGTACAGCCTGGAGGGTCCCTG

AGACTCTCCTGTGCAGCCTCTGGATTCACCTTCAGTAGCTATGGCATGAGCTGGGTCCGC

CAGGCTCCAAGACAAGGGCTTGAGTGGGTGGCCAACATAAAGCAAGATGGAAGTGAGAAA

TACTATGCGGACTCAGTGAAGGGCCGATTCACCATCTCCAGAGACAATTCCAAGAACACG

CTGTATCTGCAAATGAACAGCCTGAGAGCCGAGGACACAGCCACGTATTACTGTGCGAAA

GAAAATGTGGACTGGGGCCAGGGCACCCTGGTCACCGTCTCCTCAGCGGCCGCAACTACC

ACCCCTGCCCCTCGGCCGCCGACTCCGGCCCCAACCATCGCAAGCCAACCCCTCTCCTTG

CGCCCCGAAGCTTGCCGCCCGGCCGCGGGTGGAGCCGTGCATACCCGGGGGCTGGACTTT

GCCTGCGATATCTACATTTGGGCCCCGCTGGCCGGCACTTGCGGCGTGCTCCTGCTGTCG

CTGGTCATCACCCTTTACTGCAAGAGGGGCCGGAAGAAGCTGCTTTACATCTTCAAGCAG

CCGTTCATGCGGCCCGTGCAGACGACTCAGGAAGAGGACGGATGCTCGTGCAGATTCCCT

GAGGAGGAAGAGGGGGGATGCGAACTGCGCGTCAAGTTCTCACGGTCCGCCGACGCCCCC

GCATATCAACAGGGCCAGAATCAGCTCTACAACGAGCTGAACCTGGGAAGGAGAGAGGAG

TACGACGTGCTGGACAAGCGACGCGGACGCGACCCGGAGATGGGGGGGAAACCACGGCGG

AAAAACCCTCAGGAAGGACTGTACAACGAACTCCAGAAAGACAAGATGGCGGAAGCCTAC

TCAGAAATCGGGATGAAGGGAGAGCGGAGGAGGGGAAAGGGTCACGACGGGCTGTACCAG

GGACTGAGCACCGCCACTAAGGATACCTACGATGCCTTGCATATGCAAGCACTCCCACCC

CGGTCTAGAGCTAAACGCTCTGGGTCTGGTGAAGGACGAGGTAGCCTTCTTACGTGCGGA

GACGTGGAGGAAAACCCAGGACCCCGAGCCAAACGAATGCTGCTGCTTGTTACAAGCCTT

TTGCTCTGCGAACTCCCCCATCCAGCTTTTCTCCTGATTCCAAGGAAGGTTTGCAATGGA

ATCGGTATAGGGGAGTTTAAGGATTCACTTAGCATAAACGCTACTAATATTAAACACTTC

AAAAACTGTACGAGTATAAGTGGAGATCTTCACATTTTGCCGGTTGCATTCCGAGGCGAT

TCATTCACCCACACGCCACCGCTTGACCCACAAGAATTGGATATTCTTAAAACCGTTAAA

GAAATAACGGGGTTTTTGCTCATTCAAGCGTGGCCAGAAAATCGCACTGACCTCCATGCT

TTCGAGAACCTGGAGATTATAAGAGGACGAACTAAGCAGCATGGTCAATTCTCCCTTGCT

GTGGTCAGCCTGAACATCACCAGTCTTGGTTTGCGGTCCCTCAAGGAAATTTCAGATGGA

GATGTCATCATAAGCGGCAACAAGAATTTGTGCTATGCAAATACCATAAACTGGAAAAAA

CTGTTTGGCACTTCCGGCCAGAAAACCAAGATTATTTCAAATCGGGGTGAGAACAGCTGC

AAAGCCACCGGCCAGGTTTGTCATGCCTTGTGCTCTCCGGAAGGCTGTTGGGGGCCAGAA

CCCAGGGACTGCGTCAGTTGCAGAAACGTCTCAAGAGGCCGCGAATGCGTTGACAAGTGT

AACCTCCTTGAGGGTGAGCCACGAGAGTTTGTTGAGAACAGCGAGTGTATACAATGTCAC

CCTGAATGTTTGCCCCAGGCTATGAATATAACCTGCACAGGCCGCGGGCCTGATAACTGC

ATCCAGTGTGCTCATTACATAGATGGACCTCACTGTGTGAAAACCTGCCCGGCCGGAGTT

ATGGGAGAAAACAACACTCTGGTGTGGAAATACGCTGATGCAGGCCACGTGTGCCACCTT

TGTCACCCGAATTGTACATATGGGTGTACCGGTCCTGGACTTGAAGGTTGCCCTACCAAT

-continued

GGCCCTAAAATACCCAGTATCGCAACTGGCATGGTAGGCGCTCTTCTCTTGCTCTTGGTA

GTTGCTCTCGGCATAGGTCTTTTTATG

SEQ ID NO: 76 amino acid sequence of LTG_ D0015 (Ef1a_CD33_4 VH CD8 BBz T2A tEGFR)
MLLLVTSLLLCELPHPAFLLIPEVQLVESGGGLVQPGGSLRLSCAASGFTFSSYGMSWVR

QAPRQGLEWVANIKQDGSEKYYADSVKGRFTISRDNSKNTLYLQMNSLRAEDTATYYCAK

ENVDWGQGTLVTVSSAAATTTPAPRPPTPAPTIASQPLSLRPEACRPAAGGAVHTRGLDF

ACDIYIWAPLAGTCGVLLLSLVITLYCKRGRKKLLYIFKQPFMRPVQTTQEEDGCSCRFP

EEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPP

RSRAKRSGSGEGRGSLLTCGDVEENPGPRAKRMLLLVTSLLLCELPHPAFLLIPRKVCNG

IGIGEFKDSLSINATNIKHFKNCTSISGDLHILPVAFRGDSFTHTPPLDPQELDILKTVK

EITGFLLIQAWPENRTDLHAFENLEIIRGRTKQHGQFSLAVVSLNITSLGLRSLKEISDG

DVIISGNKNLCYANTINWKKLFGTSGQKTKIISNRGENSCKATGQVCHALCSPEGCWGPE

PRDCVSCRNVSRGRECVDKCNLLEGEPREFVENSECIQCHPECLPQAMNITCTGRGPDNC

IQCAHYIDGPHCVKTCPAGVMGENNTLVWKYADAGHVCHLCHPNCTYGCTGPGLEGCPTN

GPKIPSIATGMVGALLLLLVVALGIGLFM

SEQ ID NO: 77 nucleotide sequence of LTG_D0016 (Ef1a CD33_4 VH CD8 28z T2A tEGFR)
ATGCTGCTGCTGGTGACCAGCCTGCTGCTGTGCGAACTGCCGCATCCGGCGTTTCTGCTG

ATTCCGGAGGTGCAGCTGGTGGAGTCTGGGGGAGGCTTGGTACAGCCTGGAGGGTCCCTG

AGACTCTCCTGTGCAGCCTCTGGATTCACCTTCAGTAGCTATGGCATGAGCTGGGTCCGC

CAGGCTCCAAGACAAGGGCTTGAGTGGGTGGCCAACATAAAGCAAGATGGAAGTGAGAAA

TACTATGCGGACTCAGTGAAGGGCCGATTCACCATCTCCAGAGACAATTCCAAGAACACG

CTGTATCTGCAAATGAACAGCCTGAGAGCCGAGGACACAGCCACGTATTACTGTGCGAAA

GAAAATGTGGACTGGGGCCAGGGCACCCTGGTCACCGTCTCCTCAGCGGCCGCGACTACC

ACTCCTGCACCACGGCCACCTACCCCAGCCCCCACCATTGCAAGCCAGCCACTTTCACTG

CGCCCCGAAGCGTGTAGACCAGCTGCTGGAGGAGCCGTGCATACCCGAGGGCTGGACTTC

GCCTGTGACATCTACATCTGGGCCCCATTGGCTGGAACTTGCGGCGTGCTGCTCTTGTCT

CTGGTCATTACCCTGTACTGCCGGTCGAAGAGGTCCAGACTCTTGCACTCCGACTACATG

AACATGACTCCTAGAAGGCCCGGACCCACTAGAAAGCACTACCAGCCGTACGCCCCTCCT

CGGGATTTCGCCGCATACCGGTCCAGAGTGAAGTTCAGCCGCTCAGCCGATGCACCGGCC

TACCAGCAGGGACAGAACCAGCTCTACAACGAGCTCAACCTGGGTCGGCGGGAAGAATAT

GACGTGCTGGACAAACGGCGCGGCAGAGATCCGGAGATGGGGGGAAAGCCGAGGAGGAAG

AACCCTCAAGAGGGCCTGTACAACGAACTGCAGAAGGACAAGATGGCGGAAGCCTACTCC

GAGATCGGCATGAAGGGAGAACGCCGGAGAGGGAAGGGTCATGACGGACTGTACCAGGGC

CTGTCAACTGCCACTAAGGACACTTACGATGCGCTCCATATGCAAGCTTTGCCCCCGCGG

AGAGCTAAACGCTCTGGGTCTGGTGAAGGACGAGGTAGCCTTCTTACGTGCGGAGACGTG

GAGGAAAACCCAGGACCCCGAGCCAAACGAATGCTGCTGCTTGTTACAAGCCTTTTGCTC

TGCGAACTCCCCCATCCAGCTTTTCTCCTGATTCCAAGGAAGGTTTGCAATGGAATCGGT

ATAGGGGAGTTTAAGGATTCACTTAGCATAAACGCTACTAATATTAAACACTTCAAAAAC

TGTACGAGTATAAGTGGAGATCTTCACATTTTGCCGGTTGCATTCCGAGGCGATTCATTC

-continued
ACCCACACGCCACCGCTTGACCCACAAGAATTGGATATTCTTAAAACCGTTAAAGAAATA

ACGGGGTTTTTGCTCATTCAAGCGTGGCCAGAAAATCGCACTGACCTCCATGCTTTCGAG

AACCTGGAGATTATAAGAGGACGAACTAAGCAGCATGGTCAATTCTCCCTTGCTGTGGTC

AGCCTGAACATCACCAGTCTTGGTTTGCGGTCCCTCAAGGAAATTTCAGATGGAGATGTC

ATCATAAGCGGCAACAAGAATTTGTGCTATGCAAATACCATAAACTGGAAAAAACTGTTT

GGCACTTCCGGCCAGAAACCAAGATTATTTCAAATCGGGGTGAGAACAGCTGCAAAGCC

ACCGGCCAGGTTTGTCATGCCTTGTGCTCTCCGGAAGGCTGTTGGGGGCCAGAACCCAGG

GACTGCGTCAGTTGCAGAAACGTCTCAAGAGGCCGCGAATGCGTTGACAAGTGTAACCTC

CTTGAGGGTGAGCCACGAGAGTTTGTTGAGAACAGCGAGTGTATACAATGTCACCCTGAA

TGTTTGCCCCAGGCTATGAATATAACCTGCACAGGCCGCGGGCCTGATAACTGCATCCAG

TGTGCTCATTACATAGATGGACCTCACTGTGTGAAAACCTGCCCGGCCGGAGTTATGGGA

GAAAACAACACTCTGGTGTGGAAATACGCTGATGCAGGCCACGTGTGCCACCTTTGTCAC

CCGAATTGTACATATGGGTGTACCGGTCCTGGACTTGAAGGTTGCCCTACCAATGGCCCT

AAAATACCCAGTATCGCAACTGGCATGGTAGGCGCTCTTCTCTTGCTCTTGGTAGTTGCT

CTCGGCATAGGTCTTTTTATG

SEQ ID NO: 78
amino acid sequence of LTG_D0016 (Ef1a CD33_4 VH CD8 28z T2A tEGFR)
MLLLVTSLLLCELPHPAFLLIPEVQLVESGGGLVQPGGSLRLSCAASGFTFSSYGMSWVR

QAPRQGLEWVANIKQDGSEKYYADSVKGRFTISRDNSKNTLYLQMNSLRAEDTATYYCAK

ENVDWGQGTLVTVSSAAATTTPAPRPPTPAPTIASQPLSLRPEACRPAAGGAVHTRGLDF

ACDIYIWAPLAGTCGVLLLSLVITLYCRSKRSRLLHSDYMNMTPRRPGPTRKHYQPYAPP

RDFAAYRSRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

RAKRSGSGEGRGSLLTCGDVEENPGPRAKRMLLLVTSLLLCELPHPAFLLIPRKVCNGIG

IGEFKDSLSINATNIKHFKNCTSISGDLHILPVAFRGDSFTHTPPLDPQELDILKTVKEI

TGFLLIQAWPENRTDLHAFENLEIIRGRTKQHGQFSLAVVSLNITSLGLRSLKEISDGDV

IISGNKNLCYANTINWKKLFGTSGQKTKIISNRGENSCKATGQVCHALCSPEGCWGPEPR

DCVSCRNVSRGRECVDKCNLLEGEPREFVENSECIQCHPECLPQAMNITCTGRGPDNCIQ

CAHYIDGPHCVKTCPAGVMGENNTLVWKYADAGHVCHLCHPNCTYGCTGPGLEGCPTNGP

KIPSIATGMVGALLLLLVVALGIGLFM

SEQ ID NO: 79
nucleotide sequence of human IgG4 hinge
GAGAGCAAATACGGGCCGCCATGTCCCCCGTGTCCG SEQ ID NO: 80
amino acid sequence of human IgG4 hinge
ESKYGPPCPPCP SEQ ID NO: 81
nucleotide sequence of human IgG4 CH2 domain
GCACCACCAGTTGCTGGCCCTAGTGTCTTCTTGTTCCCTCCCAAGCCCAAAGACACCTTG

ATGATTTCCAGAACTCCTGAGGTTACCTGCGTTGTCGTAGATGTTTCTCAGGAGGACCCA

GAGGTCCAATTTAACTGGTACGTTGATGGGGTGGAAGTTCACAATGCGAAGACAAAGCCG

CGGGAAGAACAATTTCAGTCCACTTACCGGGTTGTCAGCGTTCTGACGGTATTGCATCAA

GACTGGCTTAATGGAAAGGAATATAAGTGTAAGGTGTCCAACAAAGGTTTGCCGAGCAGT

ATTGAGAAGACCATATCAAAGGCGAAG

SEQ ID NO: 82
amino acid sequence of human IgG4 CH2 domain
APPVAGPSVFLFPPKPKDTLMISRTPEVTCVVVDVSQEDPEVQFNWYV

DGVEVHNAKTKPREEQFQSTYRVVSVLTVLHQDWLNGKEYKCKVSNKGLPS

SIEKTISKA K

SEQ ID NO: 83
nucleotide sequence of human IgG4 CH3 domain
GGGCAGCCGCGCGAGCCACAAGTTTACACTTTGCCGCCATCTCAAGAGGAAATGACTAAA

AACCAGGTATCCTTGACATGCCTCGTAAAAGGATTTTATCCATCTGATATTGCTGTGGAA

TGGGAGTCTAACGGGCAGCCGGAAAATAATTACAAAACTACACCACCTGTGCTCGATTCA

GATGGAAGTTTCTTCCTTTACAGTAGACTTACGGTGGACAAATCTAGGTGGCAGGAAGGG

AATGTGTTTAGTTGTAGTGTAATGCACGAGGCACTTCATAACCACTATACACAGAAGTCA

CTGAGTTTGAGTCTTGGCAAA

SEQ ID NO: 84
amino acid sequence of human IgG4 CH3 domain
GQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

SEQ ID NO: 85
nucleotide sequence of human IgG4 hinge CH2 CH3 domain
GAGAGCAAATACGGGCCGCCATGTCCCCCGTGTCCGGCACCACCAGTTGCTGGCCCTAGT

GTCTTCTTGTTCCCTCCCAAGCCCAAAGACACCTTGATGATTTCCAGAACTCCTGAGGTT

ACCTGCGTTGTCGTAGATGTTTCTCAGGAGGACCCAGAGGTCCAATTTAACTGGTACGTT

GATGGGGTGGAAGTTCACAATGCGAAGACAAAGCCGCGGGAAGAACAATTTCAGTCCACT

TACCGGGTTGTCAGCGTTCTGACGGTATTGCATCAAGACTGGCTTAATGGAAAGGAATAT

AAGTGTAAGGTGTCCAACAAAGGTTTGCCGAGCAGTATTGAGAAGACCATATCAAAGGCG

AAGGGGCAGCCGCGCGAGCCACAAGTTTACACTTTGCCGCCATCTCAAGAGGAAATGACT

AAAAACCAGGTATCCTTGACATGCCTCGTAAAAGGATTTTATCCATCTGATATTGCTGTG

GAATGGGAGTCTAACGGGCAGCCGGAAAATAATTACAAAACTACACCACCTGTGCTCGAT

TCAGATGGAAGTTTCTTCCTTTACAGTAGACTTACGGTGGACAAATCTAGGTGGCAGGAA

GGGAATGTGTTTAGTTGTAGTGTAATGCACGAGGCACTTCATAACCACTATACACAGAAG

TCACTGAGTTTGAGTCTTGGCAAA

SEQ ID NO: 86
amino acid sequence of human IgG4 hinge CH2 CH3 domain
ESKYGPPCPPCPAPPVAGPSVFLFPPKPKDTLMISRTPEVTCVVVDVSQEDPEVQFNWYV

DGVEVHNAKTKPREEQFQSTYRVVSVLTVLHQDWLNGKEYKCKVSNKGLPSSIEKTISKA

KGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

SEQ ID NO: 87
nucleotide sequence of LTG_D0035 (Ef1a_CD33_4 VH H CH2 CH3
IgG4_CD8TM_CD28z)
ATGCTGCTGCTGGTGACCAGCCTGCTGCTGTGCGAACTGCCGCATCCGGCGTTTCTGCTG

ATTCCGGAGGTGCAGCTGGTGGAGTCTGGGGGAGGCTTGGTACAGCCTGGAGGGTCCCTG

AGACTCTCCTGTGCAGCCTCTGGATTCACCTTCAGTAGCTATGGCATGAGCTGGGTCCGC

CAGGCTCCAAGACAAGGGCTTGAGTGGGTGGCAACATAAAGCAAGATGGAAGTGAGAAA

TACTATGCGGACTCAGTGAAGGGCCGATTCACCATCTCCAGAGACAATTCCAAGAACACG

CTGTATCTGCAAATGAACAGCCTGAGAGCCGAGGACACAGCCACGTATTACTGTGCGAAA

GAAAATGTGGACTGGGGCCAGGGCACCCTGGTCACCGTCTCCTCAGCGGCCGCAGAGAGC

```
AAATACGGGCCGCCATGTCCCCCGTGTCCGGCACCACCAGTTGCTGGCCCTAGTGTCTTC

TTGTTCCCTCCCAAGCCCAAAGACACCTTGATGATTTCCAGAACTCCTGAGGTTACCTGC

GTTGTCGTAGATGTTTCTCAGGAGGACCCAGAGGTCCAATTTAACTGGTACGTTGATGGG

GTGGAAGTTCACAATGCGAAGACAAAGCCGCGGGAAGAACAATTTCAGTCCACTTACCGG

GTTGTCAGCGTTCTGACGGTATTGCATCAAGACTGGCTTAATGGAAAGGAATATAAGTGT

AAGGTGTCCAACAAAGGTTTGCCGAGCAGTATTGAGAAGACCATATCAAAGGCGAAGGGG

CAGCCGCGCGAGCCACAAGTTTACACTTTGCCGCCATCTCAAGAGGAAATGACTAAAAAC

CAGGTATCCTTGACATGCCTCGTAAAAGGATTTTATCCATCTGATATTGCTGTGGAATGG

GAGTCTAACGGGCAGCCGGAAAATAATTACAAAACTACACCACCTGTGCTCGATTCAGAT

GGAAGTTTCTTCCTTTACAGTAGACTTACGGTGGACAAATCTAGGTGGCAGGAAGGGAAT

GTGTTTAGTTGTAGTGTAATGCACGAGGCACTTCATAACCACTATACACAGAAGTCACTG

AGTTTGAGTCTTGGCAAAATCTACATCTGGGCGCCCTTGGCCGGGACTTGTGGGGTCCTT

CTCCTGTCACTGGTTATCACCCTTTACTGCCGGTCGAAGAGGTCCAGACTCTTGCACTCC

GACTACATGAACATGACTCCTAGAAGGCCCGGACCCACTAGAAAGCACTACCAGCCGTAC

GCCCCTCCTCGGGATTFCGCCGCATACCGGTCCAGAGTGAAGTTCAGCCGCTCAGCCGAT

GCACCGGCCTACCAGCAGGGACAGAACCAGCTCTACAACGAGCTCAACCTGGGTCGGCGG

GAAGAATATGACGTGCTGGACAAACGGCGCGGCAGAGATCCGGAGATGGGGGGAAAGCCG

AGGAGGAAGAACCCTCAAGAGGGCCTGTACAACGAACTGCAGAAGGACAAGATGGCGGAA

GCCTACTCCGAGATCGGCATGAAGGGAGAACGCCGGAGAGGGAAGGGTCATGACGGACTG

TACCAGGGCCTGTCAACTGCCACTAAGGACACTTACGATGCGCTCCATATGCAAGCTTTG

CCCCCGCGG
```

SEQ ID NO: 88
amino acid sequence of LTG_D0035 (Ef1a_CD33_4 VH H CH2 CH3 IgG4_CD8TM_CD28z)

```
MLLLVTSLLLCELPHPAFLLIPEVQLVESGGGLVQPGGSLRLSCAASGFTFSSYGMSWVR

QAPRQGLEWVANIKQDGSEKYYADSVKGRFTISRDNSKNTLYLQMNSLRAEDTATYYCAK

ENVDWGQGTLVTVSSAAAESKYGPPCPPCPAPPVAGPSVFLFPPKPKDTLMISRTPEVTC

VVVDVSQEDPEVQFNWYVDGVEVHNAKTKPREEQFQSTYRVVSVLTVLHQDWLNGKEYKC

KVSNKGLPSSIEKTISKAKGQPREPQVYTLPPSQEEMTKNQVSLTCLVKGFYPSDIAVEW

ESNGQPENNYKTTPPVLDSDGSFFLYSRLTVDKSRWQEGNVFSCSVMHEALHNHYTQKSL

SLSLGKIYIWAPLAGTCGVLLLSLVITLYCRSKRSRLLHSDYMNMTPRRPGPTRKHYQPY

APPRDFAAYRSVKFSRSADAPAYQQGQNQLYNELNLGRREEYDVLDKRRGRDPEMGGKP

RRKNPQEGLYNELQKDKMAEAYSEIGMKGERRGKHDGLYQGLSTATKDTYDALHMQAL

PPR
```

---

What is claimed is:

1. An isolated chimeric antigen receptor (CAR) comprising, from N terminus to C-terminus:
   (i) at least one extracellular antigen binding domain that binds to CD33 comprising a heavy chain variable region having the amino acid sequence set forth in SEQ ID NO:2 or SEQ ID NO:4 or a single chain fragment variable (ScFv) domain selected from the group consisting of SEQ ID NO: 6, 8, 10 and 12;
   (ii) a transmembrane domain comprising a transmembrane domain of a protein selected from the group consisting of the T-cell receptor (TCR) alpha chain, the TCR beta chain, the TCR zeta chain, CD28, CD3 epsilon, CD45, CD4, CD5, CD8, CD9, CD16, CD22, CD33, CD37, CD64, CD80, CD86, CD134, CD137 and CD154, or any combination thereof;
   (iii) at least one costimulatory domain comprising a functional signaling domain selected from the group consisting of OX40, CD70, CD27, CD28, CD5, ICAM-1, LFA-1 (CD111a/CD18), ICOS (CD278), DAP10, DAP12, and 4-1BB (CD137), or any combination thereof; and
   (iv) an intracellular signaling domain comprising a functional domain selected from the group consisting of a 4-1BB (CD137); CD28, and CD3 zeta signaling domain, or a combination thereof.

2. The isolated CAR of claim 1, wherein the transmembrane domain comprises the amino acid sequence of SEQ ID NO: 27, an amino acid sequence having 85%, 90%, 95%, 96%, 97%, 98% or 99% identity to the amino acid sequence of SEQ ID NO: 28.

3. The isolated CAR of claim 1, wherein the at least one extracellular antigen binding domain and the at least one intracellular signaling domain, or both are connected to the transmembrane domain by a linker or spacer domain.

4. The isolated CAR of claim 3, wherein the linker or spacer domain is derived from the extracellular domain of CD8, TNFRSF19, IgG4, or CD28, and is linked to the transmembrane domain.

5. A method of making a cell comprising transducing a T cell with a vector comprising a nucleic acid molecule encoding a chimeric antigen receptor (CAR) comprising, from N-terminus to C-terminus:
   (i) at least one extracellular antigen binding domain that binds to CD33 comprising a heavy chain variable region having the amino acid sequence set forth in SEQ ID NO:2 or SEQ ID NO:4 or a single chain fragment variable (ScFv) domain selected from the group consisting of SEQ ID NO: 6, 8, 10 and 12;
   (ii) a transmembrane domain comprising a transmembrane domain of a protein selected from the group consisting of the T-cell receptor (TCR) alpha chain, the TCR betachain, the TCR zeta chain, CD28, CD3 epsilon, CD45, CD4, CD5, CD8, CD9, CD16, CD22, CD33, CD37, CD64, CD80, CD86, CD134, CD137 and CD154, or any combination thereof;
   (iii) at least one costimulatory domain comprising a functional signaling domain selected from the group consisting of OX40, CD70, CD27, CD28, CD5, ICAM-1, LFA-1 (CD11a/CD18), ICOS (CD278), DAP10, DAP12, and 4-1BB (CD137), or any combination thereof; and
   (iv) an intracellular signaling domain comprising a functional domain selected from the group consisting of a 4-1BB (CD137), CD28, and CD3 zeta signaling domain, or a combination thereof.

6. The method of claim 5, wherein the transmembrane domain comprises the amino acid sequence of SEQ ID NO: 27, an amino acid sequence having 85%, 90%, 95%, 96%, 97%, 98% or 99% identity to the amino acid sequence of SEQ ID NO: 28.

7. The method of claim 5, wherein the at least one extracellular antigen binding domain and the at least one intracellular signaling domain, or both are connected to the transmembrane domain by a linker or spacer domain.

8. The method of claim 7, wherein the linker or spacer domain is isolated from the extracellular domain of CD8, TNFRSF19, IgG4, or CD28, and is linked to the transmembrane domain.

9. A method of generating a population of RNA-engineered cells comprising introducing an in vitro transcribed RNA or synthetic RNA into a cell, where the RNA encodes a chimeric antigen receptor (CAR) comprising, from N-terminus to C-terminus:

(i) at least one extracellular antigen binding domain that binds to CD33 comprising a heavy chain variable region having the amino acid sequence set forth in SEQ ID NO:2 or SEQ ID NO:4 or a single chain fragment variable (ScFv) domain selected from the group consisting of SEQ ID NO: 6, 8, 10 and 12;

(ii) a transmembrane domain comprising a transmembrane domain of a protein selected from the group consisting of the T-cell receptor (TCR) alpha chain, the TCR betachain, the TCR zeta chain, CD28, CD3 epsilon, CD45, CD4, CD5, CD8, CD9, CD16, CD22, CD33, CD37, CD64, CD80, CD86, CD134, CD137 and CD154, or any combination thereof;

(iii) at least one costimulatory domain comprising a functional signaling domain selected from the group consisting of OX40, CD70, CD27, CD28, CD5, ICAM-1, LFA-1 (CD11a/CD18), ICOS (CD278), DAP10, DAP12, and 4-1BB (CD137), or any combination thereof; and (iv) an intracellular signaling domain comprising a functional domain selected from the group consisting of a 4-1BB (CD137), CD28, and CD3 zeta signaling domain, or a combination thereof.

10. The method of claim 9, wherein the transmembrane domain comprises the amino acid sequence of SEQ ID NO: 27, or an amino acid sequence having 85%, 90%, 95%, 96%, 97%, 98% or 99% identity to the amino acid sequence of SEQ ID NO: 28.

11. The method of claim 9, wherein the at least one extracellular antigen binding domain and the at least one intracellular signaling domain, or both are connected to the transmembrane domain by a linker or spacer domain.

12. The method of claim 11, wherein the linker or spacer domain is isolated from the extracellular domain of CD8, TNFRSF19, IgG4, or CD28, and is linked to the transmembrane domain.

13. The isolated CAR of claim 1, wherein the CAR comprises the amino acid sequence of SEQ ID NO: 16, 18, 20, 22, 24, 26, 70, 72, 74, 76, 78, or 88.

14. The method of claim 5, wherein the CAR comprises the amino acid sequence of SEQ ID NO: 16, 18, 20, 22, 24, 26, 70, 72, 74, 76, 78, or 88.

15. The method of claim 9, wherein the CAR comprises the amino acid sequence of SEQ ID NO: 16, 18, 20, 22, 24, 26, 70, 72, 74, 76, 78, or 88.

* * * * *